US009221875B2

(12) United States Patent
Yang et al.

(10) Patent No.: US 9,221,875 B2
(45) Date of Patent: *Dec. 29, 2015

(54) AMPHIPHILIC PEPTIDES FOR TREATMENT OF KERATITIS

(71) Applicant: Agency for Science, Technology and Research, Singapore (SG)

(72) Inventors: Yi-Yan Yang, Singapore (SG); Zhan Yuin Ong, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 14/321,624

(22) Filed: Jul. 1, 2014

(65) Prior Publication Data

US 2015/0005228 A1 Jan. 1, 2015

Related U.S. Application Data

(63) Continuation-in-part of application No. 14/353,531, filed as application No. PCT/SG2013/000378 on Aug. 29, 2013.

(51) Int. Cl.
| | | |
|---|---|---|
| *A61K 38/08* | (2006.01) | |
| *C07K 7/06* | (2006.01) | |
| *C07K 7/08* | (2006.01) | |
| *A01N 47/44* | (2006.01) | |
| *A61K 38/00* | (2006.01) | |

(52) U.S. Cl.
CPC . *C07K 7/08* (2013.01); *A01N 47/44* (2013.01); *A61K 38/08* (2013.01); *C07K 7/06* (2013.01); *A61K 38/00* (2013.01)

(58) Field of Classification Search
CPC ............. A61K 38/08; C07K 7/06; C07K 7/08
USPC ............ 514/20.8, 2.4, 105, 2.7, 3.3, 3.4, 3.7, 514/2.6
See application file for complete search history.

(56) References Cited

U.S. PATENT DOCUMENTS 7,858,585 B2 * 12/2010 Ozbas et al. ................. 514/21.4
7,884,185 B2 * 2/2011 Schneider et al. ............ 530/326

FOREIGN PATENT DOCUMENTS

| WO | 03092631 A2 | 11/2003 |
| WO | 03092632 A2 | 11/2003 |
| WO | WO-03092631 A2 | 11/2003 |
| WO | WO-03092632 A2 | 11/2003 |

OTHER PUBLICATIONS

Hancock et al, "Cationic peptides: a new source of antibiotics," TIBTECH, Feb. 1998, vol. 16: 82-88.*
Ong, et al, "Short Synthetic β-Sheet Forming Peptide Amphiphiles as Broad Spectrum Antimicrobials with Antibiofilnn and Endotoxin Neutralizing Capabilities," Advances Functional Materials, vol. 23, 2013, pp. 3682-3692.
Lee et al., "Effects of Single D-Amino Acid Substituion on Disruption of β-Sheet Structure and Hydrophobicity in Cyclic 14-Residue Antimicrobial Peptide Analogs Related to Gramicidin S," Journal of Peptide Research, vol. 63, No. 2, Feb. 2004, pp. 69-84.
International Search Report for International Application No. PCT/SG2013/000378 dated Nov. 27, 2013, pp. 1-5.

* cited by examiner

*Primary Examiner* — Julie Ha
(74) *Attorney, Agent, or Firm* — Winstead, P.C.

(57) ABSTRACT

Disclosed is the method of treating keratits in a subject thereof comprising administering into the subject an amphiphilic peptides of the present disclosure. Also disclosed are methods of removing biofilm from cornea.

6 Claims, 25 Drawing Sheets

AMPHIPHILIC PEPTIDES FOR TREATMENT OF KERATITIS

CROSS-REFERENCE TO RELATED APPLICATIONS

This application is a continuation-in-part of U.S. application Ser. No. 14/353,531 filed Apr. 23, 2014, which is a national stage application of PCT Application No. PCT/SG2013/000378 filed Aug. 29, 2013, which claims the benefit of priority of Singapore patent application No. 201206407-7, filed Aug. 29, 2012, the contents of each being hereby incorporated by reference in their entirety for all purposes.

FIELD OF THE INVENTION

The present invention generally relates to antimicrobial peptides and methods for their use.

BACKGROUND OF THE INVENTION

Despite significant improvements in living standards and biomedical technologies over the past century, the global burden of infectious diseases remains exceedingly high and is a major cause of public health, economic and social problems. According to World Health Organization (WHO) statistics, infectious and parasitic diseases such as pneumonia, tuberculosis, meningitis, diarrheal diseases, HIV and malaria are the second leading causes of death worldwide. The widespread and often indiscriminate use of antibiotics in industrialized nations further fuels the problem by contributing to the rapid emergence of drug resistant pathogens, making infectious diseases increasingly difficult to control with the existing classes of antibiotics. The exploding crisis of antibiotic-resistant infections coupled with the on-going dearth in new small-molecule antibiotics development, have spurred considerable efforts toward the discovery and development of membrane active antimicrobial peptides (AMPs) as an alternative class of antimicrobial agents. Naturally occurring antimicrobial peptides, also known as 'host defense peptides', were first discovered as components of the innate immunity, forming the first line of defense against invading pathogens in all living organisms. Unlike conventional antibiotics that inhibit specific biosynthetic pathways such as cell wall or protein synthesis, the majority of the cationic antimicrobial peptides exert their activities via physical disruption of the more negatively charged microbial membrane lipid bilayers to induce leakage of cytoplasmic components leading to cell death. The physical nature of membrane disruption is believed to result in a lower likelihood for drug resistance development as it becomes metabolically 'costlier' for the microorganism to mutate or to repair its membrane components at the same rate as the damage is being inflicted.

Although more than 1700 naturally occurring antimicrobial peptides from diverse sources including microorganisms, plants and animals have been isolated and characterized in the past 3 decades, only very few AMPs such as polymyxins and gramicidins are being used clinically; and mainly in topical formulations due to their high systemic toxicities. The major challenges identified with the application of antimicrobial peptides as drugs lie in the high cost in synthesizing long peptide sequences, poor stability and unknown toxicity after systemic administration. In efforts to enhance antimicrobial activities and minimize non-specific toxicities, more researchers are increasingly utilizing naturally occurring antimicrobial peptide or protein sequences as templates to perform chemical modifications such as cyclization, sequence truncations, and substitution with D-, β- or fluorinated-amino acids for the generation of new peptide analogs with broader applications for localized or systemic infections within the body. However, current approaches to optimize naturally occurring antimicrobial peptide sequences remain largely empirical at best, making it extremely difficult to delineate general structure-activity relationships especially against the backdrop of massive sequence and structural diversities. Furthermore, many of the new peptide analogs remain long (20 amino acids or more), which might induce significant immunogenicity and ultimately increase the cost for large scale manufacturing. More importantly, it has been suggested that the use of antimicrobial peptides with sequences that are too close to the host defense antimicrobial peptides may trigger the development of resistance towards innate AMPs that could inevitably compromise natural defenses against infections, posing significant health and environmental risks.

At the same time, the rapid emergence of antibiotics resistant bacteria and fungi in both the nosocomial and community settings has created a significant strain on healthcare systems around the world. While global incidences of antibiotics resistant pathogens such as methicillin-resistant *Staphylococcus aureus* (MRSA), vancomycin-resistant *Enterococci* (VRE) and multidrug-resistant *Klebsiella pneumoniae* and *Acinetobacter* spp. have reached epidemic levels, the number of new antibiotics entering the clinical development pipeline has been dismal; with only three new structural classes of antibiotics including the oxazolidinones (linezolid), lipopeptides (daptomycin) and pleuromutilins (retapamulin) entering the market since 2000. This development is especially alarming given that pathogenic bacteria such as *S. aureus*, *Enterobacter* and *Klebsiella* are developing resistance to vancomycin and carbapenems, which are potent antibiotics traditionally reserved as the last line of defense for vulnerable patients in hospitals. With the on-going dearth in small molecular antibiotics development, the design and identification of alternative classes of antimicrobial agents with new modes of action that can effectively overcome drug resistance mechanisms is more pressing than ever.

As the majority of the antimicrobial peptides exert their antimicrobial activities through a rapid and direct membrane lytic mechanism, they possess an inherent advantage in overcoming conventional mechanisms of antibiotics resistance such as the increased expression of drug efflux pumps on microbial membranes, production of drug degradation enzymes or alteration to drug interaction sites acquired by microbes against small molecular antibiotics targeting specific biosynthetic pathways. Significant barriers limiting the successful clinical translation of antimicrobial peptides, however, include high systemic toxicities as a result of poor microbial membrane selectivities, relatively high manufacturing cost (for long peptide sequences) and susceptibility to degradation by proteases present in biological fluids such as blood serum, wound exudates or lacrimal fluids.

Keratitis continues to be an important cause of ocular morbidity, and it is also a major eye disease that leads to blindness. Symptoms of keratitis include pain and redness in the eye, blurred vision, sensitivity to light, and excessive tearing or discharge. It may lead to severe vision loss and scars on the cornea. Moreover, the incidence of keratitis has increased over the past 30 years mainly due to the frequent use of topical corticosteroids and antibacterial agents in the treatment of patients with keratitis, as well as the rise in the number of patients who are immunocompromised.

Causes of keratitis include herpes simplex virus type 1, varicella zoster, and adenoviruses, bacteria, parasites, fungi and vitamin A deficiency. An outbreak of keratitis was reported in 2005 and 2006 in the United States and also in France, Hong Kong and Singapore. Most of the cases in the United States involved soft contact lens wear, which was mainly caused by fungal infections.

Keratitis remains a diagnostic and therapeutic challenge to the ophthalmologist due to several reasons. The main challenge is fast and accurate diagnosis. Diagnosis of keratitis is typically conducted by culture or corneal biopsy. However, isolating and identifying the species of organism in the laboratory take time, leading to late diagnosis frequently. Furthermore, as keratitis can be caused by various microorganisms, the different types of keratitis are often misdiagnosed as one another. For example, fungal keratitis is often misdiagnosed as bacterial keratitis as clinicians often consider fungal keratitis only after a presumed bacterial keratitis worsens during antibiotic therapy. Moreover, anti-fungal sensitivity testing is unreliable, and correlates poorly with clinical efficacy. Even if the diagnosis is made accurately, management of the condition remains a challenge because of the poor corneal penetration and the limited commercial availability of agents useful in treating keratitis.

Most commercially available medications are merely fungistatic or bactericidal, and they require an intact immune system and prolonged therapeutic course for successful resolution of the condition. Such microbe specific medications are disadvantages as it requires specific diagnosis of the cause of keratitis before treatment can be provided. Furthermore, commercially available anti-fungal medication does not address the fact that fungal keratitis infection often exists as a biofilm, which is particularly difficult to remove because fungal cells are encapsulated in a protective and impermeable extracellular matrix (ECM). Therefore, typically, treatment requires significantly higher doses of antifungal agents in an attempt to clear biofilm.

Furthermore, current commercial drugs include azole compounds (such as funconazole) and polyenes (such as amphopterin B, nystatin and natamycin). The azoles are fungistatic, which function by enzyme inhibition and are prone to drug resistance development. However, azoles available in the art are extremely unstable; their topical solution must be kept refrigerated for no more than 48 hours and protected from light. Another antifungal drugs known in the art are the polyenes, which function via disrupting the permeability of ions through the cell membrane, are rather expensive, poorly water soluble and quite unstable in aqueous, acid or alkaline media, or when exposed to light and excessive heat. All these limit their clinical applications.

In view of the above, there is a need to provide alternative agents useful for treating keratitis caused by various microbes. There is also a need to provide alternative agents useful for treating keratitis that is stable and safe to use.

SUMMARY OF THE INVENTION

In one aspect, there is provided the method of treating keratitis in a subject comprising administering an effective amount of an amphiphilic peptide comprising $(X_1Y_1X_2Y_2)_n$ (Formula I), wherein the C-terminal end of the peptide is amidated; $X_1$ and $X_2$ is independently of each other a hydrophobic amino acid; $Y_1$ and $Y_2$ is independently of each other a cationic amino acid and wherein n is at least 1.5, wherein the peptide is capable of self-assembly into b-sheet structure in to the subject in need thereof.

In another aspect, there is provided the peptide as described herein for treating keratitis in a subject.

In another aspect, there is provided a method of treating keratitis in a subject. The method comprises the administration of a pharmaceutically effective amount of a peptide as described herein.

In another aspect, there is provided a method of removing a biofilm from a cornea of a subject. The method comprises the administration of a peptide as described herein.

BRIEF DESCRIPTION OF THE DRAWINGS

The invention will be better understood with reference to the detailed description when considered in conjunction with the non-limiting examples and the accompanying drawings, in which:

FIG. 2 demonstrates how the peptides of the present disclosure readily self-assembled into β-sheet secondary structures in a microbial membrane mimicking condition (25 mM SDS solution).

FIG. 3 shows that the peptides of the present disclosure induced minimal or no haemolysis against rat red blood cells at various minimum inhibitory concentration (MIC) values.

FIG. 4 shows that the peptides of the present disclosure are bactericidal at MIC values and above.

FIG. 5 shows that the peptides of the present disclosure can cause membrane lysis in *Escherichia coli* and *Staphylococcus aureus*.

FIG. 6 shows that the peptides of the present disclosure demonstrated a dose-dependent killing of *Staphylococcus aureus* residing in biofilms.

FIG. 7 demonstrates that the peptides of the present disclosure can be used to remove biofilms.

FIG. 8 demonstrates that the peptides of the present invention are effective in disrupting lipopolysaccharide (LPS) aggregates.

FIG. 9 demonstrates that the peptides of the present disclosure are effective in neutralizing the effect of LPS.

FIG. 10 shows that the anti-inflammatory property of the peptides of the present disclosure was independent of their effects on cell viability and that the peptides were not cytotoxic at concentrations required for antimicrobial and anti-inflammatory activities.

FIG. 11 shows the peptides of the present disclosure readily self-assembled to form β-sheet secondary structure in microbial membrane mimicking conditions.

FIG. 12 shows the D-stereoisomers of the peptides of the present disclosure exhibit minimal or no haemolysis at MIC values, with high selectivity for microbial membranes.

FIG. 13 shows all the D enantiomers of the peptides of the present disclosure are protease resistant.

FIG. 14 demonstrates that similar to the L-enantiomers, the D-enantiomers of the peptide of the present disclosure have bactericidal mechanisms.

FIG. 15 demonstrates the D-enantiomers of the peptides of the present disclosure can cause membrane lysis in *Staphylococcus aureus* and *Pseudomonas aeruginosa*.

FIG. 16 suggests that the peptide of the present disclosure does not induce any development of drug resistance within the timeframe tested.

FIG. 17 demonstrates that the peptides of the present disclosure have potent antimicrobial properties against bacteria present within infected cells.

FIG. 18 demonstrates that both the enantiomers and stereoisomers of the peptides of the present disclosure remained as random coils and did not adopt any secondary structures in deionized water.

FIG. 19 shows that in contrast to L-enantiomers, the treatment of proteases on D-enantiomer peptides of the present disclosure does not lead to degradation of the D-enantiomer peptides.

FIG. 20 demonstrates that D-enantiomers of the peptides of the present disclosure is able to inhibit gentamicin- and ciprofloxacin-resistant *Escherichia coli* at the same concentration as that of wild-type (non-drug resistant) *Escherichia coli*.

FIG. 21 demonstrates that the D-enantiomers of the peptides of the present disclosure are only cytotoxic at concentrations that are well above the antimicrobial concentrations.

FIG. 23 shows significant decreased in *C. albicans* numbers after 2 hours treatment at MIC level. Most fungi were eradicated at 4 hours at MIC and at 1 hour at 2×MIC or 4×MIC. Thus, FIG. 23 illustrates the peptide of the present disclosure to be a useful antifungal agent against *C. albicans*.

FIG. 24A shows 90% of *C. albicans* cells were killed in 24 hours after a single treatment of 500 mg/L of peptide (IKIK)$_2$-NH$_2$. FIG. 24B shows significantly decreased *C. albicans* biomass after the treatment of the same peptide at the same concentration. Thus, FIG. 24 shows the peptide of the present disclosure to be useful in inducing death of *C. albicans* and in decreasing *C. albicans* biomass.

FIG. 25 shows the peptide of the present disclosure to be useful in deforming the morphology of *C. albicans* and in decreasing *C. albicans* biomass.

FIG. 26 shows the peptides of the present disclosure to be non-toxic to the eyes when used as eye drops.

FIG. 27 shows that the treatment efficacy of the peptides of the present disclosure was comparable with that of amphotericin B.

FIG. 28 shows that there was no significant difference in the scores of the amphotericin B-treated and peptides-treated eyes.

FIG. 30 shows that the peptides of the present disclosure were effective in eradicating the sessile keratitis-related fungi and their biofilms in mouse eyes.

BRIEF DESCRIPTION OF THE TABLE

Figure 1:
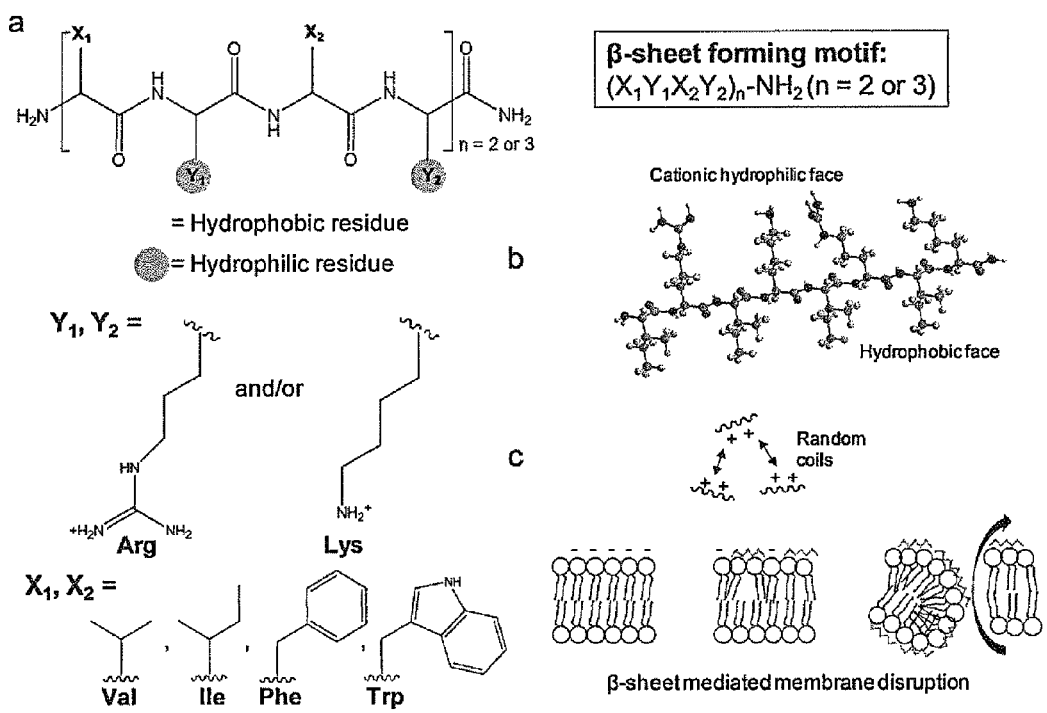
FIG. 1 shows design features of synthetic β-sheet forming peptides. A) shows exemplary peptide of the present disclosure. B) shows an example of the peptide of the present disclosure presented as a linear molecule. C) shows a schematic diagram of possible membrane disruption caused by the peptide of the present disclosure. In brief, in aqueous solutions, the peptides exist as monomeric random coils due to electrostatic repulsion between the protonated Arg and/or Lys residues. However, in the presence of microbial cell membranes, the peptides readily assemble into β-sheet secondary structures stabilized by electrostatic interactions between the positively charged residues and the negatively charged phospholipids, followed by the insertion of their hydrophobic residues into the lipid bilayer to mediate membrane disruption.

Table 1 shows the characterization of the peptides of the present disclosure.

Table 2 shows the minimum inhibitory concentrations (MICs) and selectivity indices of the peptides of the present disclosure.

Table 3 shows the design and characterization of the peptides of the present disclosure.

Table 4 shows the minimum inhibitory concentrations (MICs) and selectivity indices of the peptides of the present disclosure.

Table 5 shows the minimum microbicidal concentrations (MBCs) of the peptides of the present disclosure against clinically isolated drug resistant microorganisms.

Table 6 shows the minimum inhibitory concentrations (MICs) of the peptides of the present disclosure against clinically isolated Mycobacterium tuberculosis.

Table 7 shows the clinical grading and scoring of in vivo keratitis treatment.

Table 8 shows the minimum inhibitory concentrations (MICs) of the peptides of the present disclosure.

DETAILED DESCRIPTION OF THE PRESENT INVENTION

The design and optimization of short synthetic peptides with minimal resemblance to naturally occurring peptide sequences is a useful strategy for the development of safe and efficacious antimicrobial peptides for clinical use. Besides having a cationic character with net charges between +2 to +9 and comprising of ~30-50% of hydrophobic amino acid residues, one commonality of various naturally occurring and synthetic antimicrobial peptides lies in the folding of the amphipathic peptides to form secondary structures, often upon contact with microbial membranes. Between the two predominant forms of folded structures including α-helical peptides (e.g. cathelicidins, cecropins, magainins) and β-sheet peptides (e.g. defensins and protegrins), amphipathic β-sheet peptides have been found to be less haemolytic while possessing comparable antimicrobial activities to their α-helical counterparts of equal charge and hydrophobicity. Thus, it is the object of the present disclosure to provide a short synthetic peptide having β-sheet folding structures that have antimicrobial activities and are less haemolytic.

Keratitis is a leading cause of ocular morbidity. The different causes of keratitis are frequently misdiagnosed as one another, thus causing a delay in proper treatment. Furthermore, due to the lack of safe and effective anti-keratitis agents for clinical use, treatment of keratitis remains a challenge. In recent years, antimicrobial peptides (AMPs) have received considerable attention as potent and broad-spectrum antimicrobial agents with the potential to overcome antibiotics resistance. In the present disclosure, the inventors found that synthetic β-sheet forming peptide are useful for in vivo keratitis treatment in comparison with a non-β-sheet forming peptide and the commercially available amphotericin B.

Thus, in one aspect, there is provided the method of treating keratitis in a subject comprising administering an effective amount of an amphiphilic peptide comprising $(X_1Y_1X_2Y_2)_n$ (Formula I), wherein the C-terminal end of the peptide is amidated; $X_1$ and $X_2$ may be individually selected from the group consisting of hydrophobic amino acids; $Y_1$ and $Y_2$ may be individually selected from the group consisting of cationic amino acids; and n may be at least 1.5, wherein the peptide is capable of self-assembly into β-sheet structure, into a subject in need thereof. In one example, the inventors of the present disclosure designed short synthetic β-sheet folding peptides consisting of short recurring $(X_1Y_1X_2Y_2)_n$-$NH_2$ sequences based upon several basic design principles from naturally occurring β-sheet folding AMPs including, but not limited to: 1) the common occurrence of amphipathic dyad repeats in membrane-spanning β-sheets, 2) the requirement for hydrophobic residues (such as, but not limited to Val, Be, Phe and Trp) and cationic (such as, but not limited to Arg and Lys) and to interact and perturb microbial cell walls and membranes, and 3) the strong β-sheet folding propensities of Val, Ile, Phe and Trp.

As used herein, the term "amphiphilic peptide" refers to a peptide that possesses both hydrophilic and lipophilic properties, which is conferred by the peptide having cationic amino acids attached to hydrophobic amino acids. As used herein, the term "hydrophobic amino acid" refers to amino acid residues that are not soluble in water. In one example, the term "hydrophobic amino acid" may include, but is not limited to alanine (A), valine (V), leucine (L), isoleucine (I), phenylalanine (F), methionine (M), tryptophan (W), cysteine (C), tyrosine (Y), histidine (H), threonine (T), serine (S), proline (P) and glycine (G). In one example, the hydrophobic amino acid may be alanine (A), valine (V), leucine (L), isoleucine (I), phenylalanine (F), methionine (M), tryptophan (W) and cysteine (C). In one example, the hydrophobic amino acid may be isoleucine (I) or valine (V).

As used herein, the term "cationic amino acid" refers to amino acid residues which are soluble in water. In one example, the cationic amino acid may include, but is not limited to arginine (R), lysine (K) and histidine (H).

In one example, the amphiphilic peptide is an isolated peptide. As used herein, the term "isolated' refers to a peptide free of or substantially free of proteins, lipids, nucleic acids, for example, with which it is naturally associated.

In one example, the amphiphilic peptide may consists of $(X_1Y_1X_2Y_2)_n$ (Formula I), wherein $X_1$ and $X_2$ may be independently of each other a hydrophobic amino acid; $Y_1$ and $Y_2$ may be independently of each other a cationic amino acid. Thus, $X_1$ and $X_2$ may be the same or different amino acids and $Y_1$ and $Y_2$ may be the same or different amino acids.

In the present disclosure, n may not be 1 because peptides with four amino acids as described herein (for example $X_1Y_1X_2Y_2$ (SEQ ID NO: 1)) do not have antimicrobial activities and do not form β-sheets in microbial membrane environments. Accordingly, n may be between about 1.5 to 5. In one example, n may be 1.5, 2, 2.5, 3, 3.5, 4, 4.5 or 5.

In one example, the amphiphilic peptide may include, but is not limited to $X_1Y_1X_2Y_2X_3Y_3$ (SEQ ID NO: 2), $X_1Y_1X_2Y_2X_3Y_3X_4Y_4$ (SEQ ID NO: 3), $X_1Y_1X_2Y_2X_3Y_3X_4Y_4X_5Y_5$ (SEQ ID NO: 4), $X_1Y_1X_2Y_2X_3Y_3X_4Y_4X_5Y_5X_6Y_6$ (SEQ ID NO: 5), $X_1Y_1X_2Y_2X_3Y_3X_4Y_4X_5Y_5X_6Y_6X_7Y_7$ (SEQ ID NO: 6), $X_1Y_1X_2Y_2X_3Y_3X_4Y_4X_5Y_5X_6Y_6X_7Y_7X_8Y_8$ (SEQ ID NO: 7), $X_1Y_1X_2Y_2X_3Y_3X_4Y_4X_5Y_5X_6Y_6X_7Y_7X_8Y_8X_9Y_9$ (SEQ ID NO: 8) and $X_1Y_1X_2Y_2X_3Y_3X_4Y_4X_5Y_5X_6Y_6X_7Y_7X_8Y_8X_9Y_9X_{10}Y_{10}$ (SEQ ID NO: 9). In one example, $X_1$, $X_2$, $X_3$, $X_4$, $X_5$, $X_6$, $X_7$ and $X_8$, may be the same or independently different amino acids and $Y_1$, $Y_2$, $Y_3$, $Y_4$, $Y_5$, $Y_6$, $Y_7$ and $Y_8$, may be the same or independently different amino acids.

In one example, the peptides of the present disclosure may have C-terminal end that is amidated. The term "C-terminal end" is used herein in accordance to its definition as commonly known in the art, that is, can be used interchangeably with any of the following terminologies such as the carboxyl-terminus, carboxy-terminus, C-terminal tail, C-terminus or COOH-terminus, which refer to the end of an amino acid chain, terminated by a free carboxyl group (—COOH). As written herein, the peptides as described herein are presented as C-terminal end on the right and N-terminal end on the left. Thus, as used herein, the phrase "C-terminal end is amidated" refers to the substitution of the hydroxyl group of C-terminal end of the peptide of the present disclosure with a primary or secondary amine group. In one example, the peptides as described herein may be $(X_1Y_1X_2Y_2)_n$, which may be $(X_1Y_1X_2Y_2)_n$-$NH_2$. In one example, the peptides of the present disclosure may be amidated by process commonly known in the art. Without wishing to be bound by theory, it is believed that C-terminal amidation enhances antimicrobial activities presumably due to the reinforcement of cationic character; the peptides designed for this study were amidated at the C-terminal to confer a high net positive charge.

The peptides of the present disclosure does not require secondary structure stabilizer. The phrase "secondary structure stabilizer" refers to molecules that are capable of holding local spatial arrangement of a polypeptide's backbone atoms without regard to the conformations of its side chains. The secondary structure stabilizer as used herein may include, but is not limited to hydrophobic effect, electrostatic interactions and chemical cross-links such as disulphide bonds within and between polypeptide chains or metal ions internal cross-linking. In one example, the peptides of the present disclosure are distinct from existing β-sheet peptides known in the art in that they do not require disulphide bridges or other covalent bond constraints to stabilize the secondary structure. In aqueous solutions, the peptides of the present disclosure may be expected to exist as monomers due to electrostatic repulsion between the protonated Arg and/or Lys residues. In the presence of microbial cell membranes, the peptides of the present disclosure readily fold into secondary β-sheet structures stabilized by electrostatic interactions between the positively charged residues and the negatively charged phospholipids, followed by the insertion of its hydrophobic residues into the lipid bilayer. Thus, in one example, the peptide may be capable of self-assembly into β-sheet structure. As used herein, the term "self-assembly" refers to a type of process wherein a disordered system of pre-existing components forms an organized structure or pattern as a consequence of specific, local interactions among the components themselves, without external direction. In the present disclosure, the peptides may spontaneously form β-sheet structures in microbial membrane environments. As used herein, the phrase "microbial membrane environments" refers to microenvironment in the membrane of target microbes. In one example, this environment may be simulated by the presence of the anionic surfactant SDS. In one example, the peptides may not spontaneously form β-sheet structures in deionised water or aqueous solution.

As used herein, "β-sheet" or "β-pleated sheet structure" refers to a regular secondary structure of peptides that may comprise at least one β-strand, which is a stretch of polypeptide chain typically 3 to 12-amino acid long with backbone in an almost fully extended formation. In one example, the β-sheet structure of the present invention consists of at least one β-strand. Furthermore, in one example, the arrangement of the cationic and hydrophobic amino acids within the beta-sheet forming sequence may not be changed. As shown in examples provided in Table 1 and FIG. 11d, rearrangement of cationic and hydrophobic amino acids within the beta-sheet forming sequence can lead to a loss of secondary structure.

In one example, the peptides of the present disclosure may include: 1) choice of cationic amino acid residue (i.e. Arg vs. Lys vs. combination of both), 2) degree of polarity and bulkiness of the hydrophobic side chain, and 3) a specific length of peptide sequence. In the present disclosure, the various possible configurations of peptides of the present disclosure were systematically investigated for effects on antimicrobial and haemolytic activities. In some examples, peptides containing Arg have been found to have stronger antimicrobial properties compared to Lys-containing. Without wishing to be bound to theory, it was believed that the stronger antimicrobial properties of Arg rich peptides of the present disclosure may be due to the greater charge density of the guanidinium side chain. However, it is commonly believed in the art that the presence of numerous arginine residues within a peptide sequence is associated with a higher degree of haemolysis and cytotoxicity. Thus, both Arg and Lys were incorporated in the peptide designs to capitalize on the high charge density of Arg for improving antimicrobial effects while tuning the toxicity of the synthetic peptides using the less toxic Lys residue.

Figure 13:
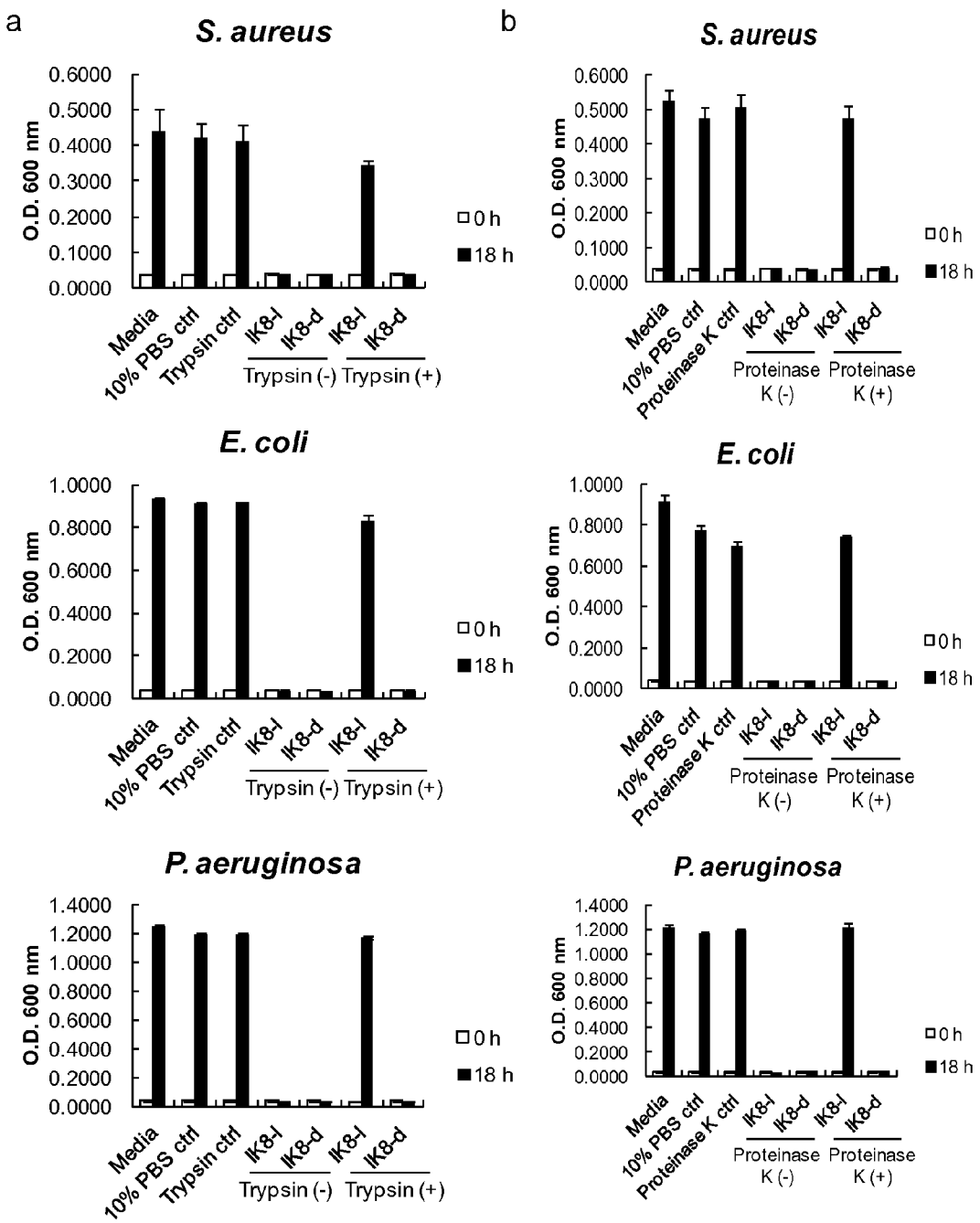
FIG. 13 shows antimicrobial activities of IK8-all L and IK8-all D against *Staphylococcus aureus*, *Escherichia coli* and *Pseudomonas aeruginosa* after 6 h treatment with proteases (a) trypsin and (b) proteinase K.
Figure 19:
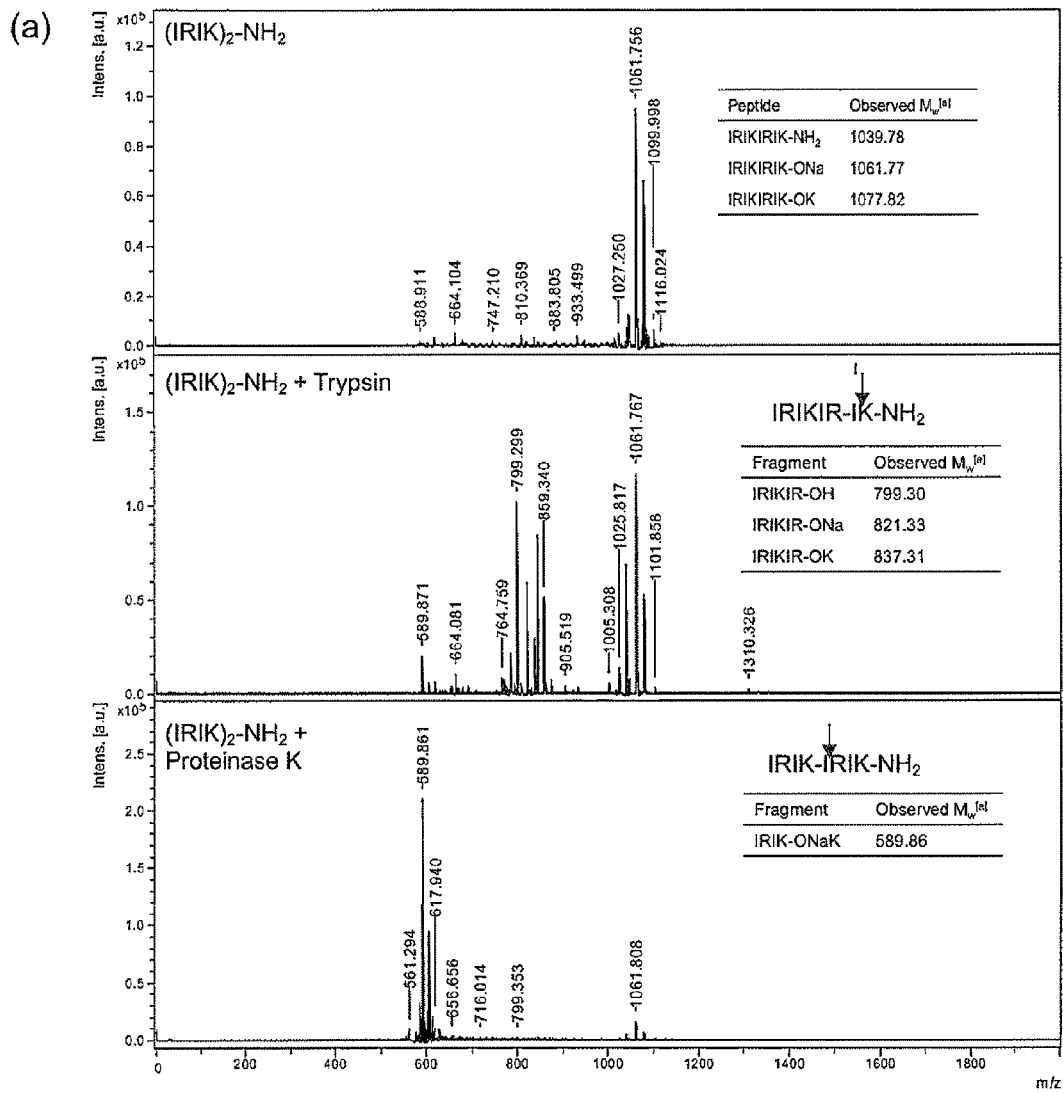
FIG. 19 shows MALDI-TOF mass spectra demonstrating proteolytic activity of trypsin and proteinase K on (a) (IRIK)$_2$-NH$_2$ (SEQ ID NO: 17) and (b) (irik)$_2$-NH$_2$ (SEQ ID NO: 18). Arrow indicates predominant enzyme cleavage site.
Figure 19:
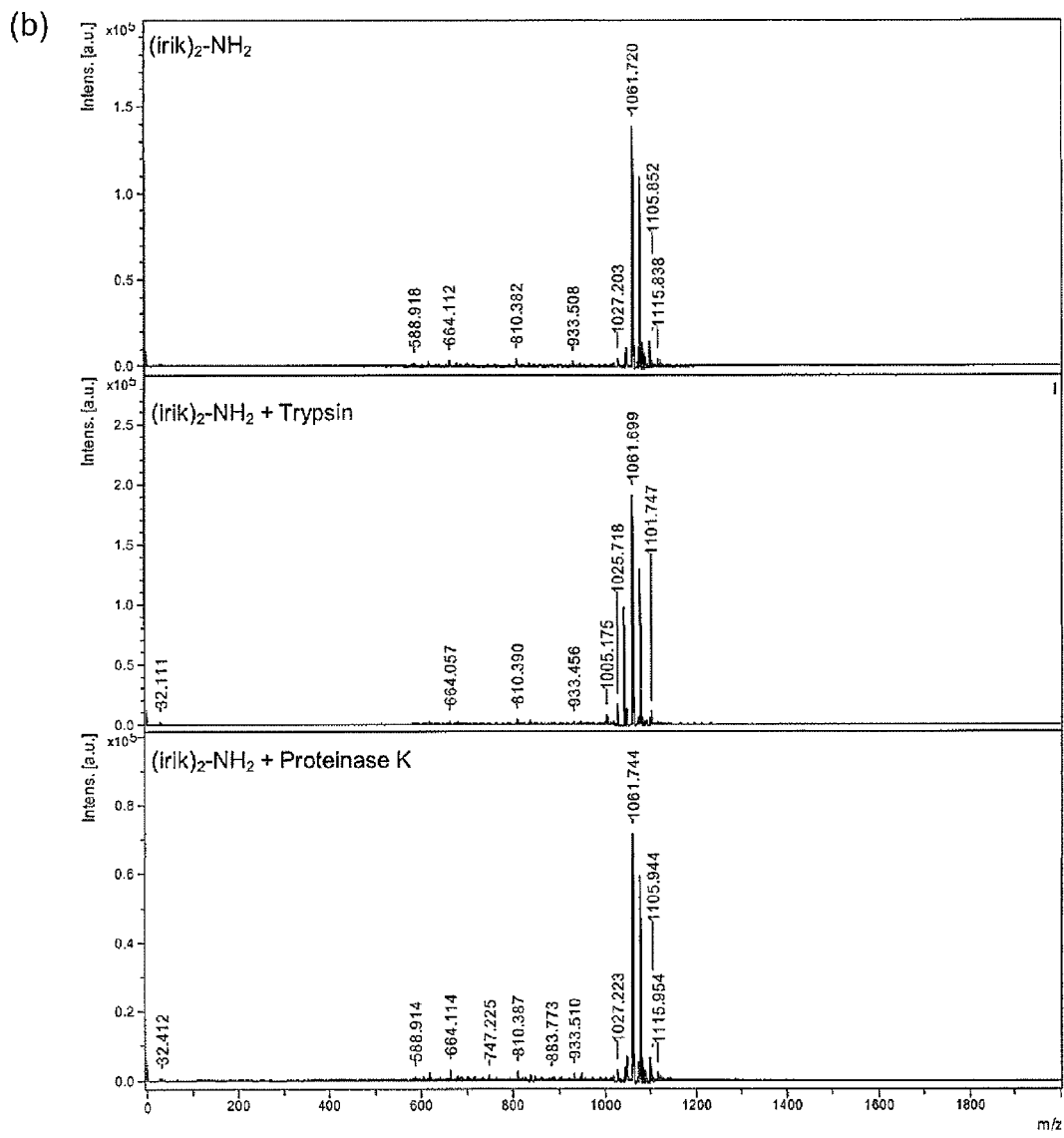

At the same time, in efforts to enhance the stability of the peptides of the present disclosure in biological fluids, the inventors of the present disclosure investigated the effect of stereochemistry on the antimicrobial activities of the synthetic peptides. Thus, in one example, there is provided peptides of the present disclosure which may have each repeating unit n of Formula I comprises independently of each other 1, or 2, or 3 or 4 D-amino acids with the remaining amino acids being L-amino acids. In one example, the repeating unit n of Formula I may comprise independently of each other 1, 2, 3, 4, 5, 6, 7, 8, 9, 10, 11, 12, 13, 14, 15, 16, 17, 18 or 19 D-amino acids with the remaining amino acids being L-amino acids. In one example, the repeating unit n of Formula I may comprise independently of each other 2 or 4 or 8 D-amino acids with the remaining amino acids being L-amino acids. As used herein, "L-amino acids" and "D-amino acids" refer to the two isomers that can occur in every amino acid. As written herein, small underlined residues represent D-amino acids while capital non-underlined represents L-amino acid. "L-amino acids" refer to the amino acid isomer which are manufactured in cells and incorporated into proteins. "D-amino acids" refers to isomeric modification to amino acids of the peptides of the present disclosure. Advantageously, "D-amino acids" may not be recognized by human and microbial proteases. Thus, as illustrated in FIGS. 13 and 19, the peptides of the present disclosure may be prevented from premature proteolytic degradation in vivo. However, as found by the inventors of the present disclosure, selective D-amino acid substitution at four positions led to a complete loss of secondary structure. Accordingly, in one example, the each repeating unit n of Formula I may comprise independently of each other 1 or 2 D-amino acids with the remaining amino acids being L-amino acids. In one example, the distribution of D-amino acids in each repeating unit n of Formula I may be identical or different from each other. In one example, the peptide as described herein, wherein n may be 2 and amino acids in position 4 and 6 may be D-amino acids while the remaining amino acids are L-amino acids. As illustrated in the Experimental Section, selective D-amino acid substitution at positions 4, 6, enabled the retention of secondary structure forming propensity (see FIG. 11c).

In one example, the peptides as described herein may comprise or consists of the sequence $(IY_1IY_2)_n$-$NH_2$. In one example, the peptides as described herein may comprise or consists of the sequence $(IRX_2K)_n$-$NH_2$.

In one example, the peptide as described herein when represented by general formula $X_1Y_1X_2Y_2X_3Y_3$ (SEQ ID NO: 2) may include, but is not limited to irikir-$NH_2$ (SEQ ID NO: 10), wherein small underlined residues represent D-amino acids. In one example, the peptide as described herein when represented by general formula $X_1Y_1X_2Y_2X_3Y_3X_4Y_4$ (SEQ ID NO: 3), may include, but is not limited to VRVKVRVK-$NH_2$ (SEQ ID NO: 11), IRIRIRIR-$NH_2$ (SEQ ID NO: 12), IKIKIKIK-$NH_2$ (SEQ ID NO: 13), IRVKIRVK-$NH_2$ (SEQ ID NO: 14), FRFKFRFK-$NH_2$ (SEQ ID NO: 15), WRWKWRWK-$NH_2$ (SEQ ID NO: 16), IRIKIRIK-$NH_2$ (SEQ ID NO: 17), irikirik-$NH_2$ (SEQ ID NO: 18) and IRIkIrIK-$NH_2$ (SEQ ID NO: 19), wherein small underlined residues represent D-amino acids while capital non-underlined represent L-amino acid. In one example, the peptide as described herein when represented by general formula $X_1Y_1X_2Y_2X_3Y_3X_4Y_4X_5Y_5X_6Y_6$ (SEQ ID NO: 5), may include, but is not limited to VRVKVRVKVRVK-$NH_2$ (SEQ ID NO: 20), IRIKIRIKIRIK-$NH_2$ (SEQ ID NO: 21), IRVKIRVKIRVK-$NH_2$ (SEQ ID NO: 22), and irvkirvkirvk-$NH_2$ (SEQ ID NO: 23), wherein small underlined residues represent D-amino acids while capital non-underlined represent L-amino acid. In one example, the peptides as described herein may be selected from the group consisting of VRVKVRVK-$NH_2$ (SEQ ID NO: 11), VRVKVRVKVRVK-$NH_2$ (SEQ ID NO: 20), IRIRIRIR-$NH_2$ (SEQ ID NO: 12), IKIKIKIK-$NH_2$ (SEQ ID NO: 13), IRVKIRVK-$NH_2$ (SEQ ID NO: 14), FRFKFRFK-$NH_2$ (SEQ ID NO: 15), WRWKWRWK-$NH_2$ (SEQ ID NO: 16), IRIKIRIK-$NH_2$ (SEQ ID NO: 17), IRIKIRIKIRIK-$NH_2$ (SEQ ID NO: 21), irikirik-$NH_2$ (SEQ ID NO: 10), irikirik-$NH_2$ (SEQ ID NO: 18), IRIkIrIK-$NH_2$ (SEQ ID NO: 19), IRVKIRVKIRVK-$NH_2$ (SEQ ID NO: 22), and irvkirvkirvk-$NH_2$ (SEQ ID NO: 23), wherein small underlined residues represent D-amino acids while capital non-underlined represent L-amino acid.

In another aspect, there is provided an amphiphilic peptide for treating keratitis in a subject, wherein the peptide comprises: $(X_1Y_1X_2Y_2)_n$ (Formula I), wherein the C-terminal end of the peptide is amidated; $X_1$ and $X_2$ is independently of each other a hydrophobic amino acid $Y_1$ and $Y_2$ is independently of each other a cationic amino acid; and n is at least 1.5, wherein the peptide is capable of self-assembly into β-sheet structure.

The inventors of the present disclosure found that the amphiphilic peptide as disclosed in the present disclosure may be used as a broad range antimicrobial agent that may be used to treat keratitis caused by microbes. As used herein, the term "microbes" or "microorganism" is used in its broadest sense and is therefore not limited in scope to prokaryotic organisms. Rather, the term "microorganism" includes within its scope bacteria, archaea, virus, yeast, fungi, protozoa and algae. Thus, in one example, the keratitis as disclosed in the present disclosure is a fungal keratitis, a viral keratitis or a bacterial keratitis.

In one example, the bacteria may be gram positive or gram negative bacteria. Thus, bacterial infections that may be treated include, but not limited to, those caused by bacteria from the genus of *Acetobacter, Acinetobacter, Actinomyces, Agrobacterium* spp., *Azorhizobium, Azotobacter, Anaplasma* spp., *Bacillus* spp., *Bacteroides* spp., *Bartonella* spp., *Bordetella* spp., *Borrelia, Brucella* spp., *Burkholderia* spp., *Calymmatobacterium, Campylobacter, Chlamydia* spp., *Chlamydophila* spp., *Clostridium* spp., *Corynebacterium* spp., *Coxiella, Ehrlichia, Enterobacter, Enterococcus* spp., *Escherichia, Francisella, Fusobacterium, Gardnerella, Haemophilus* spp., *Helicobacter, Klebsiella, Lactobacillus* spp., *Lactococcus, Legionella, Listeria, Methanobacterium extroquens, Microbacterium multiforme, Micrococcus luteus, Moraxella catarrhalis, Mycobacterium* spp., *Mycoplasma* spp., *Neisseria* spp., *Pasteurella* spp., *Peptostreptococcus, Porphyromonas, Pseudomonas, Rhizobium, Rickettsia* spp., *Rochalimaea* spp., *Rothia, Salmonella* spp., *Serratia, Shigella, Staphylococcus* spp., *Stenotrophomonas, Streptococcus* spp., *Treponema* spp., *Vibrio* spp., *Wolbachia*, and *Yersinia* spp. In one example, the bacteria may include, but are not limited to *Acetobacter aurantius, Acinetobacter baumannii, Actinomyces Israelii, Agrobacterium radiobacter, Agrobacterium tumefaciens, Azorhizobium caulinodans, Azotobacter vinelandii, Anaplasma phagocytophilum, Anaplasma marginale, Bacillus anthracis, Bacillus brevis, Bacillus cereus, Bacillus fusiformis, Bacillus licheniformis, Bacillus megaterium, Bacillus mycoides, Bacillus stearothermophilus, Bacillus subtilis, Bacteroides fragilis, Bacteroides gingivalis, Bacteroides melaminogenicus (Prevotella melaminogenica), Bartonella henselae, Bartonella quintana, Bordetella bronchiseptica, Bordetella pertussis, Borrelia burgdorferi, Brucella abortus, Brucella melitensis, Brucella suis, Burkholderia mallei, Burkholderia pseudomallei, Burkholderia cepacia* complex, *Burkholderia cenocepacia, Calymmatobacterium granulomatis, Campylobacter coli, Campylobacter fetus, Campylobacter jejuni, Campylobacter pylori, Chlamydia trachomatis, Chlamydophila.* (such as *C. pneumoniae, Chlamydophila psittaci, Clostridium botulinum,*

*Clostridium difficile, Clostridium perfringens, Clostridium tetani), Corynebacterium diphtheriae, Corynebacterium fusiforme, Coxiella bumetii, Ehrlichia chaffeensis, Enterobacter cloacae, Enterococcus avium, Enterococcus durans, Enterococcus faecalis, Enterococcus faecium, Enterococcus galllinarum, Enterococcus maloratus, Escherichia coli, Francisella tularensis, Fusobacterium nucleatum, Gardnerella vaginalis, Haemophilus ducreyi, Haemophilus influenzae, Haemophilus parainfluenzae, Haemophilus pertussis, Haemophilus vaginalis, Helicobacter pylori, Klebsiella pneumoniae, Lactobacillus acidophilus, Lactobacillus casei, Lactococcus lactis, Legionella pneumophila, Listeria monocytogenes, Methanobacterium extroquens, Microbacterium multiforme, Micrococcus luteus, Moraxella catarrhalis, Mycobacterium avium, Mycobacterium bovis, Mycobacterium diphtheriae, Mycobacterium intracellulare, Mycobacterium leprae, Mycobacterium lepraemurium, Mycobacterium phlei, Mycobacterium smegmatis, Mycobacterium tuberculosis, Mycoplasma fermentans, Mycoplasma genitalium, Mycoplasma hominis, Mycoplasma penetrans, Mycoplasma pneumoniae, Neisseria gonorrhoeae, Neisseria meningitidis, Pasteurella multocida, Pasteurella tularensis Peptostreptococcus, Porphyromonas gingivalis, Pseudomonas aeruginosa, Rhizobium Radiobacter, Rickettsia prowazekii, Rickettsia psittaci, Rickettsia quintana, Rickettsia rickettsii, Rickettsia trachomae, Rochalimaea henselae, Rochalimaea quintana, Rothia dentocariosa, Salmonella enteritidis, Salmonella typhi, Salmonella typhimurium, Serratia marcescens, Shigella dysenteriae, Staphylococcus aureus, Staphylococcus epidermidis, Stenotrophomonas maltophilia, Streptococcus agalactiae, Streptococcus. avium, Streptococcus bovis, Streptococcus cricetus, Streptococcus faceium, Streptococcus faecalis, Streptococcus ferus, Streptococcus gallinarum, Streptococcus lactis, Streptococcus mitior, Streptococcus mitis, Streptococcus mutans, Streptococcus oralis, Streptococcus pneumoniae, Streptococcus pyogenes, Streptococcus rattus, Streptococcus salivarius, Streptococcus sanguis, Streptococcus sobrinus, Treponema pallidum, Treponema denticola, Vibrio cholerae, Vibrio comma, Vibrio parahaemolyticus, Vibrio vulnificus, Wolbachia, Yersinia enterocolitica, Yersinia pestis* and *Yersinia pseudotuberculosis*. In one example, the bacteria may include, but is not limited to *Escherichia coli, Staphylococcus epidermidis, Staphylococcus aureus, Enterococcus* spp., *Klebsiella pneumoniae, Acinetobacter baumanni, Pseudomonas aeruginosa* and *Mycobacterium tuberculosis*.

In one example, the bacterial infection may cause conditions such as, but are not limited to pneumonia, tuberculosis, meningitis, diarrhoeal diseases, formation of biofilm, sepsis, listeriosis, gastroenteritis, toxic shock syndrome, hemorrhagic colitis; hemolytic uremic syndrome, Lyme Disease, gastric and duodenal ulcers, human ehrlichiosis, pseudomembranous colitis, cholera, salmonellosis, cat scratch fever, necrotizing fasciitis (GAS), streptococcal toxic shock syndrome, nosocomial and community associated infections, atherosclerosis, sudden infant death syndrome (SIDS), ear infections, respiratory tract infections, urinary tract infections, skin and soft tissue infections, nail bed infections, wound infection, septicemia, gastrointestinal disease, hospital-acquired endocarditis and blood stream infections. In one example, the bacteria may be drug resistant bacteria.

The amphiphilic peptide as disclosed in the present disclosure may be for treating bacterial keratitis that may be caused by *Pseudomonas aeruginosa, Streptococcus pneumonia, Staphylococcus aureus* or *Staphylococcus epidermidis*.

In one example, the viral infectious diseases may be caused by virus including, but not limited to infections or infectious diseases caused by adenoviruses, herpes viruses, poxviruses, parvoviruses, reoviruses, picornaviruses, togaviruses, orthomyxoviruses, rhabdoviruses, paramyxoviruses, papillomaviruses, retroviruses (such as Human Immunodeficiency Virus) and hepadnaviruses. In one example, the viral infectious disease may include, but is not limited to common cold, influenza, chickenpox, cold sores, Ebola, AIDS, avian influenza, SARS, dengue, herpes, shingles, measles, mumps, rubella, rabies, human papillomavirus, viral hepatitis, coxsackie virus, Epstein Barr virus and the like.

The amphiphilic peptide as disclosed in the present disclosure may also be used for treating viral keratitis that may be caused by varicella zoster, adenoviruses, Herpes Simplex Virus-1 (HSV-1).

As used herein, the term "fungi' (and derivatives thereof, such as "fungal infection") includes, but is not limited to, references to organisms (or infections due to organisms) of the following genus: *Absidia, Ajellomyces, Arthroderma, Aspergillus, Blastomyces, Candida, Cladophialophora, Coccidioides, Cryptococcus, Cunninghamella, Epidermophyton, Exophiala, Filobasidiella, Fonsecaea, Fusarium, Geotrichum, Histoplasma, Hortaea, Issatschenkia, Madurella, Malassezia, Microsporum, Microsporidia, Mucor, Nectria, Paecilomyces, Paracoccidioides, Penicillium, Pichia, Pneumocystis, Pseudallescheria, Rhizopus, Rhodotorula, Scedosporium, Schizophyllum, Sporothrix, Trichophyton,* and *Trichosporon*. For example, fungal infections caused by species such as, but is not limited to *Absidia corymbifera, Ajellomyces capsulatus, Ajellomyces dermatitidis, Arthroderma benhamiae, Arthroderma fulvum, Arthroderma gypseum, Arthroderma incurvatum, Arthroderma otae* and *Arthroderma vanbreuseghemii, Aspergillus flavus, Aspergillus fumigatus* and *Aspergillus niger, Blastomyces dermatitidis, Candida albicans, Candida glabrata, Candida guilliermondii, Candida krusei, Candida parapsilosis, Candida tropicalis* and *Candida pelliculosa, Cladophialophora carrionii, Coccidioides immitis* and *Coccidioides posadasii, Cryptococcus neoformans, Cunninghamella Sp, Epidermophyton floccosum, Exophiala dermatitidis, Filobasidiella neoformans, Fonsecaea pedrosoi, Fusarium solani, Geotrichum candidum, Histoplasma capsulatum, Hortaea werneckii, Issatschenkia orientalis, Madurella grisae, Malassezia furfur, Malassezia globosa, Malassezia obtusa, Malassezia pachydermatis, Malassezia restricta, Malassezia slooffiae, Malassezia sympodialis, Microsporum canis, Microsporum fulvum, Microsporum gypseum, Microsporidia, Mucor circinelloides, Nectria haematococca, Paecilomyces variotii, Paracoccidioides brasiliensis, Penicillium marneffei, Pichia anomala, Pichia guilliermondii, Pneumocystis jiroveci, Pneumocystis carinii, Pseudallescheria boydii, Rhizopus oryzae, Rhodotorula rubra, Scedosporium apiospermum, Schizophyllum commune, Sporothnx schenckii, Trichophyton mentagrophytes, Trichophyton rubrum, Trichophyton verrucosum* and *Trichophyton violaceum,* and *Trichosporon asahii, Trichosporon cutaneum, Trichosporon inkin* and *Trichosporon mucoides*. In one example, the fungal infection as described herein may cause by *C. albicans*. In one example, the fungal infection may be caused by a drug resistant fungus. Exemplary use of the peptides as described herein for inhibiting, treating or removing fungus is provided in Tables 2 and 4.

The inventors of the present disclosure also found the amphiphilic peptide as disclosed herein may be used for treating fungal keratitis that may be caused by filamentous and/or yeast-like fungi. In one example, the yeast-like fungi may be *Candida albicans*. In another example, the filamentous fungi may include *Aspergillus flavus, Aspergillus fumigatus, Fusarium* spp., *Alternaria* spp., and *Paecilomyces lilacinus*.

Sepsis refers to the major cause of mortality in intensive care units worldwide, which is triggered by the release of lipopolysaccharide molecules from the outer wall of gram-negative bacteria. Currently, besides the intravenous administration of broad spectrum antibiotics, only supportive therapies are given to prevent the aggravation of septic shock syndrome, with no effective therapies against the microbial endotoxin, which is a noxious mediator of immune responses. Polymyxin B is the 'gold' standard for endotoxin binding and neutralization, however, its high cytotoxicity negates its practical applicability for systemic applications. As such, there is a need to provide an alternative antimicrobial agent that can simultaneously annihilate causative microorganisms and neutralize endotoxins without having cytotoxic activity towards the mammalian cells. Thus, in one example, the peptide of the present disclosure may be used for preventing sepsis.

Figure 9:
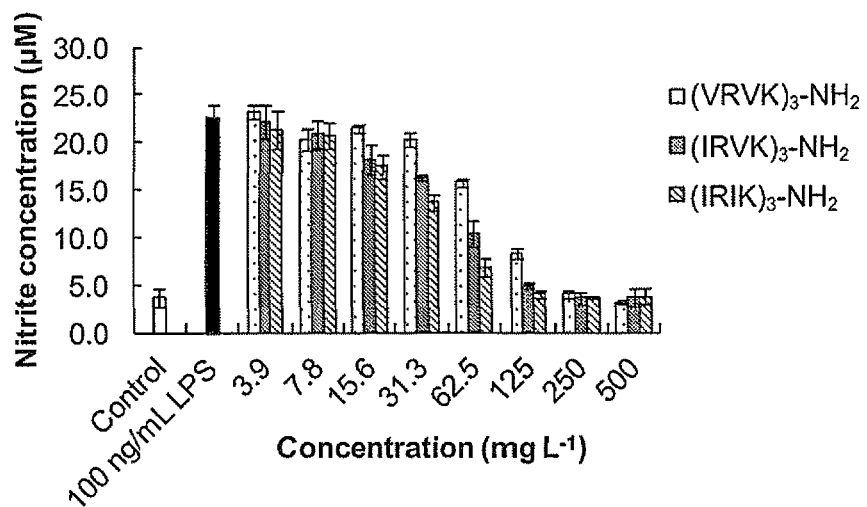
FIG. 9 shows the inhibitory effects of the peptides of the present disclosure on LPS-stimulated NO production in NR8383 rat macrophage cell line.

The lipopolysaccharide (LPS) endotoxin, which has potent immunostimulating properties, is an integral structural component in the outer membrane leaflet of Gram-negative bacteria. LPS is shed continuously during microbial cell growth and division and is liberated in large amounts during cell death, often as a result of antibiotics therapies against bacterial infections. Upon release into the bloodstream, LPS aggregates are dissociated by LPS-binding plasma proteins (LBPs) to form LPS-LBP complexes which stimulate the host monocytes and macrophages to secrete various cytokines (e.g. TNF-α, IL-6, IL-8) and pro-inflammatory mediators (e.g. NO and reactive oxygen species). This activation of the innate immune system triggers a cascade of exaggerated immune responses resulting in a serious clinical syndrome known as septic shock, which could rapidly precipitate in multiple organ failure or death if left untreated. The anionic amphiphilic lipid A domain, which is structurally conserved across most Gram-negative genera, is well-regarded as the active moiety of LPS. The inventors of the present disclosure demonstrates that cationic antimicrobial peptide amphiphiles as described herein present a particularly useful candidate for binding and neutralizing of LPS via electrostatic interactions with the anionic head group by cationic lysine or arginine residues, and dissociation of LPS aggregates via hydrophobic interactions between the alkyl chains of LPS and non-polar amino acid side chains. In one example, there is provided a method of neutralizing endotoxins comprising administration of a pharmaceutically effective amount of a peptide of the present disclosure. In one example, the endotoxins may be bacterial endotoxins or fungal endotoxins. In one example, the endotoxins may be polysaccharides, lipoteichoic acid, lipopolysaccharide or lipooligosaccharide. FIG. 9 demonstrates that the peptides of the present disclosure effectively reduce the effects of LPS on macrophages.

Another problem that bacteria may pose towards human is the formation of biofilms. The formation of biofilms is a significant problem that is implicated in a variety of both the medical field and the non-medical field. Biofilm formation occurs when microbial cells adhere to each other and are embedded in a matrix of extracellular polymeric substance (EPS) on a surface. The growth of microbes in such a protected environment that is enriched with biomacromolecules (e.g. polysaccharides, nucleic acids and proteins) and nutrients allow for enhanced microbial cross-talk and increased virulence. As a result, physiological and phenotypic changes particularly in the growth rate and gene transcription patterns of the microbes entrapped within the biofilm have been widely described. The inability of antibiotics to traverse the extracellular polymeric substance and/or inactivation of antibiotics by components of the extracellular polymeric substance is believed to be responsible for the ineffectiveness of antibiotics to inhibit or kill biofilm microbes at conventional doses. This phenomenon, coupled with the upregulation of drug resistance genes, often leads to the rapid development of antibiotic resistance in biofilms, making their successful eradication an immense challenge in the medical setting. Thus, there is a need to provide a method of removing biofilm.

In view of the above, in another aspect, there is provided a method of removing a biofilm comprising administration of a pharmaceutically effective amount of the peptide of the present disclosure. In one example, the biofilm may occur on surfaces. The term "surface" used herein, refers to any surface whether medical or industrial, that provides an interface between a fluid, such as a liquid or air, and a solid. The interface between fluid and solid can be intermittent, and can be caused by flowing or stagnant fluid, aerosols, or other means for air-borne fluid exposure. A surface refers, in some examples, to a plane whose mechanical structure is compatible with the adherence of bacteria or fungi. In the context of the peptides and methods described herein, the terminology "surface" encompasses the inner and outer aspects of various instruments and devices, both disposable and non-disposable, medical and non-medical. Examples of non-medical uses include the hull of a ship, dockyard, food processors, mixers, machines, containers, water tanks, water filtrations, purification systems, preservatives in food industries, personal care products such as shampoo, cream, moisturizer, hand sanitizer, soaps and the like. Examples of medical uses include the entire spectrum of medical devices. Such "surfaces" may include the inner and outer aspects of various instruments and devices, whether disposable or intended for repeated uses. Examples include the entire spectrum of articles adapted for medical use, including scalpels, needles, scissors and other devices used in invasive surgical, therapeutic or diagnostic procedures; implantable medical devices, including artificial blood vessels, catheters and other devices for the removal or delivery of fluids to patients, artificial hearts, artificial kidneys, orthopaedic pins, plates and implants; catheters and other tubes (including urological and biliary tubes, endotracheal tubes, peripherally insertable central venous catheters, dialysis catheters, long term tunnelled central venous catheters, peripheral venous catheters, short term central venous catheters, arterial catheters, pulmonary catheters, Swan-Ganz catheters, urinary catheters, peritoneal catheters), urinary devices (including long term urinary devices, tissue bonding urinary devices, artificial urinary sphincters, urinary dilators), shunts (including ventricular or arterio-venous shunts); prostheses (including breast implants, penile prostheses, vascular grafting prostheses, heart valves, artificial joints, artificial larynxes, otological implants), vascular catheter ports, wound drain tubes, hydrocephalus shunts, pacemakers and implantable defibrillators, dental implants, fillings, dentures and the like. Other examples will be readily apparent to practitioners in these arts. Surfaces found in the medical environment also include the inner and outer aspects of pieces of medical equipment, medical gear worn or carried by personnel in the health care setting. Such surfaces can include counter tops and fixtures in areas used for medical procedures or for preparing medical apparatus, tubes and canisters used in respiratory treatments, including the administration of oxygen, of solubilised drugs in nebulisers and of aesthetic agents. Also included are those surfaces intended as biological barriers to infectious organisms in medical settings, such as gloves, aprons and face-shields. Commonly used materials for biological barriers may be latex-based or non-latex based. An example for a non-latex based biological barrier material may include vinyl. Other such surfaces can include handles and cables for medical or dental equipment not intended to be sterile. Additionally, such surfaces can include those non-sterile external surfaces of tubes and other apparatus found in areas where blood or body fluids or other hazardous biomaterials are commonly encountered. In one example, the biofilm may be comprised on catheters and medical implants.

In another aspect, there is provided a use of a peptide of the present disclosure in the manufacture of a medicament for treating keratitis in a subject in need thereof. The terms "treat," "treatment," and grammatical variants thereof, refer to both therapeutic treatment and prophylactic or preventative measures, wherein the object is to prevent or slow down (lessen) an undesired physiological condition, disorder or disease or obtain beneficial or desired clinical results. Such beneficial or desired clinical results include, but are not limited to, alleviation of symptoms; diminishment of extent of condition, disorder or disease; stabilized (i.e. not worsening) state of condition, disorder or disease; delay or slowing of condition, disorder or disease progression; amelioration of the condition, disorder or disease state, remission (whether partial or total), whether detectable or undetectable; or enhancement or improvement of condition, disorder or disease. Treatment includes eliciting a cellular response that is clinically significant, without excessive levels of side effects. Treatment also includes prolonging survival as compared to expected survival if not receiving treatment.

In view of the above, in another aspect, there is provided a method of removing a biofilm from a cornea in a subject comprising administration of a pharmaceutically effective amount of the peptide of the present disclosure.

The terms "decrease", "reduced", "reduction", "decrease", "removal" or "inhibit" are all used herein generally to mean a decrease by a statistically significant amount. However, for avoidance of doubt, "reduced", "reduction" or "decrease", "removal", or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level (e.g., in the absence of a peptide as described herein).

The inventors of the present disclosure also found that the peptides as described herein may induce cell death in cancerous cell lines. Thus, in another aspect, there is provided a method of treating proliferative diseases may comprise administration of a pharmaceutically effective amount of a peptide as described herein. In one example, the proliferative diseases may include, but are not limited to tumour, cancer, malignancy or combinations thereof. In one example, the proliferative diseases may include, but are not limited to of colorectal cancer, fibrosarcoma, myxosarcoma, liposarcoma, chondrosarcoma, osteogenic sarcoma, chordoma, angiosarcoma, endothelio sarcoma, lymphangiosarcoma, lymphangio-endotheliosarcoma, synovioma, mesothelioma, Ewing's tumour, leiomyosarcoma, rhabdomyosarcoma, colon carcinoma, gastric cancer, pancreatic cancer, breast cancer, ovarian cancer, prostate cancer, squamous cell carcinoma of the head and neck, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, liver metastases, bile duct carcinoma, choriocarcinoma, seminoma, embryonal carcinoma, thyroid carcinoma such as anaplastic thyroid cancer, Wilms' tumour, cervical cancer, testicular tumour, lung cancer, small cell cancer of the lung, non-small cell cancer of the lung, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. Exemplary use of the peptides as described herein for inducing cancerous cell death is provided in FIG. 22.

In another aspect, there is provided the use of a peptide of the present disclosure in the manufacture of a medicament for treating bacterial infection, or removing bacteria, or neturalising endotoxins, or treating viral based infectious diseases or treating a fungal infection or infestations, or removing fungus or treating proliferative diseases. In one example, the use may further comprise providing the peptide of the present disclosure for administration into a subject in need thereof. In one example, wherein the medicament is to be administered into a subject in need thereof.

In one example, the subject or patient may be an animal, mammal, human, including, without limitation, animals classed as bovine, porcine, equine, canine, lupine, feline, murine, ovine, avian, piscine, caprine, corvine, acrine, or delphine. In one example, the patient may be a human.

In one example, the peptide as described herein may be provided as a composition or a pharmaceutical composition. The compositions as described herein may be administered in a number of ways depending upon whether local or systemic treatment is desired. Administration may be topical, pulmonary (e.g., by inhalation or insufflation of powders or aerosols, including by nebulizer; intratracheal, intranasal, epidermal and transdermal) or systemic such as oral, and/or parenteral. Parenteral administration includes intravenous, intraarterial, subcutaneous, intraperitoneal or intramuscular injection or infusion; or intracranial, e.g., intrathecal or intraventricular, administration. In one example, the route of administration may be selected from the group consisting of systemic administration, oral administration, intravenous administration and parenteral administration.

As the present disclosure relates to the treatment of ocular keratitis, in one example, the composition may be administered for local treatment. Accordingly, in the example, the composition may be provided as composition for topical administration such as eye drops, creams, foams, gels, lotions and ointments.

As the present disclosure relates to the treatment of ocular keratitis, in one example, the composition may be administered for local or topical treatment. Compositions and formulations for topical administration may include sterile aqueous solutions that may also contain buffers, diluents and other suitable additives such as, but not limited to, penetration enhancers, carrier compounds and other pharmaceutically acceptable carriers or excipients.

Compositions as described herein include, but are not limited to, solutions, pastes, ointment, creams, hydrogels, emulsions, liposome-containing formulations, foams, eye drops and coatings. These compositions may be generated from a variety of components that include, but are not limited to, preformed liquids, self-emulsifying solids and self-emulsifying semisolids.

The formulations as described herein, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions as described herein may be formulated into any of many possible dosage forms including, but not limited to tablets, capsules, liquid syrups, soft gels, suppositories, and enemas. The compositions as described herein may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one example, the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

The compositions as described herein may additionally contain other adjunct components conventionally found in pharmaceutical compositions. Thus, for example, the compositions may contain additional, compatible, pharmaceutically-active materials such as, for example, antipruritic, astringents, local anaesthetics or anti-inflammatory agents, or may contain additional materials useful in physically formulating various dosage forms of the compositions of the present invention, such as buffer, dyes, preservatives, antioxidants, opacifiers, thickening agents and stabilizers or combination thereof appropriate for use with the pharmacologically active agent that may be added to solution in any concentration suitable for use in eye drops. However, such materials, when added, should not unduly interfere with the biological activities of the components of the compositions of the present disclosure. The formulations can be sterilized and, if desired, mixed with auxiliary agents, e.g., lubricants, preservatives, stabilizers, wetting agents, emulsifiers, salts for influencing osmotic pressure, buffers, colourings, flavourings and/or aromatic substances and the like which do not deleteriously interact with the peptide(s) of the formulation.

The term "pharmaceutically effective amount" as used herein includes within its meaning a sufficient but non-toxic amount of the compound as described herein to provide the desired effect, that is, causing a Log reduction in the number of microorganisms of at least 1.0, which means that less than 1 microorganism in 10 remains. The modified peptides of the present disclosure may provide Log reductions in the number of microorganisms of at least about 2.0, or at least about 3.0, or at least about 4.0, or at least about 5.0, or at least about 6.0, or at least about 7.0. The exact amount required will vary from subject to subject depending on factors such as the species being treated, the age and general condition of the subject, the severity of the condition being treated, the particular agent being administered, the mode of administration, and so forth. Thus, it is not possible to specify an exact "effective amount". However, for any given case, an appropriate "effective amount" may be determined by one of ordinary skill in the art using only routine experimentation.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of the composition, and can generally be estimated based on EC50s found to be effective in in vitro and in vivo animal models or based on the examples described herein. In general, dosage is from 16 mg/ml to 5000 mg/ml and may be given once or more daily, weekly, monthly or yearly.

In one example, the protocol for use of the resulting eye drops to treat or to alleviate the symptoms of ocular keratitis may include placing drops in the affected eye 3 times daily until the severity of the symptoms is reduced to an acceptable level. In particularly severe cases, more frequent applications may be necessary, and in less severe cases, a single daily dose may be sufficient.

In one example, the composition may be administered in an amount of between any one of about 1 mg, 1.5 mg, 2 mg, 2.5 mg, 3 mg, 3.5 mg, 4 mg, 5 mg, 10 mg, 11 mg, 12 mg, 13 mg, 14 mg, 15 mg, 16 mg, 17 mg, 18 mg, 19 mg, 20 mg, 25 mg, 30 mg, 35 mg, 40 mg, 45 mg, 50 mg, 75 mg, 100 mg, 125 mg, 150 mg, 175 mg, 200 mg, 225 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg. 1900 mg, 1950 mg, 2000 mg, 2050 mg, 2100 mg, 2150 mg, 2200 mg, 2250 mg, 2300 mg, 2350 mg, 2400 mg, 2450 mg, 2500 mg, 2550 mg, 2600 mg, 2650 mg, 2700 mg, 2750 mg, 2800 mg, 2850 mg, 2900 mg, 2950 mg, 3000 mg, 3050 mg, 3100 mg, 3150 mg, 3200 mg, 3250 mg, 3300 mg, 3350 mg, 3400 mg, 3450 mg, 3500 mg, 3550 mg, 3600 mg, 3650 mg, 3700 mg, 3750 mg, 3800 mg, 3850 mg, 3900 mg, 3950 mg, 4000 mg, 4050 mg, 4100 mg, 4150 mg, 4200 mg, 4250 mg, 4300 mg, 4350 mg, 4400 mg, 4450 mg, 4500 mg, 4550 mg, 4600 mg, 4650 mg, 4700 mg, 4750 mg, 4800 mg, 4850 mg, 4900 mg, 4950 mg, 5000 mg/ml.

In one example, the concentration of the administered composition is about 1 to about 100 mg/Kg of body weight of the patient, about 5 to about 100 mg/Kg of body weight of the patient, about 10 to about 100 mg/Kg of body weight of the patient, about 20 to about 100 mg/Kg of body weight of the patient, about 30 to about 100 mg/Kg of body weight of the patient, about 1 to about 50 mg/Kg of body weight of the patient, about 5 to about 50 mg/Kg of body weight of the patient and about 10 to about 50 mg/Kg of body weight of the patient.

As used herein, the term "about", in the context of amounts or concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

As used herein the term "consisting essentially of" refers to those elements required for a given example. The term permits the presence of additional elements that do not materially affect the basic and novel or functional characteristic(s) of that example of the invention.

The term "consisting of" refers to compositions, methods, and respective components thereof as described herein, which are exclusive of any element not recited in that given example.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Example 1

Investigation into the Antimicrobial Properties of Peptides of the Present Disclosure (L-Peptides)

Materials

Peptides used in this study were synthesized by GL Biochem (Shanghai, China) and purified to more than 95% using analytical reverse phase (RP)—HPLC. The molecular weights of the peptides were further confirmed using matrix-assisted laser desorption/ionization time-of-flight mass spectroscopy (MALDI-TOF MS, Model Autoflex II, Bruker Daltonics Inc., U.S.A.) using α-cyano-4-hydroxycinnamic acid (4-HCCA) as matrix. 4-HCCA was purchased from Sigma-Aldrich (Singapore) and used in saturated acetonitrile/water (1:1 volume ratio) after re-crystallization. Phosphate-buffered saline (10×PBS) was purchased from 1$^{st}$ Base (Singapore) and diluted to the intended concentration before use. Mueller-Hinton Broth II (MHB II) and yeast mould broth (YMB) powders were purchased from BD Diagnostics (Singapore) and re-constituted according to the manufacturer's instructions. *Staphylococcus epidermidis* (ATCC No. 12228), *Staphylococcus aureus* (ATCC No. 29737), *Escherichia coli* (ATCC No. 25922), *Pseudomonas aeruginosa* (ATCC No. 9027) and yeast *Candida albicans* (ATCC No. 10231) were obtained from ATCC (U.S.A) and cultivated according to the recommended protocols. Lipopolysaccharide (LPS) and FITC-conjugated LPS from *E. coli* 0111:B4 were purchased from Sigma-Aldrich. Griess reagent system was obtained from Promega (U.S.A.) and used according to the manufacturer's protocol.

Circular Dichroism (CD) Spectroscopy

Each peptide was first dissolved at 0.5 mg mL$^{-1}$ in deionized (DI) water alone or DI water containing 25 mM of SDS surfactant. The CD spectra were recorded at room temperature with a CD spectropolarimeter (JASCO Corp. J-810), using a quartz cell with 1.0 mm path length. CD spectra were acquired with solvent subtraction from 190 to 240 nm at 10 nm/min scanning speed and were averaged from 5 runs per peptide sample. The acquired CD spectra were converted to mean residue ellipticity using the following equation:

$$\theta_M = \frac{\theta_{obs}}{10} \cdot \frac{M_{RW}}{c \cdot l}$$

where $\theta_M$ refers to the mean residue ellipticity (deg·cm$^2$·dmol$^{-1}$), $\theta_{obs}$ is the observed ellipticity corrected for DI water at a given wavelength (mdeg), $M_{RW}$ is the residue molecular weight ($M_w$/number of amino acid residues), c is the peptide concentration (mg·mL$^{-1}$), and l is the path length (cm).

Haemolysis Testing

Fresh rat red blood cells were subjected to 25× dilution with PBS to obtain an approximate 4% (by volume) suspension for use in this experiment. 300 μL of red blood cell suspension was added to each tube containing equal volume (300 μL) of peptide solutions in PBS. The tubes were incubated at 37° C. for 1 h before subjected to centrifugation at 1000×g for 5 min. Aliquots (100 μL) of supernatant were transferred to each well of a 96-well plate and analysed for haemoglobin release at 576 nm using a microplate reader (TECAN, Switzerland). Red blood cells suspension incubated with PBS was used as negative control. Absorbance of red blood cells lyzed with 0.1% v/v Triton X-100 was used as the positive control and taken to be 100% haemolytic. Percentage of haemolysis was calculated using the following formula: Haemolysis (%)=[(O.D.$_{576\ nm}$ of treated sample−O.D.$_{576\ nm}$ of negative control)/(O.D.$_{576\ nm}$ of positive control−O.D.$_{576\ nm}$ of negative control)]×100. Data are expressed as mean±standard deviations of 4 replicates.

Minimal Inhibitory Concentration (MIC) Measurements

The antimicrobial activities of the polymers were investigated against Gram-positive *S. epidermidis* and *S. aureus*, Gram-negative *E. coli* and *P. aeruginosa*, and yeast *C. albicans* using the broth microdilution method. Bacterial cells were cultivated in MHBII at 37° C. and yeast cells were grown in YMB at room temperature under constant shaking at 300 rpm to reach mid-logarithmic growth phase. The microbial suspensions were diluted with the appropriate broths and adjusted to give an initial optical density (O.D.) reading of approximately 0.07 at a wavelength of 600 nm on a microplate reader (TECAN, Switzerland), which corresponds to McFarland Standard No. 1 (approximately 3×10$^8$ CFU mL$^{-1}$). Peptides were dissolved in 0.2 μm filtered HPLC grade water and subjected to a series of two-fold dilutions using the appropriate broths. 100 μL of microorganism suspension with an initial loading level of 3×10$^5$ CFU mL$^{-1}$ was added to an equal volume (100 μL) of peptide solution to achieve final concentrations ranging from 3.9 to 500 mg L$^{-1}$ and with water concentration fixed at 10% (by volume) in each well of a 96-well plate. After 18 h or 42 h incubation with shaking at 37° C. or room temperature for bacteria and yeast, respectively, the MIC was taken as the lowest polymer concentration at which no microbial growth was observed visually and there was no change in O.D. readings from 0 h. Microbial cells in broth containing 10% (by volume) of HPLC grade water as well as pure broth alone were used as the negative controls. To ascertain aseptic handling, wells containing pure broth without microbes were included in each experiment. Each test was performed in 6 replicates on at least 2 independent occasions.

Determination of Killing Efficiency

After 18 h treatment of microorganisms with various concentrations of peptides at 0.5×MIC, MIC and 2×MIC, the respective samples were subjected to a series of ten-fold dilutions and plated onto LB agar plates. The plates were then incubated overnight and counted for colony-forming units. A sample containing microbes treated with 10% by volume water was used as a negative control. Results are expressed as Log(CFU/mL) and as % Kill=[(cell count of control−survivor count of polymer-treated microbes)/cell count of control]× 100.

Field Emission-scanning Electron Microscopy (FE-SEM) Imaging

*E. coli* suspension at ~3×10$^8$ CFU ml$^{-1}$ (100 μL) was incubated with an equal volume of broth containing 20% (by volume) of water and a lethal dose (250 mg L$^{-1}$) of a representative peptide in a 96 well-plate for 2 h. Eight replicates of each condition was pooled into a microfuge tube, pelleted down at 5000×g for 5 min, and rinsed twice with PBS. The samples were then fixed with 4% formaldehyde at room temperature for 15 min, followed by rinsing with DI water. Dehydration of the cells was performed using a series of graded ethanol solutions (35, 50, 75, 90, 95 and 100%). The samples were allowed to air-dry, mounted on carbon table, and sputter coated with platinum for imaging with a FE-SEM setup (JEOL JSM-7400F, Japan).

Biofilm Growth Inhibition and Biomass Assay

Overnight cultures of *S. aureus* diluted to 3×10$^6$ CFU ml$^{-1}$ were added into each well of a 96-well plate at a volume of 100 μL per well and allowed to adhere overnight at 37° C. with gentle shaking at 100 rpm. The wells were then rinsed once with 100 μL of PBS to remove planktonic cells and loosely attached cells, and replenished with 100 μL of fresh broth. Biofilm formation was allowed to proceed up to 6-8 days with daily rinsing and media changes before use in experiments. To determine the effects of peptide treatment on viability of *S. aureus* in biofilms, 100 μL of (IRIK)$_2$-NH$_2$ (SEQ ID NO: 17) and (IRVK)$_3$-NH$_2$ (SEQ ID NO: 22) solutions at MIC, 4×MIC and 8×MIC levels were added into each well and allowed to incubate for 24 h. Subsequently, the solutions were removed and 120 μL of activated XTT solution was added into each well. After 4 h incubation, 100 μL aliquots from each well was transferred to a new 96-well plate for the determination of absorbance using a microplate reader (TECAN, Switzerland) at measurement and reference wavelengths of 490 nm and 660 nm, respectively. Relative cell viability was expressed as [(A$_{490}$−A$_{660}$)$_{sample}$/(A$_{490}$−A$_{660}$)$_{control}$]×100%. Data are expressed as mean±standard deviations of four replicates per concentration.

The biomass of the biofilms was estimated by a crystal violet staining assay. Briefly, the formed biofilms were first treated with the peptides for 24 h as described above. After aspirating the culture medium, the biofilms were washed once with PBS, fixed with methanol for 15 min at room temperature and stained with 100 μL of 0.1% (weight by volume) crystal violet for 10 min. The excess crystal violet dye was removed by rinsing the wells with DI water for five times. The dye that is associated with the biofilm was extracted using 100 μL of 33% glacial acetic acid per well and quantified by measuring the absorbance at a wavelength of 570 nm using a microplate reader (TECAN, Switzerland). The relative amount of biomass remaining after peptide treatment was expressed as a percentage of the control treated with broth containing 10% (by volume) of water. Data represent mean±standard deviations of four replicates per concentration.

FITC-LPS Binding Assay

50 μL of 1 μg mL$^{-1}$ in PBS was treated with an equal volume of peptide solution (50 μL) in each well of a black 96-well plate with clear bottom. The interactions of the peptides with the FITC-conjugated LPS were studied by exciting the FITC-LPS at 480 nm and monitoring the emission of FITC at 516 nm in the presence of increasing concentrations of peptides (3.9, 7.8, 15.6, 31.3, 62.5, 125, 250, 500 mg L$^{-1}$) using a fluorescence microplate reader (TECAN, Switzerland) at 0 h and 2 h. 100 μL of PBS containing 10% by volume of water was included as a blank. Fluorescence intensity of 100 μL FITC-LPS (0.5 μg mL$^{-1}$) in PBS was used a negative control. The percentage change in fluorescence intensity was calculated as follows:

$$\% \Delta F(AU) = [((F_{Sample} - F_{Blank})/(F_{Control} - F_{Blank})) \times 100] - 100.$$

Results are expressed as mean±standard deviations of 4 replicates.

Cell Culture

The rat macrophage cell line NR8383 was maintained in FK15 growth medium supplemented with 10% FBS, 100 U mL$^{-1}$ penicillin and 100 mg mL$^{-1}$ streptomycin and cultured at 37° C. under an atmosphere of 5% CO$_2$ and 95% humidified air.

Endotoxin Neutralization Assay

NR8383 cells were plated at a density of 4×10$^4$ and stimulated with LPS (100 ng mL$^{-1}$) from *E. coli* 0111:B4 in the presence (3.9, 7.8, 15.6, 31.3, 62.5, 125, 250, 500 mg L$^{-1}$) or absence of peptides in each well of a 96-well plate for 18 h at 37° C. Untreated cells and cells that were stimulated with LPS alone served as the positive and negative controls, respectively. The amount of NO produced was estimated by quantifying the concentration of the stable NO metabolite nitrite in the isolated supernatant fractions using the Griess reagent (1% sulphanilamide, 0.1% N-1-napthylethylenediamine dihydrochloride, 5% phosphoric acid) according to the manufacturer's protocol. The absorbance was measured at 540 nm and nitrite concentrations were determined using a standard reference curve prepared from known concentrations of NaNO$_2$ solutions.

Cytotoxicity Testing

The rat macrophage cell line NR8383 was seeded at a density of 4×10$^4$ cells per well of a 96-well plate and treated with increasing concentrations of peptides (3.9, 7.8, 15.6, 31.3, 62.5, 125, 250, 500 mg L$^{-1}$) for 18 h at 37 ° C. Subsequently, 20 μL of CELLTITER-BLUE® reagent was added into each well and the plate was incubated for a further 4 h. The fluorescence intensity readings of the wells were determined at excitation wavelength of 560 nm and emission wavelength of 590 nm using a microplate reader. Control wells containing peptide solutions in the absence of cells were included to determine background fluorescence. % Cell viability =[(F$_{treated\ sample}$−F$_{corresponding\ background}$)/(F$_{10\%\ water\ control}$−F$_{10\%\ water\ control\ background}$)]×100. Data are expressed as mean±standard deviations of 4 replicates.

Results

In this study, short amphiphilic peptides containing 8 or 12 amino acid residues were designed by segregating the cationic lysine and/or arginine amino acids in the polar face and various hydrophobic amino acids in the opposite non-polar face. The molecular weights of the synthesized peptides were verified by MALDI-TOF mass spectrometry and the observed molecular weights are listed in Table 1. It can be seen that the experimentally determined molecular weights were in close agreement with the calculated masses, indicating that the products correspond to the designed sequences.

TABLE 1

Synthetic β-sheet forming peptide designs and molecular weight characterizations

| No. of repeat units (n) | Repeat unit | Peptide sequence | SEQ ID NO: | Theoretical $M_w$ | Observed $M_w$[a] |
|---|---|---|---|---|---|
| 2 | VRVK | VRVKVRVK-NH$_2$ | 11 | 982.28 | 984.22 |
|   | IRIR | IRIRIRIR-NH$_2$ | 12 | 1094.42 | 1096.77 |
|   | IKIK | IKIKIKIK-NH$_2$ | 13 | 982.37 | 984.00 |
|   | IRIK | IRIKIRIK-NH$_2$ | 17 | 1038.39 | 1040.16 |
|   | IRVK | IRVKIRVK-NH$_2$ | 14 | 1010.34 | 1012.06 |
|   | FRFK | FRFKFRFK-NH$_2$ | 15 | 1174.46 | 1176.46 |
|   | WRWK | WRWKWRWK-NH$_2$ | 16 | 1330.61 | 1333.59 |
| 3 | VRVK | VRVKVRVKVRVK-NH$_2$ | 20 | 1464.91 | 1467.16 |
|   | IRIK | IRIKIRIKIRIK-NH$_2$ | 21 | 1549.07 | 1551.43 |
|   | IRVK | IRVKIRVKIRVK-NH$_2$ | 22 | 1506.99 | 1510.43 |

[a] Measured by MALDI-TOF MS, apparent $M_w = [M_w + H]^+$

Figure 2:
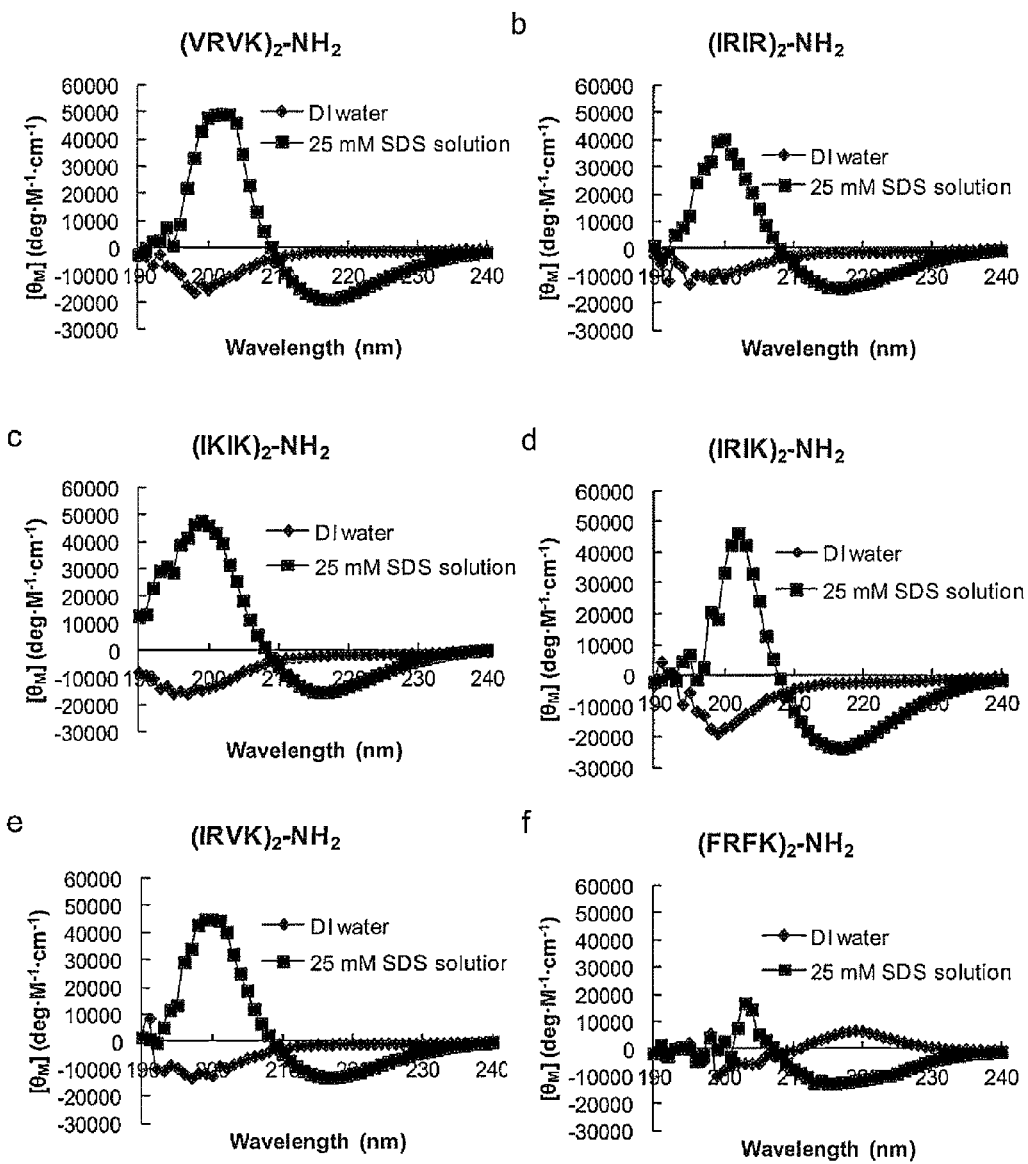
FIG. 2 shows circular dichroism spectra of (a) $(VRVK)_2$-$NH_2$ (SEQ ID NO: 11), (b) $(IRIR)_2$-$NH_2$ (SEQ ID NO: 12), (c) $(IKIK)_2$-$NH_2$ (SEQ ID NO: 13), (d) $(IRIK)_2$-$NH_2$ (SEQ ID NO: 17), (e) $(IRVK)_2$-$NH_2$ (SEQ ID NO: 14), (f) $(FRFK)_2$-$NH_2$ (SEQ ID NO: 15), (g) $(VRVK)_3$-$NH_2$ (SEQ ID NO: 20), (h) $(IRIK)_3$-$NH_2$ (SEQ ID NO: 21), (i) $(IRVK)_3$-$NH_2$ (SEQ ID NO: 22) in deionized water and 25 mM SDS micelles solution.
Figure 2:
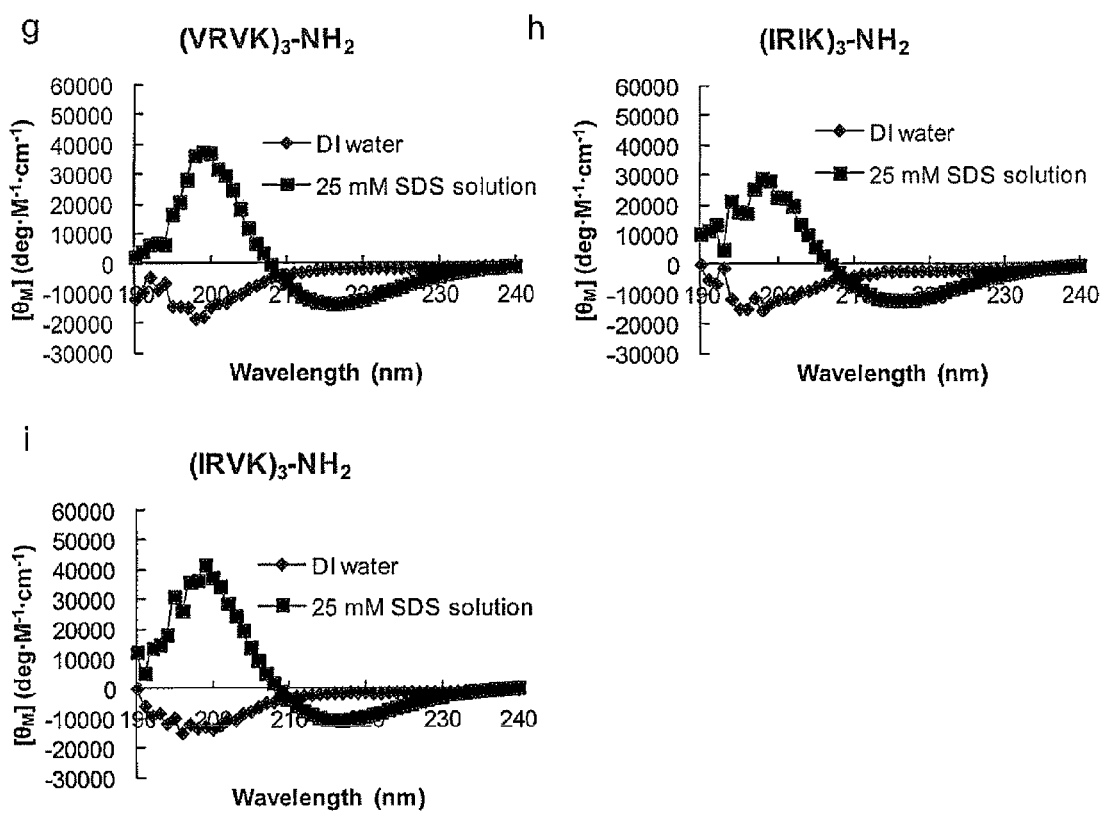

In deionized water, each peptide adopted a random coil structure that is characterized by a minimum at ~195 nm in aqueous solutions due to intermolecular electrostatic repulsion between the protonated lysine and/or arginine residues. Under microbial membrane-mimicking hydrophobic environments (using 25 mM SDS micelles solution), however, the synthetic peptides readily self-assembled into β-sheet secondary structures with characteristic CD spectra showing a maximum at ~200 nm and minimum at ~218 nm (FIG. 2).

The antimicrobial activities of the synthetic peptides were tested against a representative set of clinically relevant microorganisms including Gram-positive *S. epidermidis* and *S. aureus*, Gram-negative *E. coli* and *P. aeruginosa*, and yeast *C. albicans*. As shown in Table 2, the designed peptides displayed broad spectrum antimicrobial activities against the panel of microorganisms tested with geometric mean (GM) minimum inhibitory concentrations (MICs) ranging from 13.3 to 162.7 mg L$^{-1}$. Overall, the peptide (IRIR)$_2$-NH$_2$ (SEQ ID NO: 12) for which all the cationic residues were Arg exhibited the best antimicrobial activities, with the lowest GM MIC value of 13.3 mg L$^{-1}$. This was followed closely by (IRIK)$_2$-NH$_2$ (SEQ ID NO: 17) and (IKIK)$_2$-NH$_2$ (SEQ ID NO: 13), with GM MIC values of 23.4 and 38.3 mg L$^{-1}$, respectively. As can be seen from these results, the peptide with 2 Arg and 2 Lys residues gave rise to antimicrobial effects that were in between its 4 Arg or 4 Lys counterparts. Non-polar amino acids, which are reported to possess high β-sheet forming propensities, were systematically varied based on increasing degree of hydrophobicity and bulkiness while retaining the combination of 2 Arg and 2 Lys cationic residues (Table 1). Among the peptides incorporating Val, Ile, Phe and Trp, (IRIK)$_2$-NH$_2$ (SEQ ID NO: 17) demonstrated the most effective antimicrobial effect against the panel of five microorganisms tested. The replacement of the second hydrophobic Ile residue in the peptide repeat unit with Val to give (IRVK)$_2$-NH$_2$ (SEQ ID NO: 14) resulted in a slight decrease in antimicrobial activities. This result strongly suggests that the Ile residues were essential for the strong antimicrobial effects observed. The antimicrobial effects of the peptides with n=3 repeat units were investigated with sequences containing Val and Ile. From Table 2, (VRVK)$_3$-NH$_2$ (SEQ ID NO: 20) demonstrated the best overall antimicrobial effects, followed by (IRVK)$_3$-NH$_2$ (SEQ ID NO: 22) and (IRIK)$_3$-NH$_2$ (SEQ ID NO: 21). In comparison to the clinically used lipopeptide polymyxin B, several of the β-sheet forming peptides, including (IRIR)$_2$-NH$_2$ (SEQ ID NO: 12), (IKIK)$_2$-NH$_2$ (SEQ ID NO: 13), (IRIK)$_2$-NH$_2$ (SEQ ID NO: 17) and (VRVK)$_3$-NH$_2$ (SEQ ID NO: 20) were found to have a wider spectrum of antimicrobial activities as seen from their lower GM MIC values (13.3-34.6 vs. 41.4).

TABLE 2

Minimum inhibitory concentrations (MICs) and therapeutic indices of synthetic antimicrobial peptides

| SEQ ID NO: | Antimicrobial peptide | MIC (mg L$^{-1}$) | | | | | GM[a] (mg L$^{-1}$) | HO$_{10}$[b] (mg L$^{-1}$) | SI[c] |
|---|---|---|---|---|---|---|---|---|---|
| | | *S. epidermidis* | *S. aureus* | *E. coli* | *P. aeruginosa* | *C. albicans* | | | |
| 11 | (VRVK)$_2$-NH$_2$ | 62.5 | >500 | 250 | >500 | 15.6 | — | >2500 | >10[d] |
| 12 | (IRIR)$_2$-NH$_2$ | 3.9 | 31.3 | 7.8 | 7.8 | 15.6 | 13.3 | 150 | 11.3 |
| 13 | (IKIK)$_2$-NH$_2$ | 2.0 | 125 | 31.3 | 31.3 | 2.0 | 38.3 | 700 | 18.3 |
| 17 | (IRIK)$_2$-NH$_2$ | 3.9 | 62.5 | 15.6 | 31.3 | 3.9 | 23.4 | 1050 | 44.8 |
| 14 | (IRVK)$_2$-NH$_2$ | 7.8 | 250 | 62.5 | 62.5 | 7.8 | 78.1 | >2500 | >32.0 |
| 15 | (FRFK)$_2$-NH$_2$ | 7.8 | 250 | 15.6 | 62.5 | 62.5 | 79.7 | 1600 | 20.1 |
| 16 | (WRWK)$_2$-NH$_2$ | 7.8 | 62.5 | 15.6 | 125 | 250 | 92.2 | 1000 | 10.8 |
| 20 | (VRVK)$_3$-NH$_2$ | 1.0 | 62.5 | 15.6 | 62.5 | 31.3 | 34.6 | >2500 | >72.3 |
| 21 | (IRIK)$_3$-NH$_2$ | 1.0 | 62.5 | 125 | 500 | 125 | 162.7 | 500 | 3.1 |
| 22 | (IRVK)$_3$-NH$_2$ | 2.0 | 31.3 | 15.6 | 62.5 | 125 | 47.3 | 1250 | 26.4 |
| | Polymyxin B | 15.6 | 125 | 2.0 | 2.0 | 62.5 | 41.4 | >2500 | >60.4 |

[a] Geometric mean (GM) of MIC values for the 5 microorganisms tested.
[b] Hemolysis concentration 10% (HC$_{10}$) is defined as the lowest peptide concentration that induces ≥10% hemolysis.
[c] Selectivity index (SI) is calculated as $\frac{HC_{10}}{GM}$.
[d] Calculated as 2500 divided by 250 mg L$^{-1}$.

Figure 3:
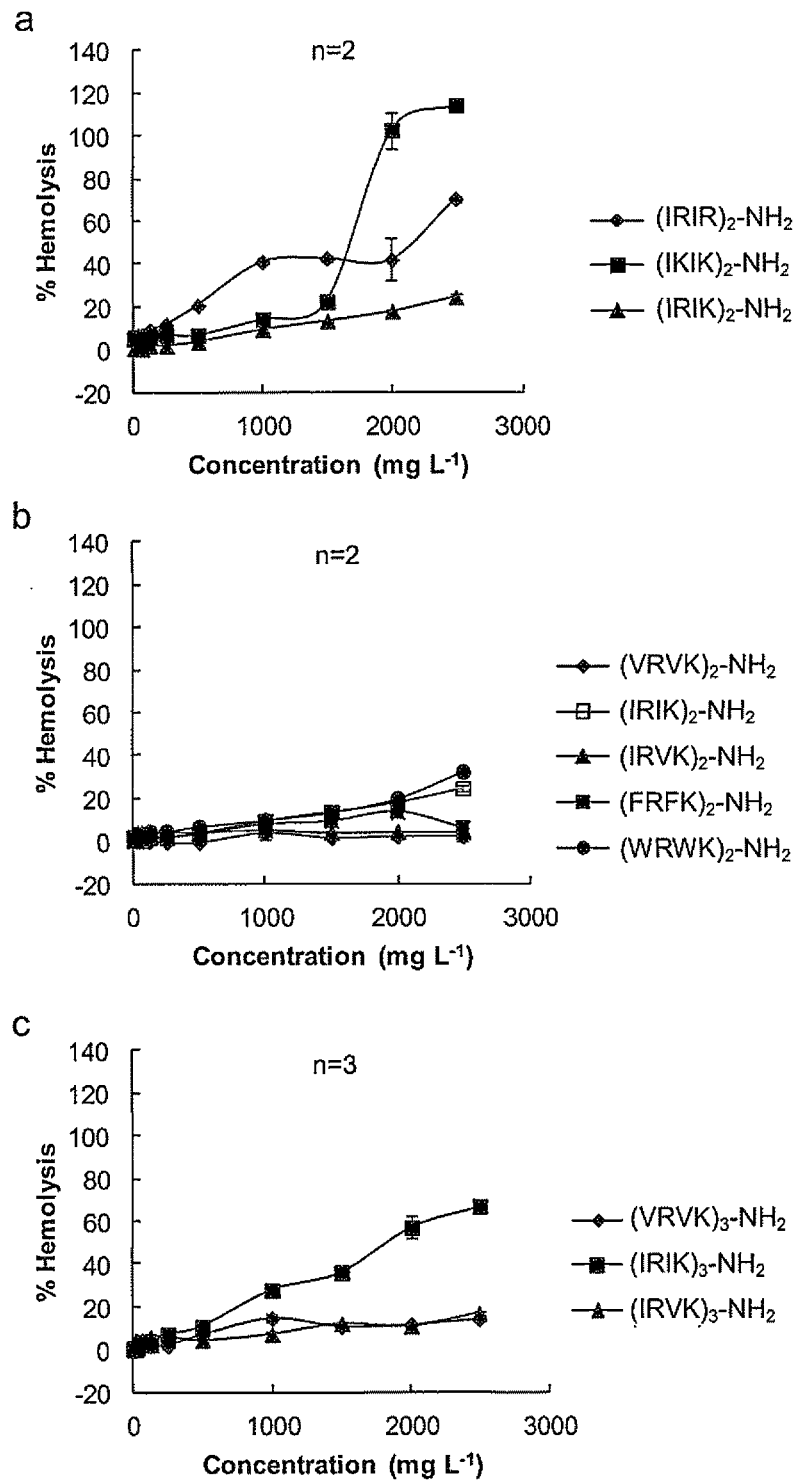
FIG. 3 shows haemolytic activities of the synthetic antimicrobial peptides.

For the β-sheet forming peptides to qualify as suitable therapeutic candidates, their antimicrobial activities should be considered in the light of their selectivity for microbial cell membranes so as to minimize toxicities towards mammalian cells. As shown in FIG. 3, the synthetic peptides induced minimal or no haemolysis against rat red blood cells at various MIC values. The selectivity indices (SIs) of the peptides were further evaluated as a comparison of the safety and efficacies of the different peptide sequences (Table 2). SIs of the various peptides were calculated as the ratio of the $HC_{10}$ value (defined as the lowest peptide concentration that induces 10% or more haemolysis) to the GM (geometric mean MICs of the 5 microbial strains tested). With the exception of $(IRIK)_3$-$NH_2$ (SEQ ID NO: 21), all of the peptides tested were found to have high SIs of greater than 10, indicating that they are highly attractive candidates suitable for both external and systemic applications in the body. In particular, the present disclosure showed the combination of both Arg and Lys residues in $(IRIK)_2$-$NH_2$ (SEQ ID NO: 17) led to marked improvements in the SI from 11.3 and 18.3 of the single cationic amino acid peptide sequences $(IRIR)_2$-$NH_2$ (SEQ ID NO: 12) and $(IKIK)_2$-$NH_2$ (SEQ ID NO: 13), respectively to a value of 44.8. The acute in vivo toxicity testing was performed via intravenous tail vein injection of solutions containing representative peptides of n=2 [$(IRIK)_2$-$NH_2$ (SEQ ID NO: 17)] and n=3 [$(IRVK)_3$-$NH_2$ (SEQ ID NO: 22)] repeat units in mice. The former was selected due to its superior SI among peptides with n=2 repeat units, while the latter was chosen due to its better antimicrobial activities, selectivities and endotoxin neutralization properties (to be discussed later) among peptides with n=3 repeat units. $(IRIK)_2$-$NH_2$ (SEQ ID NO: 17) and $(IRVK)_3$-$NH_2$ (SEQ ID NO: 22) were respectively found to have lethal dose, 50% (LD50; dose required to kill 50% of mice after a specific test period) values of 35.2 mg/kg. The LD50 values of the designed peptides contrast favorably with that reported for polymyxin B (5.4 mg/kg) and gramicidin (1.5 mg/kg).

Figure 4:
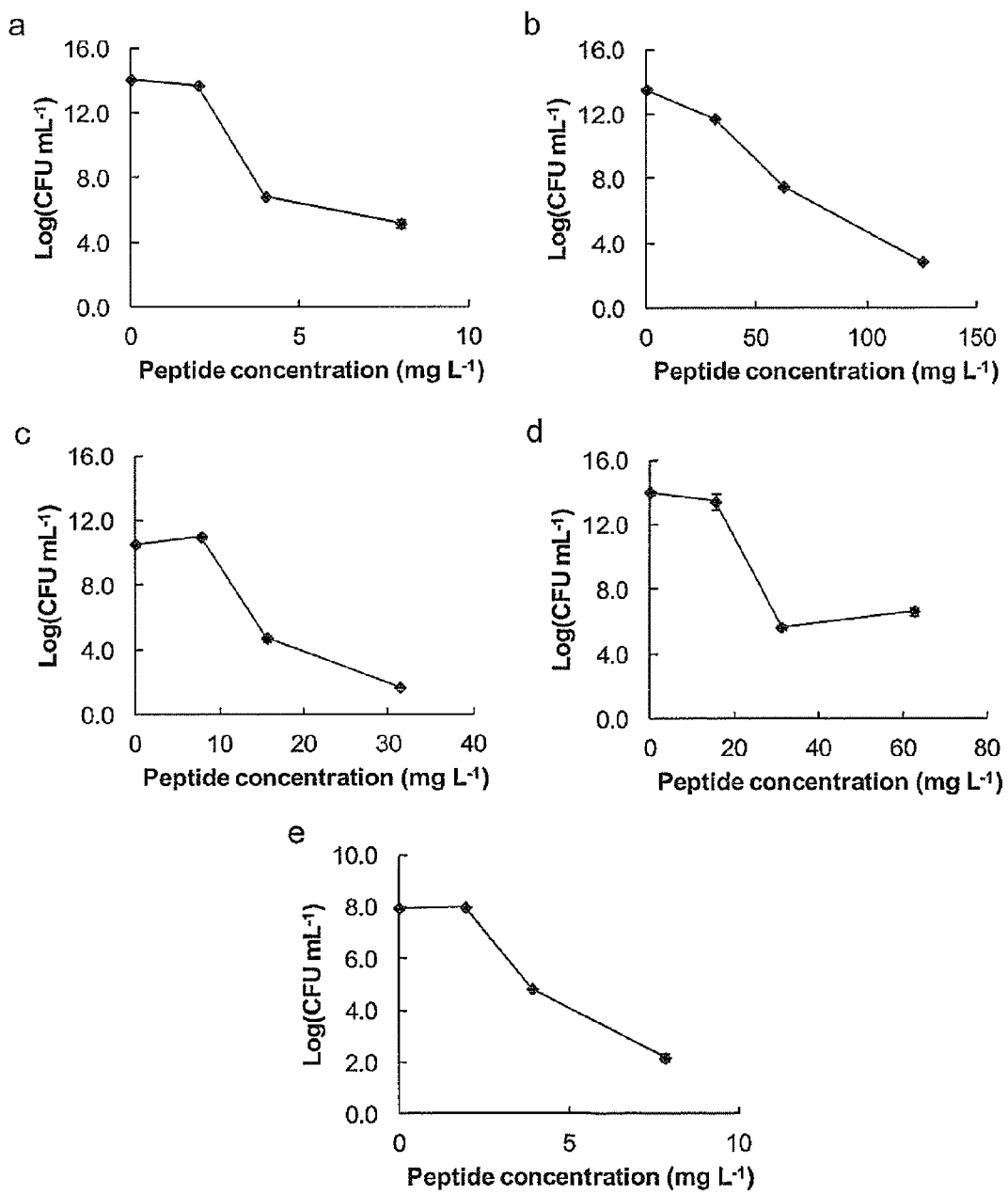
FIG. 4 shows plot of viable microbe colony-forming units (CFU) after treatment with representative peptide $(IRIK)_2$-$NH_2$ (SEQ ID NO: 17) at various concentrations (i.e. 0, 0.5× minimum inhibitory concentration (MIC), MIC and 2×MIC).
Figure 5:
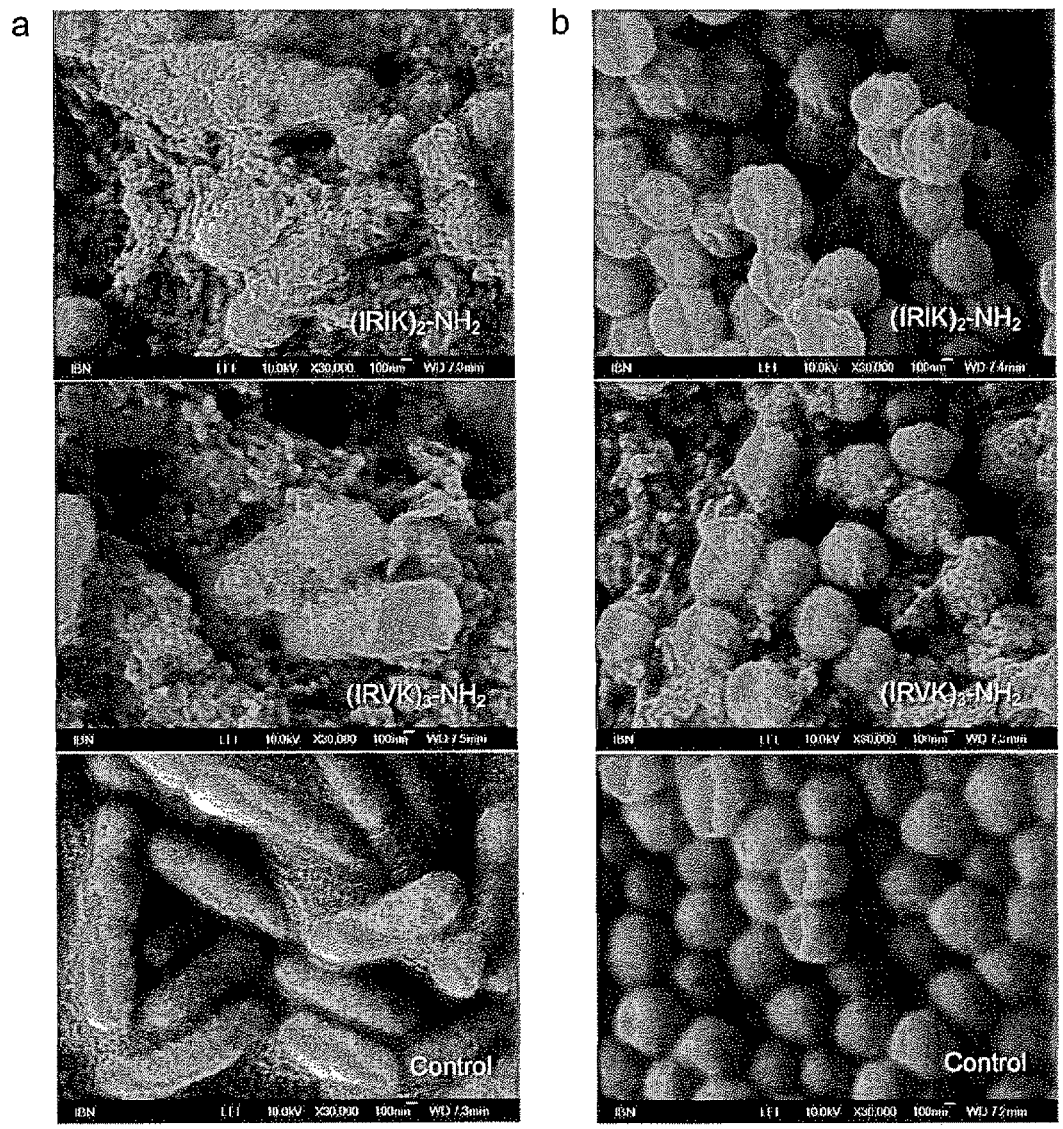
FIG. 5 shows FE-SEM images of (a) *Escherichia coli* and (b) *Staphylococcus aureus* treated with broth containing 10% (by volume) of water as control and representative peptides $(IRIK)_2$-$NH_2$ (SEQ ID NO: 17) and $(IRVK)_3$-$NH_2$ (SEQ ID NO: 22) for 2 h.

To elucidate the antimicrobial mechanism, colony counting experiments were performed after treating the panel of microorganisms with different concentrations of $(IRIK)_2$-$NH_2$ (SEQ ID NO: 17). For each of the five microorganisms tested, the peptide achieved killing efficiencies of close to 100% at the respective MIC values, hence supporting a bactericidal mechanism (FIG. 4). The surface morphology of E. coli after treatment with $(IRIK)_2$-$NH_2$ (SEQ ID NO: 17) and $(IRVK)_3$-$NH_2$ (SEQ ID NO: 22) was investigated under field-emission scanning electron microscopy (FE-SEM). As shown in FIG. 5, the surface of E. coli and S. aureus treated with the peptide appeared rough and uneven as compared to the relatively smooth surface of the control sample treated with broth containing 10% (by volume) of water. This observation is consistent with the membrane lytic mechanism of the various naturally occurring and synthetic AMPs reported in the literature. Compared to conventional antibiotics that inhibit various targets within the biosynthetic pathways of microorganisms, the physical disruption of microbial cell membranes by the peptides is expected to provide an inherent advantage in the clinical setting due to the reduced likelihood for the development of mutations that confer multidrug resistance.

Anti-biofilm Ability

Figure 6:
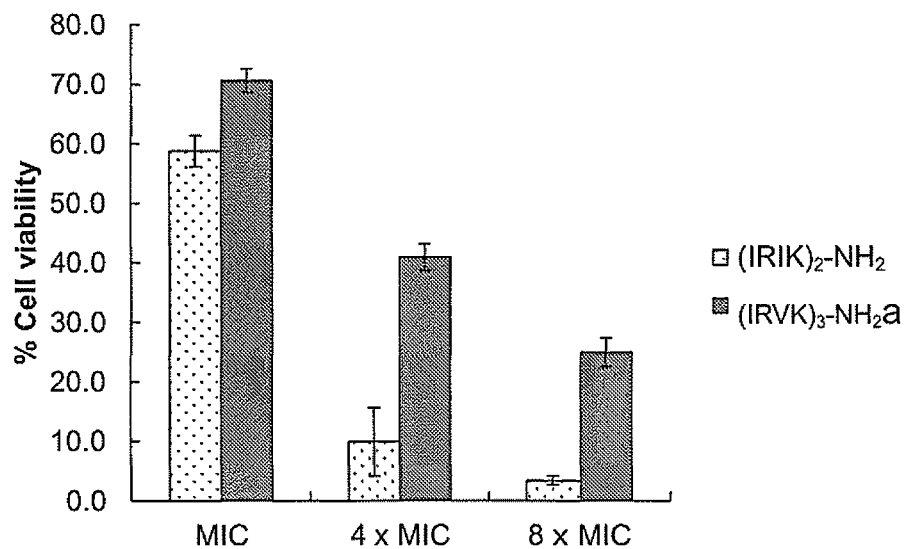
FIG. 6 shows cell viability of *Staphylococcus aureus* in biofilms treated with various concentrations of $(IRIK)_2$-$NH_2$ (SEQ ID NO: 17) and $(IRVK)_3$-$NH_2$ (SEQ ID NO: 22) for 24 h as determined using the XTT assay. *P<0.01 relative to $(IRVK)_3$-$NH_2$.
Figure 7:
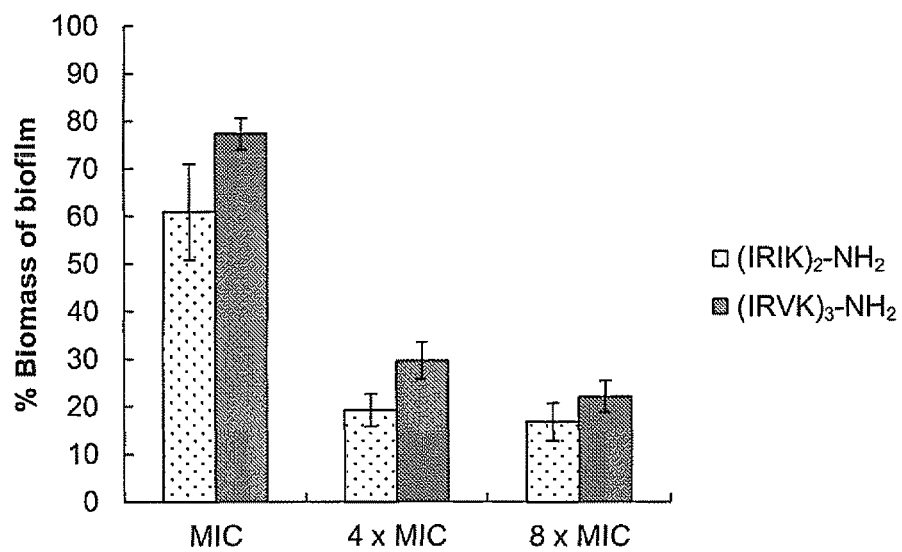
FIG. 7 shows changes in biomass of pre-formed *Staphylococcus aureus* biofilms treated with various concentrations of (IRIK)$_2$-NH$_2$ (SEQ ID NO: 17) and (IRVK)$_3$-NH$_2$ (SEQ ID NO: 22) for 24 h as determined by crystal violet staining.

The anti-biofilm ability of the synthetic antimicrobial peptides on pre-formed biofilms, which is intrinsically more challenging than preventing biofilm formation, was investigated next. As shown in FIG. 6, peptides $(IRIK)_2$-$NH_2$ (SEQ ID NO: 17) and $(IRVK)_3$-$NH_2$ (SEQ ID NO: 22) demonstrated a dose-dependent killing of the S. aureus residing in biofilms. $(IRIK)_2$-$NH_2$ was found to induce significantly higher levels of killing across the three concentrations tested (P<0.01), with cell viability drastically reduced to less than 10% at 4×MIC level within 24 h. To determine the relative amounts of biomass remaining after treatment with the peptides, crystal violet staining and solubilisation of the biofilms were performed. Consistent with the decrease in S. aureus cell viability, the amount of biomass in the treated biofilms was observed to be reduced in a dose-dependent manner (FIG. 7). These results, taken together, provide direct evidence that the 8 and 12 amino acids long peptides are highly effective at killing microbes within biofilms and could efficiently mediate the dispersion of biofilm matrices.

LPS and Endotoxin Neutralisation

Figure 8:
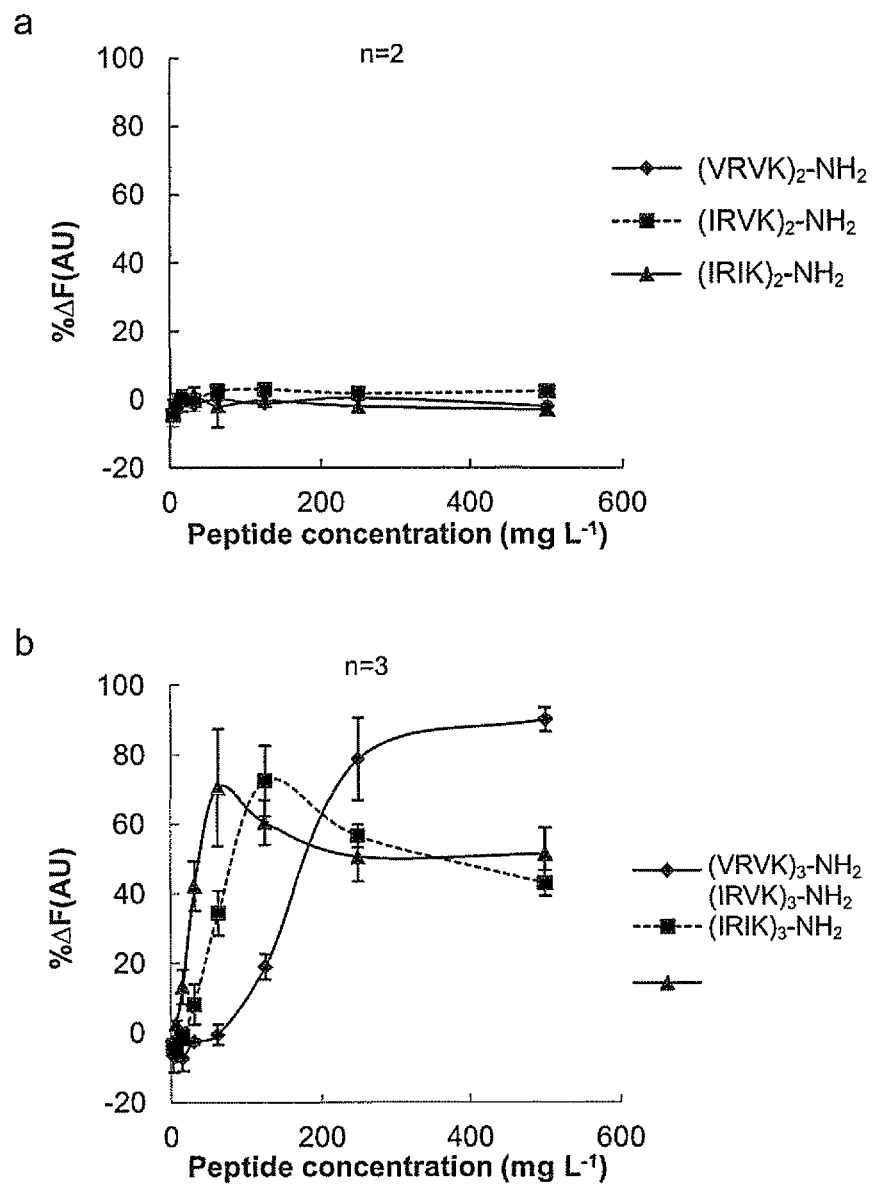
FIG. 8 shows the effects the peptides of the present disclosure with (a) two repeat units (n=2) and (b) three repeat units (n=3) on stability of FITC-labelled LPS aggregates.

In order to evaluate the ability of the synthetic peptides to bind and dissociate LPS aggregates, FITC-conjugated LPS was conjugated with the various peptides and monitored the changes in fluorescent intensities over 2 h. In aqueous solutions, FITC sequestered within LPS aggregates exhibit self-quenching, resulting in low fluorescent intensities. Conversely, when FITC-LPS aggregates dissociate, the fluorescence increases due to a dequenching effect. As seen in FIG. 8a, beta-sheet forming peptides with n=2 did not seem to induce discernible disruption of FITC-LPS aggregates as evident from the lack of changes in fluorescent intensity up to peptide concentrations of 500 mg $L^{-1}$. The corresponding peptides with 3 repeat units, however, produced a strong dose-dependent enhancement of the fluorescent intensities of FITC-LPS (FIG. 8b). Among the three peptide sequences, $(IRIK)_3$-$NH_2$ (SEQ ID NO: 21) and $(IRVK)_3$-$NH_2$ (SEQ ID NO: 22) induced a greater percentage change in fluorescent intensities at lower concentrations, which was followed lastly by $(VRVK)_3$-$NH_2$ (SEQ ID NO: 20).

Figure 10:
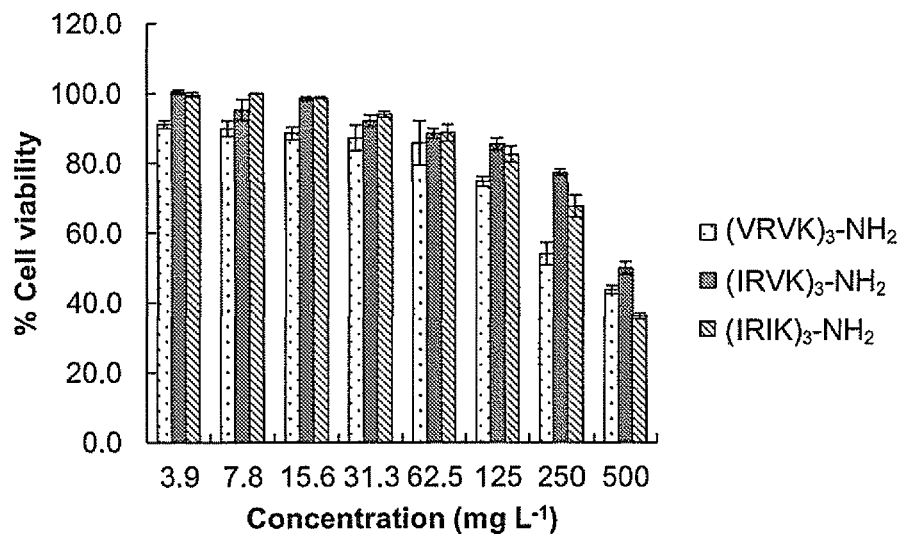
FIG. 10 shows cell viability of NR8383 rat macrophage cell line after 18 h incubation with the peptides of the present disclosure at various concentrations.

The endotoxin neutralizing capabilities of the synthetic peptides was established by estimating the amount of pro-inflammatory nitrogen oxide released via the quantification of the stable NO metabolite nitrite concentration present in the cell culture media after co-incubation of the rat macrophage cell line NR8383 with 100 ng $mL^{-1}$ LPS and the various peptides. The peptides were found to effectively inhibit LPS-stimulated NO production, with significantly decreased nitrite concentrations compared to the non-peptide treated control even at low peptide concentrations of 15.6 mg $L^{-1}$ (FIG. 9). The degree of LPS neutralization mediated by the various peptides was in the order of $(IRIK)_3$-$NH_2$ (SEQ ID NO: 21)>$(IRVK)_3$-$NH_2$ (SEQ ID NO: 22)>$(VRVK)_3$-$NH_2$ (SEQ ID NO: 20), which was in close agreement with the trend observed earlier in the FITC-LPS interaction assay. Importantly, at 125 mg $L^{-1}$ of $(IRIK)_3$-$NH_2$ (SEQ ID NO: 21) and $(IRVK)_3$-$NH_2$ (SEQ ID NO: 22), the nitrite concentration was reduced to the control level. The cytotoxicities of the peptides was further evaluated against the NR8383 cell line and it was found that the cell viabilities was in excess of 80% up to concentrations of 62.5, 125 and 125 mg $L^{-1}$ for $(VRVK)_3$-$NH_2$ (SEQ ID NO: 20), $(IRVK)_3$-$NH_2$ (SEQ ID NO: 22) and $(IRIK)_3$-$NH_2$ (SEQ ID NO: 21), respectively (FIG. 10). These results confirmed that the good anti-inflammatory properties of the synthetic peptides were independent of their effects on cell viability and that the peptides were not cytotoxic at antimicrobial and anti-inflammatory doses, indicating their suitability for systemic administration. Although $(IRIK)_3$-$NH_2$ (SEQ ID NO: 21) possessed the most potent anti-inflammatory activity among the three peptides, its relatively weak antimicrobial activities (GM MIC value=162.7 mg $L^{-1}$) and lower selectivity index (SI=3.1) suggests that the second best anti-inflammatory peptide $(IRVK)_3$-$NH_2$ (SEQ ID NO: 22), which has a much lower geometric mean MIC value of 47.3 and higher selectivity index of 26.4 (Table 2), is a more suitable candidate for the safe and efficacious treatment of bloodstream infections.

In the present disclosure, the inventors designed a series of short synthetic β-sheet folding peptides based upon the common occurrence of amphipathic dyad repeats in natural β-sheet spanning membrane proteins. The designed β-sheet folding peptides demonstrated broad spectrum antimicrobial activities against Gram-positive *S. epidermidis* and *S. aureus*, Gram-negative *E. coli* and *P. aeruginosa* as well as yeast *C. albicans*. Optimal peptide sequences of n=2 and n=3 repeat units, namely (IRIK)$_2$-NH$_2$ (SEQ ID NO: 17) and (IRVK)$_3$-NH$_2$ (SEQ ID NO: 22), were found to possess high selectivity indices of 44.8 and 26.4, respectively. Acute in vivo toxicity testing in mice revealed higher intravenous LD50 values for the optimal synthetic peptides as compared to the clinically used polymyxin B and gramicidin. Further to the highly efficient killing of planktonic microbes, the synthetic peptides were also demonstrated to be potent inhibitors of bacterial growth in biofilms. Additionally, treatment of the biofilms with the various peptides resulted in a drastic decrease in biomass, indicating that the peptides could effectively translocate through and cause dispersion of the biofilm matrix. Additionally, synthetic peptides with 3 repeat units, including (VRVK)$_3$-NH$_2$ (SEQ ID NO: 20), (IRVK)$_3$-NH$_2$ (SEQ ID NO: 22) and (IRIK)$_3$-NH$_2$ (SEQ ID NO: 21), demonstrated endotoxin binding and neutralizing capabilities with minimal or no cytotoxicities induced at the concentrations required for functional effects. Taken together, our findings clearly demonstrated that the rationally designed synthetic β-sheet folding peptides are highly selective and have potential for use as broad spectrum antimicrobial agents to overcome the prevalent problem of multidrug resistance in a wide range of bacterial- or fungal-based infectious disease related applications including, but not limited to, the prevention and eradication of therapeutically challenging biofilms on open wounds, catheters or implants and the neutralization of microbial endotoxins for improved treatment of bloodstream infections.

Example 2

Investigation into the Antimicrobial Properties of Peptides of the Present Disclosure (D-Peptides)

Materials

Peptides used in this study were synthesized by GL Biochem (Shanghai, China) and purified to more than 95% using analytical reverse phase (RP)—HPLC. The molecular weights of the peptides were further confirmed using matrix-assisted laser desorption/ionization time-of-flight mass spectroscopy (MALDI-TOF MS, Model Autoflex II, Bruker Daltonics Inc., U.S.A.) using α-cyano-4-hydroxycinnamic acid (4-HCCA) as matrix. 4-HCCA was purchased from Sigma-Aldrich (Singapore) and used in saturated acetonitrile/water (1:1 volume ratio) after re-crystallization. Phosphate-buffered saline (10×PBS) was purchased from 1st Base (Singapore) and diluted to the intended concentration before use. Cation-adjusted Mueller-Hinton broth II (MHB II) and yeast mould broth (YMB) powders were purchased from BD Diagnostics (Singapore) and reconstituted according to the manufacturer's instructions. *Staphylococcus epidermidis* (ATCC No. 12228), *Staphylococcus aureus* (ATCC No. 6538), *Escherichia coli* (ATCC No. 25922), *Pseudomonas aeruginosa* (ATCC No. 9027) and yeast *Candida albicans* (ATCC No. 10231) were obtained from ATCC (U.S.A.) and cultured according to the recommended protocols. Ciprofloxacin, gentamicin sulfate and penicillin G were obtained from Sigma-Aldrich.

Circular Dichroism (CD) Spectroscopy

Each peptide was first dissolved at 0.5 mg mL$^{-1}$ in deionized (DI) water alone or DI water containing 25 mM of SDS surfactant. The CD spectra were recorded at room temperature with a CD spectropolarimeter (JASCO Corp. J-810), using a quartz cell with 1.0 mm path length. CD spectra were acquired with solvent subtraction from 190 to 240 nm at 10 nm min$^{-1}$ scanning speed and were averaged from 5 runs per peptide sample. The acquired CD spectra were converted to mean residue ellipticity using the following equation:

$$\theta_M = \frac{\theta_{obs}}{10} \cdot \frac{M_{RW}}{c \cdot l}$$

where $\theta_M$ refers to the mean residue ellipticity (deg cm$^2$ dmol$^{-1}$), $\theta_{obs}$ is the observed ellipticity corrected for DI water at a given wavelength (mdeg), MRW is the residue molecular weight (Mw·number of amino acid residues$^{-1}$), c is the peptide concentration (mg mL$^{-1}$), and l is the path length (cm).

Minimal Inhibitory Concentration (MIC) Measurements

The antimicrobial activities of the β-sheet forming peptides were investigated against *S. epidermidis* and *S. aureus* (Gram-positive), *E. coli* and *P. aeruginosa* (Gram-negative), and *C. albicans* (yeast) using the broth microdilution method. Prior to the experiment, bacteria cells were cultivated in MHB II at 37° C. and yeast cells were grown in YMB at room temperature under constant shaking at 300 rpm overnight to reach mid-logarithmic growth phase. The microbial suspensions were diluted with the appropriate broths and adjusted to give an initial optical density (O.D.) reading of approximately 0.07 at a wavelength of 600 nm on a microplate reader (TECAN, Switzerland). The O.D. reading corresponds to McFarland Standard No. 1 (approximately 3×10$^8$ CFU mL$^{-1}$). The peptides were dissolved in HPLC grade water and subjected to a series of two-fold dilutions using the appropriate broths. Subsequently, 100 μL of microorganism suspension with an initial loading level of 3×10$^5$ CFU mL$^{-1}$ was added to an equal volume (100 μL) of polymer solutions to achieve final polymer concentrations ranging from 3.9-500 mg L$^{-1}$ and with water content fixed at 10% (by volume) in each well of a 96-well plate. After 18 h incubation with shaking at 37° C. or room temperature, the MIC was taken as the lowest polymer concentration at which no microbial growth was observed visually and with no change in O.D. readings from 0 h. Microbial cells in broth containing 10% (by volume) water as well as pure broth alone were used as the negative controls. To ensure aseptic handling, wells containing pure broth without microbes were included in each experiment. Each test was performed in 6 replicates on at least 2 independent occasions.

Killing Efficiency Testing

After 18 h treatment of microorganisms with various concentrations of peptide (0.5×MIC, MIC and 2×MIC), the respective samples were subjected to a series of ten-fold dilutions and plated onto LB agar plates. The plates were then incubated overnight and counted for colony-forming units. A sample containing microbes treated with 10% (by volume) water was used as a control. Results are expressed as Log (CFU/mL) and as % Kill=[(cell count of control−survivor count of peptide-treated microbes)/cell count of control]× 100.

Field Emission-scanning Electron (FE-SEM) Microscopy Analysis

*S. aureus* and *P. aeruginosa* suspensions at ~3×10$^8$ CFU mL$^{-1}$ (100 μL) were separately incubated with an equal volume of broth containing final concentrations of 10% (by volume) of HPLC water or 125 mg L$^{-1}$ of IK8-all D in a 96 well-plate for 2 h. Eight replicates of each condition was pooled into a microfuge tube, pelleted down at 4000 rpm for 5 min, and rinsed twice with PBS. The samples were then fixed with 4% formaldehyde at room temperature for 20 min, followed by rinsing with deionized water. Dehydration of the cells was performed using a series of graded ethanol solutions (35, 50, 75, 90, 95 and 100%). The samples were mounted on a copper tape, allowed to air-dry and sputter coated with platinum for imaging using a FE-SEM setup (JEOL JSM-7400F, Japan).

Haemolytic Activity Testing

Fresh rabbit red blood cells were subjected to 25× dilution with RPMI1640 to obtain an approximate 4% (by volume) suspension for use in this experiment. 300 μL of red blood cells suspension was added to each tube containing equal volume (300 μL) of peptide solutions in RPMI1640. The tubes were incubated at 37° C. for 1 h before subjected to centrifugation at 1000×g for 5 min. Aliquots (100 μL) of supernatant were transferred to each well of a 96-well plate and analysed for haemoglobin release at 576 nm using a microplate reader (TECAN, Switzerland). Red blood cells suspension incubated with RPMI1640 was used as negative control. Absorbance of red blood cells lyzed with 0.1% v/v Triton X-100 was used as the positive control and taken to be 100% haemolytic. Percentage of haemolysis was calculated using the following formula: Haemolysis (%)=[(O.D.576 nm of treated sample−O.D.576 nm of negative control)/(O.D.576 nm of positive control−O.D.576 nm of negative control)]× 100. Data are expressed as mean±standard deviations of 4 replicates.

Drug Resistance Study and Antimicrobial Activities Against Drug Resistant Bacteria E. coli and S. aureus (initial loading level of 3×10$^5$ CFU mL$^{-1}$) were treated repeatedly for up to 20 passages with various concentrations of the peptide IK8-all D as well as the clinically used ciprofloxacin, gentamicin and penicillin G antibiotics according to the broth microdilution method described earlier. After the end of 18 h incubation at each passage, bacterial cells (at ¼ MIC of the particular passage) were sub-cultured and allowed to grow to reach mid-logarithmic growth phase before being used in the subsequent MIC testing. By recording the changes in MIC with each passage, i.e. MIC at passage n normalized to that at the initial passage (MIC$_n$/MIC$_0$), drug resistance development can be monitored. At the end of this assay, the ciprofloxacin and gentamicin resistant E. coli cultures developed were treated with various concentrations of IK8-all D to determine if it could effectively overcome antibiotics drug resistance.

Cell Culture

Mouse alveolar macrophage cell line RAW264.7 and human foetal lung fibroblast WI-38 cells were respectively maintained in DMEM and RPMI media, supplemented with 2 mM L-glutamine, 1.5 g L$^{-1}$ sodium bicarbonate and 10% FBS, and cultured at 37° C. under an atmosphere of 5% $CO_2$ and 95% humidified air.

Intracellular Bacteria Killing

RAW264.7 cells were seeded at a density of 4×10$^5$ per well of a 12-well plate. Following an overnight incubation, the cells were infected for 1 h with 13.3 μL of processed bacteria (3.0×10$^8$ CFU mL$^{-1}$) to achieve a 10:1 multiplicity of infection. The cells were then rinsed twice with 1×PBS and incubated with 1 mL of fresh media containing 50 μg mL$^{-1}$ gentamicin for 45 min to eliminate extracellular bacteria. The media in each well were removed and the infected cells were incubated with fresh media containing 10% (by volume) water or various concentrations of IK8-all D (2, 3.9, 7.8, 15.6 and 31.3 mg L$^{-1}$) for up to 4 and 8 h. At the respective time points, the infected cells were trypsinized, rinsed twice with PBS and lyzed with 800 μL of sterile water with incubation at room temperature for 10 min, followed by 5 min sonication. The intracellular bacteria count was determined by plating serially diluted cultures onto LB agar and enumerated after 24 h.

Cytotoxicity Testing

RAW264.7 and WI-38 cells were respectively seeded at a density of 1.5×10$^4$ and 1×10$^4$ per well of a 96-well plate. Following overnight incubation, the cells were treated with 1.0 to 125 mg L$^{-1}$ of IK8-all D for 48 h. Subsequently, the incubation media in each well were replaced with 100 μL of growth media and 10 μL of MTT solution (5 mg·ml$^{-1}$ in PBS) and the cells were incubated for 4 h at 37° C. according to the manufacturer's directions. Resultant formazan crystals formed in each well were solubilized using 150 μL of DMSO upon removal of growth media. A 100 μL aliquot from each well was then transferred to a new 96-well plate for determination of absorbance using a microplate spectrophotometer at wavelengths of 550 nm and 690 nm. Relative cell viability was expressed as [(A$_{550}$−A$_{690}$)$_{sample}$/(A$_{550}$−A$_{690}$)$_{control}$]× 100%. Data are expressed as mean±standard deviations from two independent experiments performed in four replicates per concentration.

Results

Peptide Design and Characterization

Example 1 above described the design of short synthetic β-sheet forming peptides composed of naturally occurring L-amino acids and demonstrated their broad spectrum and highly selective antimicrobial activities against clinically relevant microorganisms. In this study, substitutions with D-amino acids were performed using optimal β-sheet folding peptides (IRIK)$_2$-NH$_2$ (SEQ ID NO: 17) (IK8-all L) and (IRVK)$_3$-NH$_2$ (SEQ ID NO: 22) (IK12-all L) of n=1.5, 2 or 3 repeat units respectively, which were previously optimized for antimicrobial activities, selectivities and endotoxin neutralization properties. All the designed peptides were amidated at the C-terminal to confer a high net positive charge for enhanced antimicrobial activities. As shown in Table 3, the observed molecular weights of the synthesized peptide sequences determined using MALDI-TOF mass spectrometry were in close agreement with theoretical values, indicating that the products agree closely with the designed compositions.

TABLE 3

Design and characterization of β-sheet forming peptides.

| Peptide designation | Sequence[a] | SEQ ID NO: | Theoretical M$_w$ | Observed M$_w$[b] |
|---|---|---|---|---|
| IK8-all L | IRIKIRIK-NH$_2$ | 17 | 1038.39 | 1039.84 |
| IK8-all D | irikirik-NH$_2$ | 18 | 1038.39 | 1040.28 |

TABLE 3-continued

Design and characterization of β-sheet forming peptides.

| Peptide designation | Sequence[a] | SEQ ID NO: | Theoretical $M_w$ | Observed $M_w$[b] |
|---|---|---|---|---|
| IK8-4D | lrlklrlk-NH$_2$ | 24 | 1038.39 | 1039.81 |
| IK8-2D | IRlklrlK-NH$_2$ | 19 | 1038.39 | 1039.74 |
| IK6-all D | irikir-NH$_2$ | 10 | 797.06 | 798.23 |
| IK12-all L | IRVKIRVKIRVK-NH$_2$ | 22 | 1506.99 | 1510.43 |
| IK12-all D | irvkirvkirvk-NH$_2$ | 23 | 1506.99 | 1508.26 |
| Control-all L | IIRKIIRK-NH$_2$ | 25 | 1038.39 | 1040.07 |
| Control-all D | iirkiirk-NH$_2$ | 26 | 1038.39 | 1040.81 |
| Control-4D | lirKlirK-NH$_2$ | 27 | 1038.39 | 1040.90 |

Figure 11:
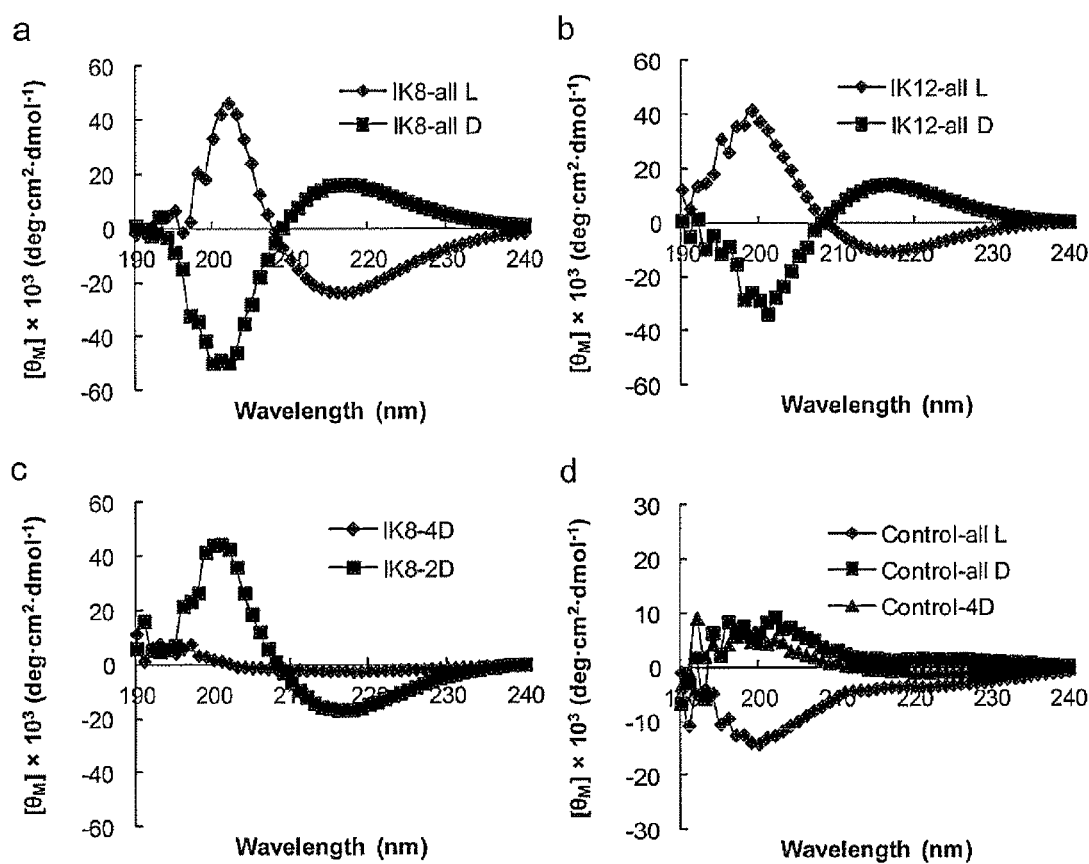
FIG. 11 shows circular dichroism spectra of (a) IK8 enantiomers, (b) IK12 enantiomers, (c) IK8 stereoisomers and (d) control peptides in microbial membrane-mimicking conditions (25 mM SDS micelles solution).
Figure 18:
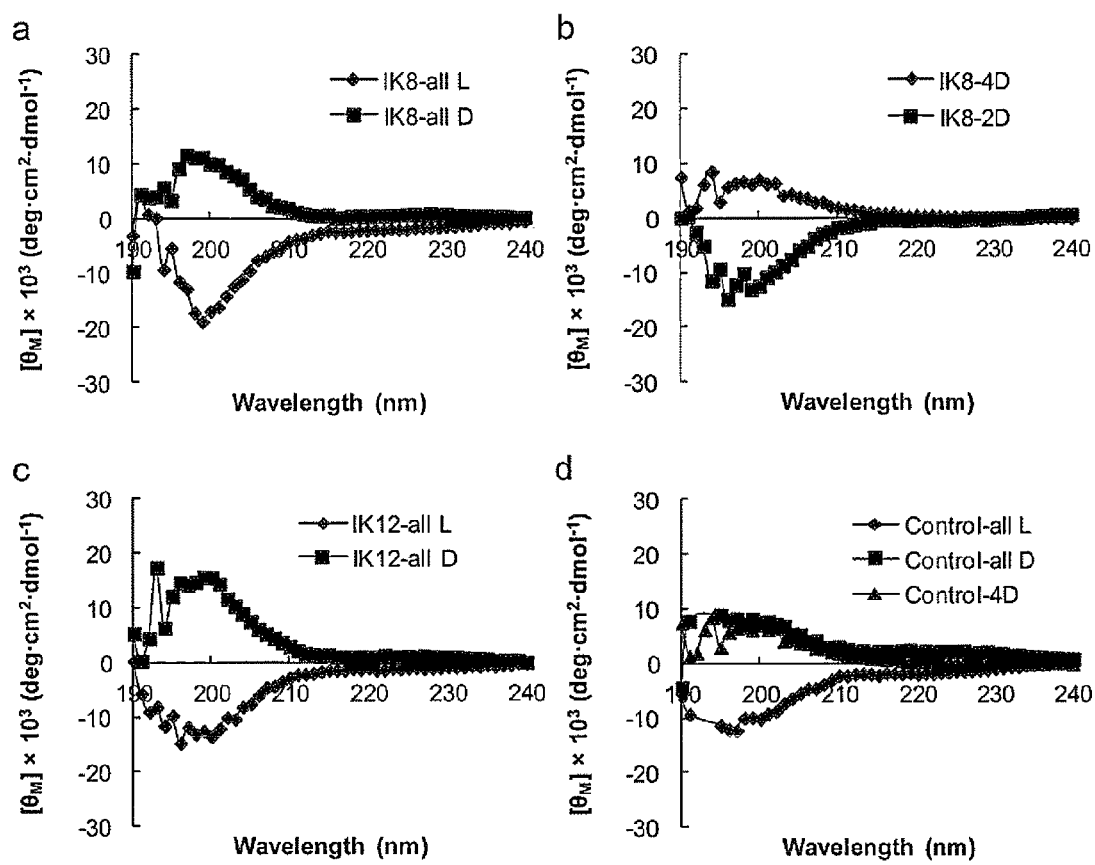
FIG. 18 shows the circular dichroism spectra of (a) IK8 enantiomers, (b) IK8 stereoisomers, (c) IK12 enantiomers and (d) control peptides in deionized water.

[a]Small underlined residues represent D-amino acids.
[b]Measured by MALDI-TOF MS, apparent $M_w = [M_w + H]^+$ Secondary structure formation of the designed peptides was investigated in microbial membrane-mimicking environments using CD spectroscopy. IK8-all L and IK12-all L readily self-assembled to form β-sheet secondary structures in 25 mM SDS micelles solution as evident from a characteristic maxima at ~200 nm and minima at ~218 nm (FIG. 11a and 11b). Corresponding enantiomers IK8-all D and IK12-all D were exact mirror images with ellipticities that were approximately equivalent but opposite in sign as compared to that of their L-counterparts. Interestingly, the selective D-amino acid substitution at positions 2, 4, 6, 8 (IK8-4D) in the optimal IK8-all L sequence led to a complete loss of secondary structure, whereas substitutions only at positions 4, 6 (IK8-2D) enabled the retention of β-sheet forming propensity (FIG. 11c). As β-sheet formation is governed by intermolecular hydrogen bonding between the side chain functional groups in a given peptide, extensive D-amino acid incorporation in IK8-4D possibly affected the spatial positioning of functional groups within the peptide structure, leading to the loss of interactions between adjacent peptide molecules to disrupt β-sheet formation. The rearrangement of cationic and hydrophobic amino acids within the β-sheet forming sequence IK8-all L to yield control peptides (IIRK)$_2$-NH$_2$ (Control-all L; SEQ ID NO: 25), (iirk)$_2$-NH$_2$ (Control-all D; SEQ ID NO: 26) and (IirK)$_2$-NH$_2$ (Control-4D; SEQ ID NO: 275) (Table 3) led to a loss of secondary structures; with their existence as random coils under the test conditions even though the overall charge and hydrophobicity of the molecules remained unchanged (FIG. 11d). This result thus indicates that the alternate hydrophobic and hydrophilic spatial positioning of the amino acids is essential for the formation of β-sheets in membrane conditions. As shown in FIG. 18, the designed peptides remained as random coils in deionized water, hence demonstrating the specificity of the respective β-sheet forming peptides for the amphiphilic microbial membrane-mimics.

Antimicrobial Activities and Selectivities

The antimicrobial activities of the designed peptides were evaluated against a panel of clinically relevant microorganisms, including *S. epidermidis* and *S. aureus* (Gram-positive), *E. coli* and *P. aeruginosa* (Gram-negative) as well as *C. albicans* (yeast).

TABLE 4

Minimum inhibitory concentrations (MICs) and selectivity indices of synthetic antimicrobial peptides

| Antimicrobial peptide | MIC (mg L$^{-1}$) | | | | | GM[a] (mg L$^{-1}$) | HC10[b] (mg L$^{-1}$) | SI[c] |
| | S. epidermidis | S. aureus | E. coli | P. aeruginosa | C. albicans | | | |
|---|---|---|---|---|---|---|---|---|
| IK8-all L | 3.9 | 62.5 | 15.6 | 31.3 | 3.9 | 23.4 | 2000 | 85.5 |
| IK8-all D | 2.0 | 3.9 | 3.9 | 7.8 | 3.9 | 4.3 | 1750 | 407.0 |
| IK8-4D | >500 | >500 | >500 | >500 | >500 | — | >2000 | — |
| IK8-2D | 3.9 | 31.3 | 15.6 | 7.8 | 3.9 | 12.5 | 1600 | 128.0 |
| IK6-all D | — | 250 | 62.5 | 125 | 15.6 | 113.3 | — | — |
| IK12-all L | 2.0 | 31.3 | 15.6 | 62.5 | 125 | 47.3 | >125[e] | >>2.6 |
| IK12-all D | 1.0 | 7.8 | 7.8 | 15.6 | 31.3 | 12.7 | >125[e] | >>9.8 |
| Control-all L | >500 | >500 | >500 | >500 | 500 | — | >2000 | — |
| Control-all D | >500 | >500 | >500 | >500 | 250 | — | >2000 | — |
| Control-4D | 125 | >500 | 31.3 | 125 | 62.5 | 85.9[d] | >2000 | 23.3 |

[a] Geometric mean (GM) of MIC values for the 5 microorganisms tested.
[b] Haemolysis concentration 10% (HC10) is defined as the lowest peptide concentration that induces ≥10% haemolysis.
[c] Selectivity index (SI) is calculated as $\frac{HC_{10}}{GM}$.
[d] GM of MIC values for the 4 microorganisms which the peptide has activity against.
[e] Precipitation occurred in RPMI1640 media from 125 mg L$^{-1}$.

From Table 4, it can be seen that peptide sequences which assembled into β-sheets under microbial membrane-mimicking conditions demonstrated substantially stronger and broader spectrum of activities against all the microorganisms tested as compared to the non-β-sheet forming peptides regardless of stereochemistry (Table 4). For instance, the geometric mean (GM) minimum inhibitory concentrations (MICs) of the various β-sheet forming peptides ranges from 4.3-113.3 mg L$^{-1}$, whereas the non-β-sheet forming control peptides and IK8-4D displayed no or marked reduced antimicrobial activities. This observation thus demonstrates that the self-assembly of the designed AMPs to form β-sheet secondary structures is crucial for their strong antimicrobial properties. This finding is consistent with literature reports in which the bioactivity of AMPs is frequently associated with the segregation of cationic and hydrophobic amino acid residues on opposite planes upon formation of secondary structures leading to disruption of membrane lipid bilayers. Interestingly, the selective substitution of D-amino acids in the $2^{nd}$ and $3^{rd}$ position of the non-β-sheet forming IIRK motif (Control-all L) to obtain (IirK)$_2$-NH$_2$ (Control-4D) partially restored antimicrobial activities against *S. epidermidis, E. coli, P. aeruginosa* and *C. albicans* (Table 4). In particular, the MIC values against *E. coli* were increased by ~16-folds from >500 to 31.3 mg L$^{-1}$. The antimicrobial activities of this peptide, however, remained lower than the β-sheet forming peptides of equal length, charge and hydrophobicity (i.e. IK8-all L or IK8-all D).

Additionally, it was also found that the substitution with D-amino acids considerably improved antimicrobial activities in β-sheet forming peptides regardless of the number of repeat units (n=2 or 3) or peptide length. This effect was especially pronounced with the shorter IK8-all D peptide with n=2 repeat units for which the MIC values against the various bacteria were 2-16 fold lower than its L-enantiomer. In comparison, IK12-all D mediated 2-4 fold reduction in MIC values with enhanced antifungal activity against *C. albicans* as compared to its corresponding L-enantiomer. Among the various peptides, IK8-all D demonstrated the most potent antimicrobial activities, with a very low geometric mean (GM) MIC value of 4.3 mg L$^{-1}$ against the various types of microorganisms, which is superior to that obtained for the clinically used lipopeptide antibiotic polymyxin B (41.4 mg L$^{-1}$) under identical testing conditions. A further reduction in the peptide length to 6 D-amino acids (n=1.5) led to a reduction in antimicrobial activities with a higher GM MIC value of 113.3 mg L$^{-1}$, indicating that β-sheet forming peptides with n=2 repeat units provided the most optimal structure for antimicrobial activities.

The haemolytic activities of the synthetic peptides were evaluated using 4% (by volume) rabbit blood. As reported previously, the all L-amino acids containing β-sheet forming peptides displayed minimal or no haemolysis at MIC values, with high selectivities for microbial membranes (also shown in FIG. 2 and Table 2). In this present study, it was found that the difference in the haemolytic activities between enantiomeric forms of β-sheet forming peptides of n=2 repeat units was small, with high HC$_{10}$ values of 2000 and 1750 mg L$^{-1}$ for IK8-all L and IK8-all D, respectively (Table 4). With the strong improvements in antimicrobial activities observed earlier, these results clearly demonstrated the superior selectivities of the D-enantiomers toward the anionic microbial membranes over zwitterionic mammalian cell membranes, giving rise to very high SIs of 407.0 and >>9.8 mg L$^{-1}$ for IK8-all D and IK12-all D, respectively (Table 4). Taken together, these results suggest that the D-enantiomer of the n=2 synthetic β-sheet forming peptide, IK8-all D, with its broad spectrum and highly selective antimicrobial activities may be a strong therapeutic candidate for the treatment of drug resistant microbial infections.

Figure 12:
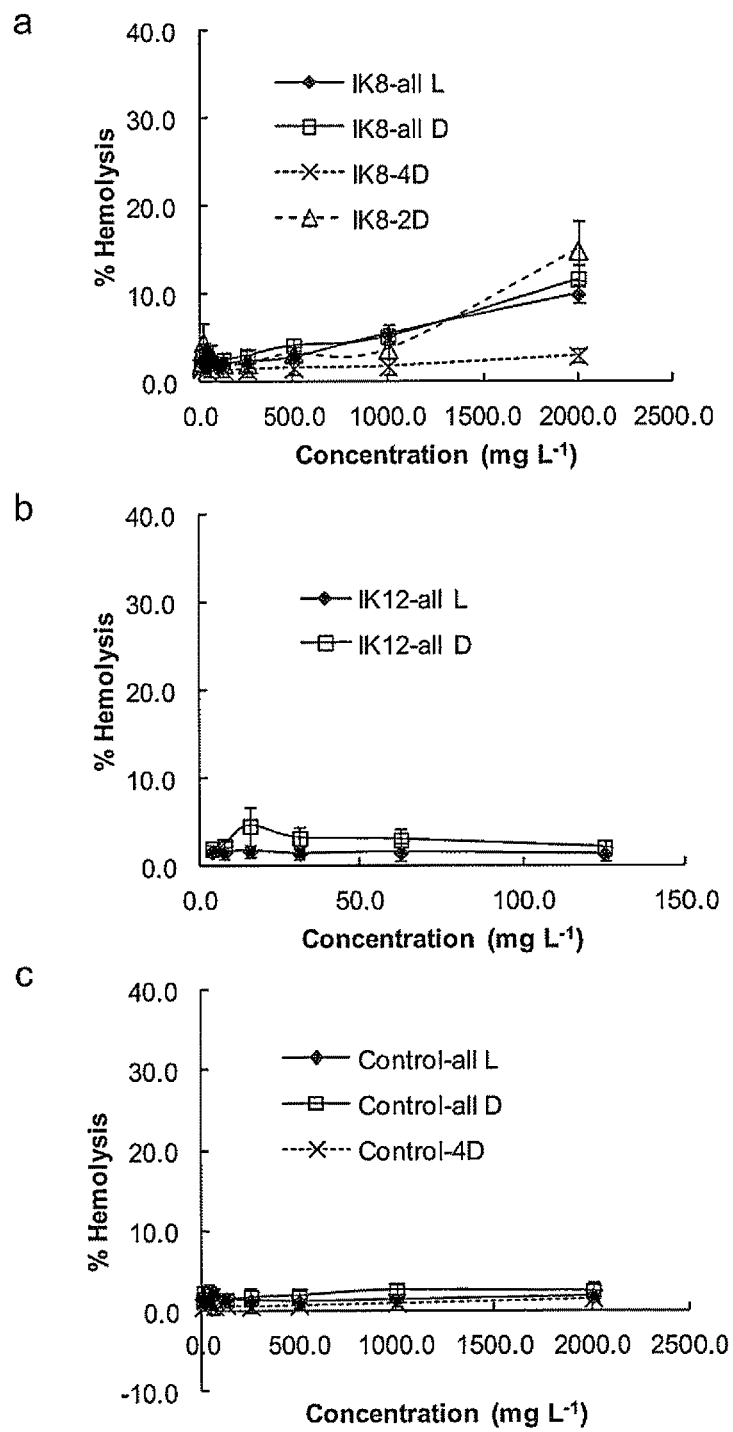
FIG. 12 shows haemolytic activities of (a) IK8 stereoisomers, (b) IK12 enantiomers and (c) IK8 non-β-sheet forming peptide controls in rabbit red blood cells.

Consistent with their poor antimicrobial activities, the non-β-sheet forming peptides, Control-all L and Control-all D, induced minimal or no haemolysis up to 2500 mg L$^{-1}$ (FIG. 12*c*), indicating similarly weak interactions with red blood cell membranes. Likewise, the D-amino acid substituted non-β-sheet forming peptide Control-4D, which demonstrated some degree of antimicrobial activities against several microorganisms, also induced minimal haemolysis, hence giving rise to a high selectivity index (SI) of >23.3 (Table 4). These results suggest that the altered peptide conformation obtained upon substitution with D-amino acids could still permit a moderate degree of interaction with certain microbial membrane compositions without affecting eukaryotic membranes in the absence of secondary structure formation (FIG. 11*d*).

Resistance to Protease Degradation

One of the major factors limiting the clinical utility of AMPs lies in their instability to rapid degradation by proteases which are present abundantly in biological fluids and/or secreted by microorganisms. In order to evaluate the proteolytic stability of the designed β-sheet forming peptides, the D- and L-isoforms of the n=2 peptide sequence (IK8-all D or IK8-all L, respectively) were treated with the broad spectrum serine proteases, trypsin and proteinase K, for 6 h and evaluated their antimicrobial activities against *S. aureus, E. coli* and *P. aeruginosa*. As seen in FIG. 13, untreated IK8-all D and IK8-all L effectively inhibited the growth of all three microorganisms after 18 h incubation. Treatment of IK8-all L with the proteases, however, led to a complete loss in bacterial inhibitory activities, suggesting that it has been degraded by the proteases present. IK8-all D, on the other hand, retained its antibacterial activities against the various microorganisms. The structural integrity of synthetic peptides following treatment with both proteases was also evaluated using MALDI-TOF mass spectroscopy. As seen from the MALDI-TOF mass spectra, the treatment of IK8-all L with both proteases led to the degradation of the intact peptide resulting in multiple lower molecular weight peaks (FIG. 19*a*), hence accounting for the loss of antibacterial activities observed earlier. The cleavage sites of both enzymes for the IK8-all L peptide are illustrated in FIG. 19*a* with the mass spectra peaks assigned to the major fragments. Conversely, IK8-all D remained intact after protease treatment, with no lower molecular weight products observed (FIG. 19*b*). This reduced susceptibility to enzymatic degradation, coupled with the superior antimicrobial activities and selectivities observed earlier strongly suggests that IK8-all D is a promising candidate for therapeutic applications.

Membrane-lytic Activities and Drug Resistance Mitigation

Figure 14:
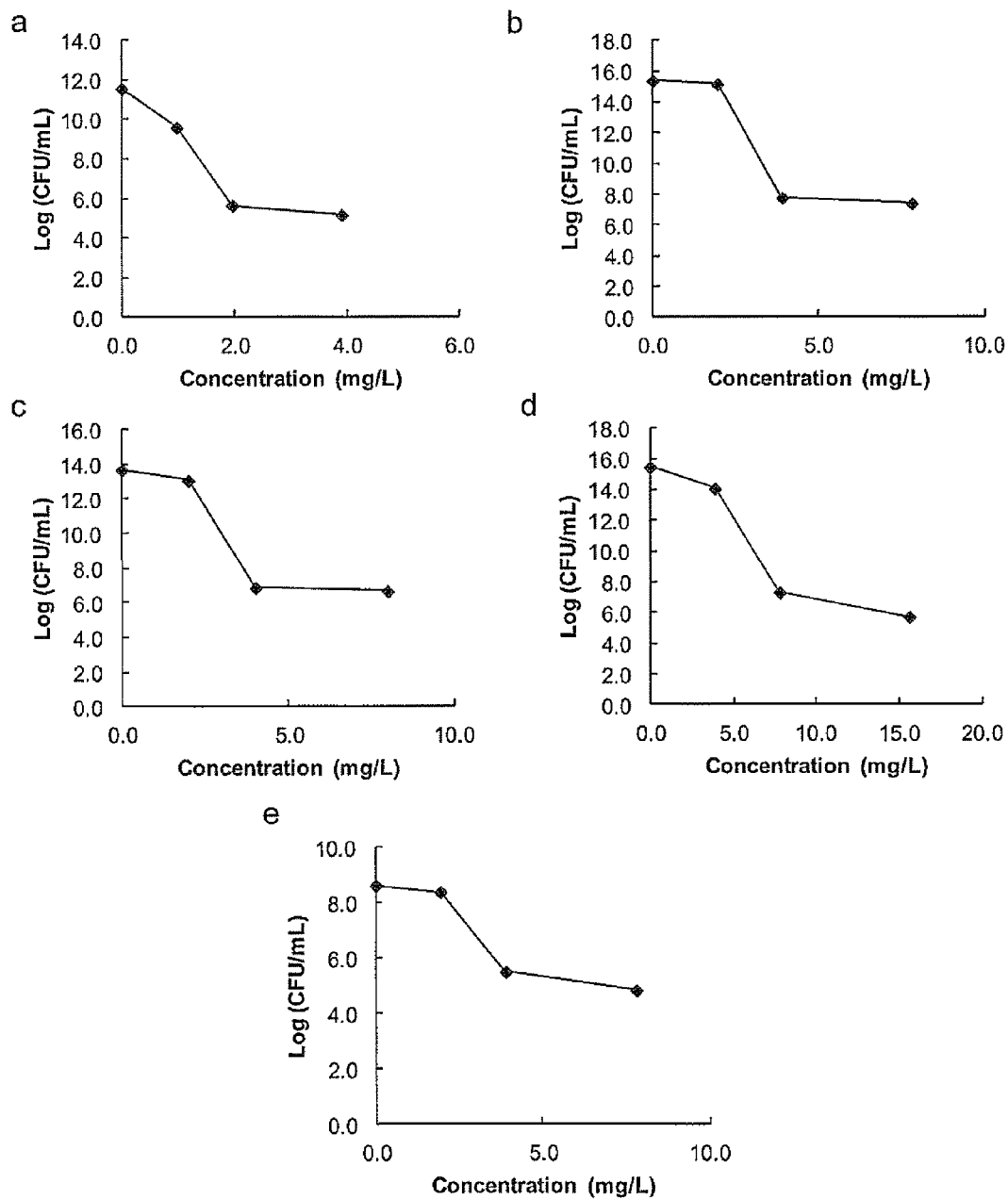
FIG. 14 shows plot of viable colony-forming units (CFU) of (a) *Staphylococcus epidermidis*, (b) *Staphylococcus aureus*, (c) *Escherichia coli*, (d) *Pseudomonas aeruginosa*, and (e) *Candida albicans* after 18 h treatment with IK8-all D at various concentrations (i.e. 0, 0.5×minimum inhibitory concentration (MIC), MIC and 2×MIC). The designed peptide achieved more than 3 log reductions in colony counts (>99.9% kill) for each of the microorganisms at MIC and 2×MIC values, indicating a bactericidal mechanism of action.
Figure 15:
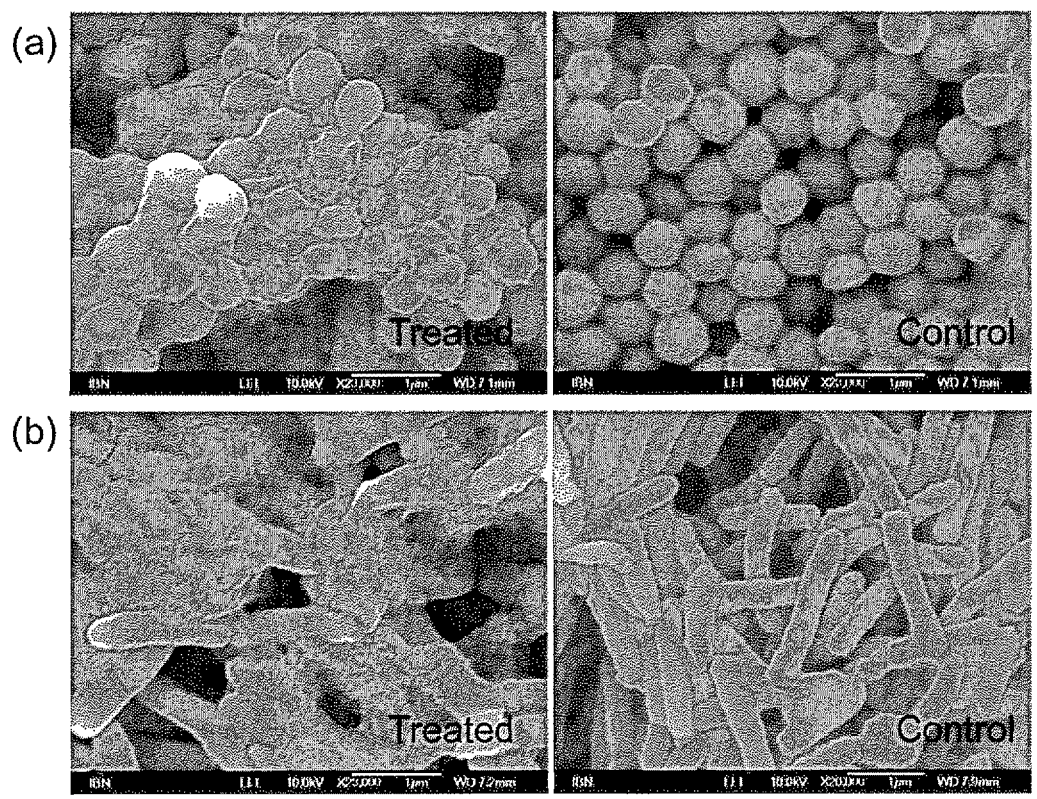
FIG. 15 shows FE-SEM images of (a) *Staphylococcus aureus* and (b) *Pseudomonas aeruginosa* treated for 2 h with 125 mg L$^{-1}$ of IK8-all D and MHBII containing 10% (by volume) HPLC water.

The predominant mechanism of action for AMPs lies in the rapid perturbation and destruction of microbial membranes, leading to the leakage of cytoplasmic contents and eventual cell death. As it is very challenging for microorganisms to repair extensive cell membrane damage, this bactericidal mode of action has been proposed to offer a highly attractive means to prevent and overcome drug resistance mechanisms. The present study first established that similar to its L-enantiomer, IK8-all D mediated a bactericidal mechanism of action, giving rise to more than three log reductions in viable colony counts (>99.9% killing efficiencies) at the respective MIC values for each of the five microorganisms tested in this study (FIG. 14). Under FE-SEM, significant membrane damage and corrugation were observed on the surface of Gram-positive S. aureus and Gram-negative P. aeruginosa after a short 2 h treatment with 125 mg L$^{-1}$ of IK8-all D as compared to the smooth surfaces of the respective controls treated with broth containing 10% (by volume) of water (FIG. 15).

Figure 16:
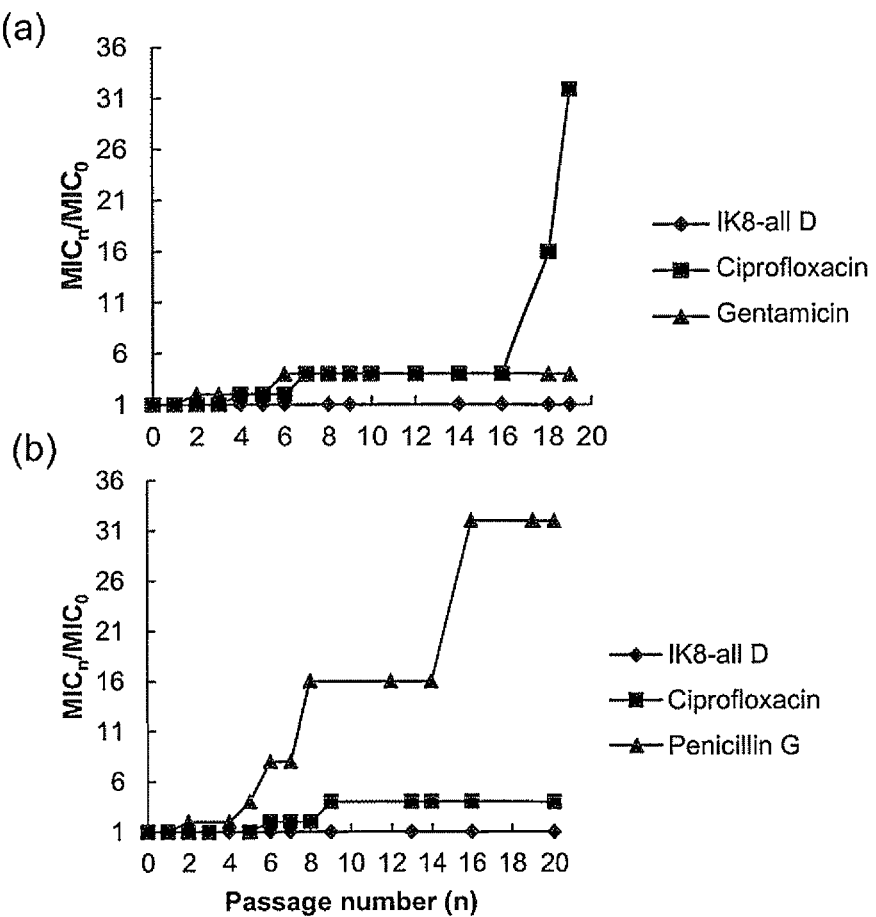
FIG. 16 shows drug resistance development profiles of (a) *Escherichia coli* and (b) *Staphylococcus aureus* exposed to sub-minimum inhibitory concentrations (MIC) of IK8-all D and various clinically used antibiotics.

Prolonged repeated exposures of microorganisms to non-lethal doses of antibiotics are known to promote acquisition of drug resistance. In order to investigate if the membrane disruption mediated by IK8-all D can adequately prevent drug resistance development, E. coli and S. aureus treated with sub-MIC amounts of AMP were passaged daily and used for determination of MIC up to 20 passages. Various classes of clinically used antibiotics including the cell wall synthesis inhibitor penicillin G, bacterial topoisomerase inhibitor ciprofloxacin and protein synthesis inhibitor gentamicin sulfate were included as controls in this study. As shown in FIG. 16, the MIC values of IK8-all D against E. coli and S. aureus remained unchanged at 3.9 mg L$^{-1}$ ($MIC_n/MIC_0=1$) despite repeated treatment with low doses of the designed AMP. Treatment of E. coli with the gentamicin sulfate induced drug resistance as early as passage 2, as seen from the doubling of MIC value ($MIC_n/MIC_0=2$), which subsequently increases to 4-fold the original MIC value by passage 6 ($MIC_n/MIC_0=4$) (FIG. 16a). Ciprofloxacin mediated a slightly delayed onset of drug resistance, with doubling of MIC occurring later at passage 4. This was followed by a quadrupling of MIC value by passage 7, which was followed by a drastic increase in MIC value by 32-fold at the end of the experiment. A similar trend was observed for S. aureus, with an early acquisition of drug resistance and an increase in MICs by 32- and 4-fold for penicillin G and ciprofloxacin, respectively by passage 20 (FIG. 16b). These results, taken together, strongly suggest that the diverse antimicrobial mechanisms of action mediated by various antibiotics influenced their drug resistance development profiles to different extents. Notably, repeated treatment of E. coli and S. aureus with the synthetic β-sheet forming peptide did not induce any drug resistance development within the course of the experiment.

Figure 20:
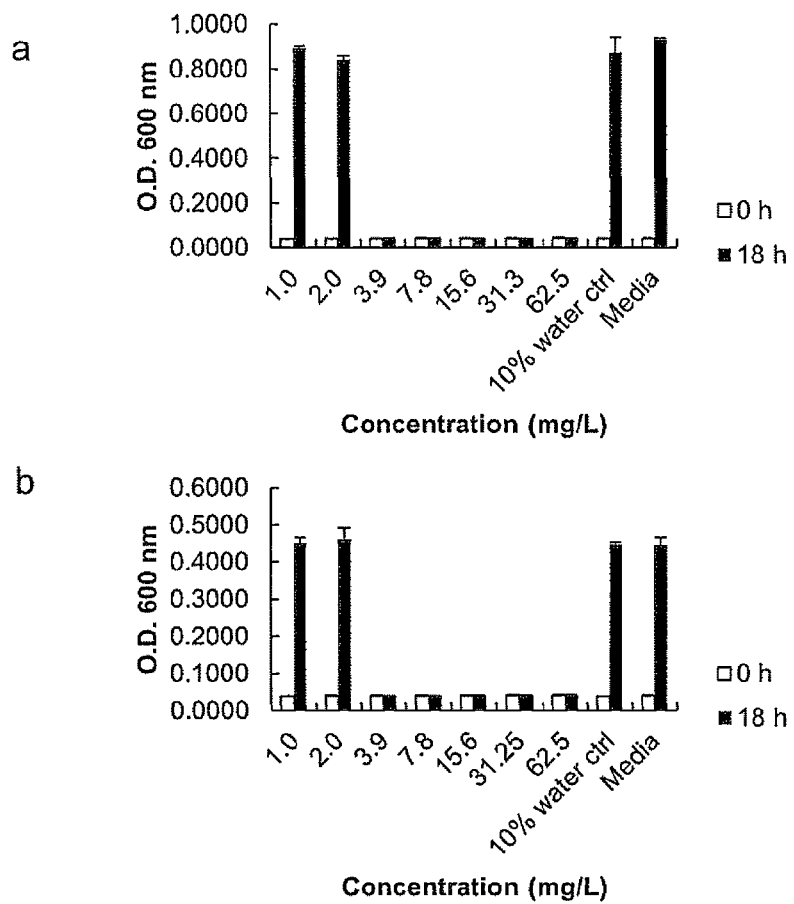
FIG. 20 shows minimum inhibitory concentration (MIC) determination of (a) ciprofloxacin- and (b) gentamicin-resistant *Escherichia coli* after 18 h treatment with the synthetic antimicrobial peptide IK8-all D.

Besides being able to prevent drug resistance development, treatment of the gentamicin- and ciprofloxacin-resistant E. coli derived from this experiment with IK8-all D also revealed that the synthetic peptide effectively inhibited bacterial growth at the same concentration (i.e. 3.9 mg L$^{-1}$) as that in the wild type (non-drug resistant) bacteria (FIG. 20). This result provides strong evidence that the membrane disrupting abilities of the β-sheet forming peptide could effectively overcome conventional mechanisms of antibiotics resistance to inhibit bacterial growth. The activities of the designed β-sheet forming peptides were further investigated against clinical isolates of drug resistant microorganisms. As seen in Table 5, the designed AMPs demonstrated broad-spectrum antimicrobial activities against MRSA, VRE, multidrug resistant A. baumanni, P. aeruginosa and yeast C. neoformans. Consistent with the results observed earlier, IK8-all D induced stronger antibacterial activities, with 4-8 folds reduction in MBCs as compared to its L-enantiomer. Additionally, IK8-all D, IK8-2D and IK12-all L also demonstrated excellent activities against clinically isolated M. tuberculosis, with MICs ranging from 15.6 to 125 mg L$^{-1}$ (Table 6).

TABLE 5

Minimum microbicidal concentrations (MBCs) of synthetic antimicrobial peptides against clinically isolated drug resistant microorganisms.

| Antimicrobial peptide | MBC (mg L$^{-1}$) | | | | |
|---|---|---|---|---|---|
| | Methicillin-resistant S. aureus | A. baumanni | Vancomycin-resistant Enterococci | P. aeruginosa | C. neoformans |
| IK8-all L | 31.3 | 125 | 15.6 | 7.8 | 7.8 |
| IK8-all D | 3.9 | 31.3 | 3.9 | 15.6 | 7.8 |
| IK12-all L | 15.6 | 15.6 | 7.8 | 15.6 | 15.6 |

TABLE 6

Minimum inhibitory concentrations (MICs) of synthetic antimicrobial peptides against clinically isolated Mycobacterium tuberculosis.

| Antimicrobial peptide | MIC (mg L$^{-1}$) Strain number | | | | | |
|---|---|---|---|---|---|---|
| | 1140 | 1146 | 1173 | 1177 | 1178 | 1179 |
| IK8-all D | 15.6 | 15.6 | — | — | — | — |
| IK8-2D | — | — | 62.5 | 62.5 | 62.5 | 125 |
| IK12-all L | 15.6 | >31.3 | — | — | — | — |

Intracellular Killing of S. aureus in Infected Mouse Macrophages

Figure 17:
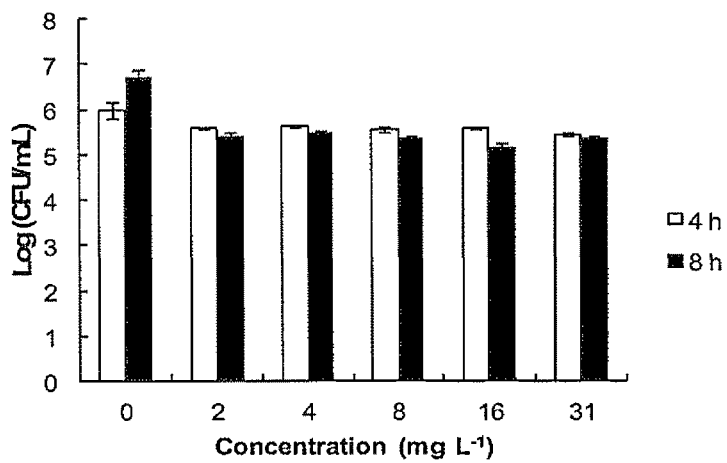
FIG. 17 shows intracellular killing of *Staphylococcus aureus* mediated by IK8-all D in infected mouse macrophage cell line RAW264.7 (MOI 10).
Figure 21:
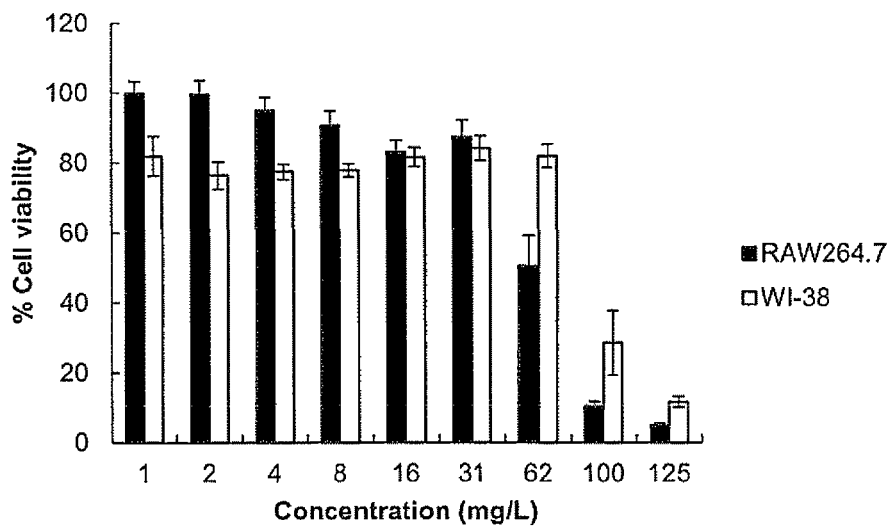
FIG. 21 shows cytotoxicity study of IK8-all D against mouse alveolar macrophage RAW264.7 and human foetal lung fibroblast WI-38 cell lines.

The phagocytosis of microorganisms by alveolar macrophages could potentially create a source of persistent infections due to the survival and protection of bacteria from many extracellular antibiotics that penetrate poorly into cells. S. aureus is a clinically relevant example of an opportunistic pathogen that can survive within alveolar macrophages and is frequently implicated in community and nosocomial acquired cases of lung infections. As such, the ability of the synthetic AMP to eradicate intracellular S. aureus was investigated next. Infected RAW264.7 mouse alveolar macrophages were treated with various doses of IK8-all D for 4 and 8 h. As seen from FIG. 17, there was a significant decrease in intracellular S. aureus colony counts after treatment with IK8-all D for 4 and 8 h when compared with that obtained for the control treated with media containing 10% (by volume) water (P<0.01). For instance, the designed peptide effectively mediated 1.2-1.5 log reductions in colony counts at 8 h when compared to the control (FIG. 17). Importantly, the intracellular killing of S. aureus mediated by IK8-all D was found to be independent of the cytotoxicity of the peptide as more than 80% cell viability was observed at bactericidal doses (FIG. 21). The cytotoxicity of IK8-all D was also investigated in the human foetal lung fibroblast WI-38 cell line and it was demonstrated more than 77% cell viability up to 62.5 mg L$^{-1}$, which is well above its antimicrobial concentrations. Taken together, these results demonstrated that besides its potent activities in extracellular bacterial killing, the designed β-sheet forming peptide could also effectively enter infected cells to reduce intracellular bacteria loads with minimal cytotoxicities.

Example 2 investigated the importance of secondary structure formation and effects of stereochemistry on antimicrobial activities and selectivities. It was demonstrated that the self-assembly of the synthetic peptide into β-sheets under microbial membrane-mimicking conditions was essential for its strong antimicrobial activities. Among the various peptides, IK8-all D exhibited the most potent antimicrobial activities, with a very high selectivity index of 407.0. The D-enantiomer also displayed enhanced stability in the presence of broad spectrum proteases, trypsin and proteinase K. Additionally, membrane-lytic activities of IK8-all D provided an effective means to prevent drug resistance development and effectively mediated killing of various clinically isolated multidrug-resistant microorganisms. Besides its potency against extracellular microorganisms, the synthetic β-sheet forming peptide IK8-all D also demonstrated efficient killing of intracellular S. aureus. Taken together, these results show that the D-amino acids substituted β-sheet forming peptide IK8-all D with its enhanced antimicrobial activities and improved protease stability, may be used to combat antibiotics resistance microorganisms in various clinical applications.

Example 3

Investigation into the Antiproliferative Properties of Peptides of the Present Disclosure Cell Culture The human cervical cancer HeLa cell line, human dermal fibroblast HDF cell line and rat macrophage NR8383 cell line were respectively maintained in RPMI, DMEM and FK15 growth media supplemented with 10% FBS, 100 U mL$^{-1}$ penicillin and 100 mg mL-1 streptomycin and cultured at 37° C. under an atmosphere of 5% CO2 and 95% humidified air.

Cell Viability Testing

HeLa, HDF and NR8383 cells were respectively seeded at a densities of 1×10$^4$, 1×10$^4$ and 4×10$^4$ cells per well of a 96-well plate. Following overnight incubation, the cells were treated with 3.9 to 500 mg L$^{-1}$ of (IRIK)$_3$-NH$_2$ (SEQ ID NO: 21) and (VRVK)$_3$-NH$_2$ (SEQ ID NO: 20) for 24 h. For the adherent HeLa and HDF cell lines, the incubation media in each well were replaced with 100 μL of growth media and 10 μL of MTT solution (5 mg·ml$^{-1}$ in PBS). The cells were further incubated for 4 h at 37° C. according to the manufacturer's directions. Resultant formazan crystals formed in each well were solubilized using 150 μL of DMSO upon removal of growth media. A 100 μL aliquot from each well was then transferred to a new 96-well plate for determination of absorbance using a microplate spectrophotometer at wavelengths of 550 nm and 690 nm. Relative cell viability was expressed as $[(A_{550}-A_{690})_{sample}/(A_{550}-A_{690})_{control}]\times 100\%$. Data are expressed as mean±standard deviations from two independent experiments performed in four replicates per concentration.

For the semi-adherent NR8383 cells, 20 μL of CELLTITER-BLUE® reagent was added into each well after treatment and the plate was incubated for a further 4 h. The fluorescence intensity readings of the wells were determined at excitation wavelength of 560 nm and emission wavelength of 590 nm using a microplate reader. Control wells containing peptide solutions in the absence of cells were included to determine background fluorescence. $=[(F_{treated\ sample}-F_{corresponding\ background})/(F_{10\%\ water\ control}-F_{10\%\ water\ control\ background})]\times 100$. Data are expressed as mean±standard deviations of 4 replicates.

Results

Figure 22:
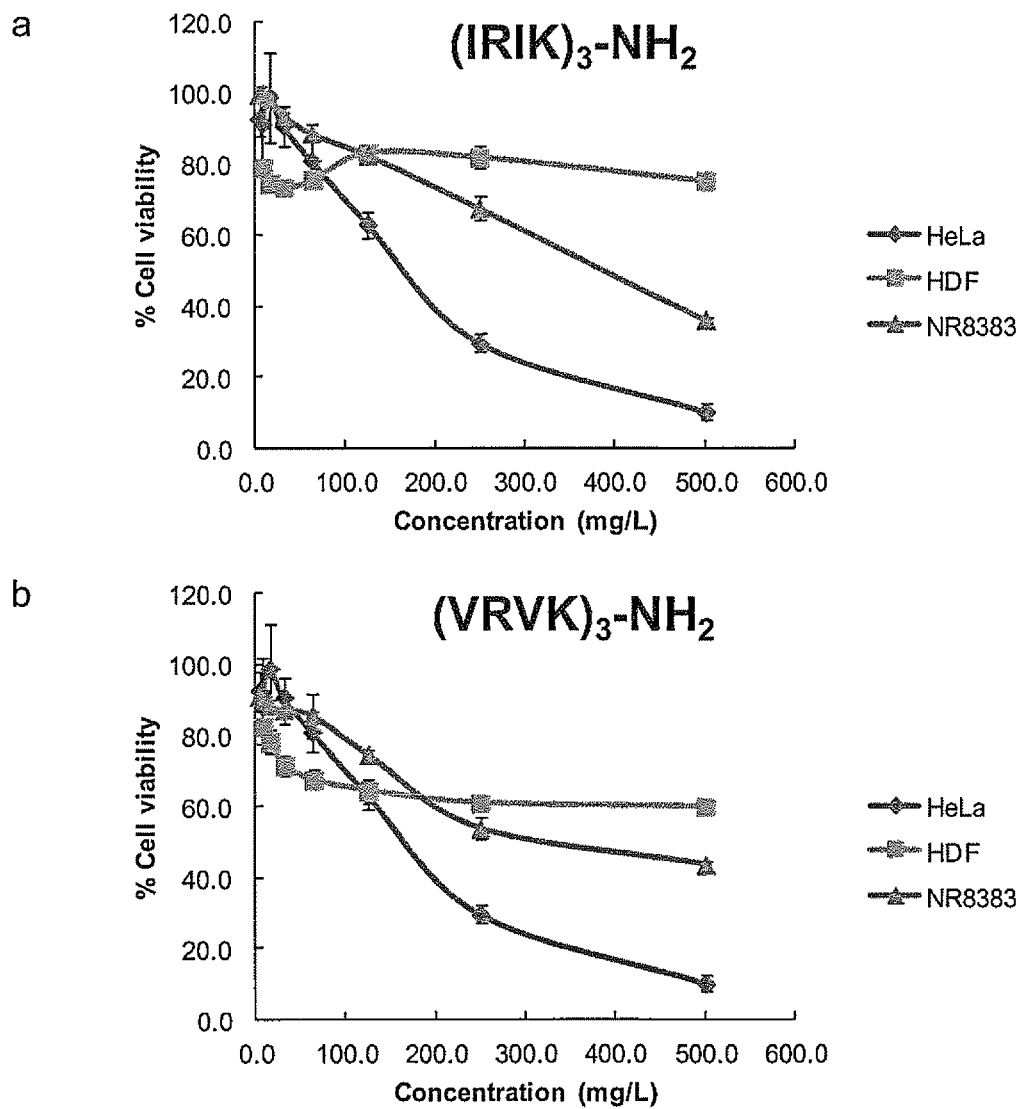
FIG. 22 shows that the peptides of the present disclosure selectively kills cancer cells (HeLa) and are less cytotoxic towards non-cancerous rat alveolar macrophages (NR8383) and human dermal fibroblast cell lines.

As seen from FIG. 22, treatment of HeLa cervical cancer cell line with (IRIK)$_3$-NH$_2$ (SEQ ID NO: 21) resulted in a concentration-dependent decrease in cell viability to less than 70% from 125 mg/L onwards. On the other hand, more than 80% of the non-cancerous HDF and NR8383 cells were viable at 125 mg/L. Similarly, treatment of HeLa cells with (VRVK)$_3$-NH$_2$ (SEQ ID NO: 20) resulted in only 30% cell viability at 250 mg/L while HDF and NR8383 cells had more than 53% cell viabilities. These results thus demonstrate that the β-sheet forming peptides have greater selectivities for the more anionic cancer cell membranes over the normal cell membranes.

Example 4

Investigation into the Effect of the Peptides of the Present Disclosure on Keratitis Materials and Methods Peptide Characterisation Peptides used in this study were synthesized by GL Biochem (Shanghai, China) and purified to more than 95% using analytical reverse phase (RP)-HPLC. The molecular weights of the peptides were further confirmed using matrix-assisted laser desorption/ionization time-of-flight mass spectroscopy (MALDI-TOF MS, Model Autoflex II, Bruker Daltonics Inc., U.S.A.) using α-cyano-4-hydroxycinnamic acid (4-HCCA) as matrix. 4-HCCA was purchased from Sigma-Aldrich (Singapore) and used in saturated acetonitrile/water (1:1 volume ratio) after re-crystallization. Phosphate-buffered saline (10× PBS) was purchased from 1$^{st}$ Base (Singapore) and diluted to the intended concentration before use. Mueller-Hinton Broth II (MHB II) and yeast mould broth (YMB) powders were purchased from BD Diagnostics (Singapore) and re-constituted according to the manufacturer's instructions. *Staphylococcus epidermidis* (ATCC No. 12228), *Staphylococcus aureus* (ATCC No. 29737), *Escherichia coli* (ATCC No. 25922), *Pseudomonas aeruginosa* (ATCC No. 9027) and yeast *Candida albicans* (ATCC No. 10231) were obtained from ATCC (U.S.A) and cultivated according to the recommended protocols. Lipopolysaccharide (LPS) and FITC-conjugated LPS from *E. coli* 0111:B4 were purchased from Sigma-Aldrich. Griess reagent system was obtained from Promega (U.S.A.) and used according to the manufacturer's protocol.

Determination of Minimum Inhibitory Concentration (MIC)

The MICs of peptides were determined against the fungi *C. albicans* (American Type Culture Collection, ATCC) and *F. solani* (ATCC) by the broth microdilution method. *C. albicans* were grown in yeast mold broth (YMB), at room temperature under constant shaking at 300 rpm to reach mid-logarithmic growth phase. The microbial suspensions were diluted with the appropriate broths, and adjusted to give an initial optical density (O.D.) reading of ~0.07 at a wavelength of 600 nm on a microplate reader (TECAN, Switzerland), which corresponds to McFarland Standard No. 1 (~3×10$^8$ CFU mL-1). The peptides were dissolved in 0.2 μm-filtered HPLC-grade water, and subjected to a series of two-fold dilutions using the appropriate broths. 100 μL of microorganism suspension with an initial loading level of 3×10$^5$ CFU mL$^{-1}$ was added to an equal volume (100 μL) of peptide solution to achieve final concentrations ranging from 3.9 to 500 mg L$^{-1}$ and with water concentration fixed at 10% (by volume) in each well of a 96-well plate. After 42 h of incubation with shaking at room temperature, the MIC was taken as the lowest peptide concentration at which no microbial growth was observed visually. Yeast cells in broth containing 10% (by volume) of HPLC-grade water, as well as pure broth alone were used as the negative controls. *F. solani*, were cultured on sabouraud dextrose agar plates in incubator at 37° C. To collect conidia following incubation, conidia of *F. solani* species were harvested and standardized to $1 \times 10^8$ spores/ml before performing the experiments. Sabouraud dextrose broth (90 µL) was added to the wells of culture plates. Various concentrations of peptide were prepared in the wells by 2-fold dilution method, and these wells were inoculated with 10 µL of spore suspension containing $1 \times 10^6$ spores. The plates were incubated at 37° C. and examined macroscopically after 24 h for the growth of *F. solani*. Appropriate control wells without any treatment were included in the study. Peptide were considered to be active if the wells appeared clear without any visible growth of *F. solani*, and the results were expressed as MIC. The assay was performed in four replicates for each concentration.

In Vitro Killing Kinetics

The killing kinetics test was performed to evaluate the antimicrobial activities of peptides against *C. albicans*. Yeast solution was re-suspended in YMB (Difco) to achieve from $10^5$ to $10^6$ CFU $mL^{-1}$. The initial inoculum was exposed to peptide 1 at concentrations of 1×, 2× and 4×MIC for 0, 1, 2, 4 and 24 h, and at these time points, the samples were diluted with various dilution factors. Each dilution (20 µL) was plated on agar plate, and incubated 2 days. Surviving colonies were counted after incubation. An untreated inoculum group was used as a negative control. Tests were conducted in triplicates, and the results were presented as killing efficiency (%).

Stability Testing

Peptides 1 and 2 were dissolved in HPLC-grade water at 2 mg/mL, subjected to a standard steam sterilization autoclave cycle at 121° C. for 15 min, and allowed to stand at room temperature for a period of 6 weeks. The integrity of the peptides was determined by evaluating their molecular weights via MALDI-TOF MS before and after treatment.

Antifungal Studies on *C. albicans* Biofilm (In Vitro Keratitis Treatment Model)

*C. albicans* were used as representative fungi for testing the antifungal functions of peptide 1. *C. albicans* suspensions were prepared from fresh overnight cultures in YMB using −80° C.-frozen stock cultures. Subsamples of these cultures were grown for another 3 h, and adjusted to an optical density of ~0.1 at 600 nm, giving a density of $10^7$-$10^8$ CFU/mL.

Preparation of *C. albicans* Biofilm In Vitro

Overnight cultures of *C. albicans* diluted to $3 \times 10^6$ CFU $ml^{-1}$ were added into each well of a 96-well plate at a volume of 100 µL per well, and allowed to adhere for 5 h at 37° C. with gentle shaking at 100 rpm. The wells were then rinsed once with 100 µL of PBS to remove planktonic cells and loosely attached cells, and replenished with 100 µL of fresh broth. Biofilm formation was allowed to proceed up to 2 days with daily rinsing and media changes before experiment.

Biofilm Susceptibility

To determine the effects of peptide treatment on the viability of *C. albicans* in biofilms, 100 µL of peptide 1 solutions at different concentrations was added to each well and allowed to incubate for 24 h. Subsequently, the solutions were removed, rinsed once with 100 µL of PBS before 120 µL of activated XTT solution was added into each well. After 4 h of incubation, 90-µL aliquots from each well was transferred to a new 96-well plate for the determination of absorbance using a microplate reader (TECAN, Switzerland) at measurement and reference wavelengths of 490 nm and 660 nm, respectively. The biofilm treated with a broth containing 10 vol % of water was used as control. Relative cell viability was expressed as $[(A490-A660)sample/(A490-A660)control] \times 100\%$. Data were expressed as mean±standard deviations of 4 replicates for each concentration.

Biomass Assay

The biomass of the biofilms was estimated by a crystal violet staining assay. Briefly, the formed biofilms were first treated with the peptide for 24 h as described above. After aspirating the culture medium, the biofilms were rinsed once with PBS, fixed with methanol for 15 min at room temperature and stained with 100 µL of 0.1% (weight by volume) crystal violet for 10 min. The excess crystal violet dye was removed by rinsing the wells with DI water five times. The dye that is associated with the biofilm was extracted using 100 µL of 33% glacial acetic acid per well, and 60-1 µL aliquot from each well was transferred to a new 96-well plate for quantification of absorbance at a wavelength of 570 nm using a microplate reader (TECAN, Switzerland). The relative amount of biomass remaining after peptide treatment was expressed as a percentage of the control treated with broth containing 10 vol % of water. Data represented mean±standard deviations of 4 replicates for each concentration.

Scanning Electron Microscopy Studies on Biofilm

The morphologies of *C. albicans* biofilm treated with peptide 1 were observed using field emission scanning electron microscopy (FESEM) (JEOL JSM-7400F) operated at an accelerating voltage of 4.0-6.0 keV. The *C. albicans* biofilm was incubated with 1000 mg/L of peptide for 24 h. It was washed with PBS thrice, and then fixed overnight in PBS containing 2.5% of glutaraldehyde. The cells were further washed with DI water, and dehydrated using a series of ethanol washes. Several drops of the suspension were placed on copper tape, and left to dry at room temperature. The samples were coated with platinum prior to FESEM analyses.

In Vivo Mouse Keratitis Treatment Model

Source of Mice

Adult C57BL/6 mice (8-week-old, 18-22 g) were used for animal studies. All mice eyes were examined for absence of ocular pathology before experiments were initiated. The experimental protocol was approved by the Institutional Animal Care and Use Committee of Biological Resource Centre, Agency for Science, Technology and Research (A*STAR), Singapore.

In Vivo Toxicity Evaluation of the Peptides

The peptides were tested in mice eyes. The peptides were administered to the mice at a dose of 3000 mg/L every 5 min during the first hour, and every 30 min during the next 7 h. After a pause of 16 h, eye drops were administered at hourly intervals for another 8 h. All mice were sacrificed 16 h after the administration of the last eye drop. The treated eyeballs were collected immediately. The fixed eyeballs were embedded in paraffin, sectioned and stained with hematoxylin and eosin by the standard protocol.

Contact Lens-associated Keratitis Model

Lotrafilcon A contact lenses used in the present study were purchased from CIBA Vision with a power of +1.50 diopters. The contact lenses were washed with PBS, and immersed in YMB overnight before they were punched into smaller pieces of 2 mm in diameter. To grow *C. albicans* biofilms, the lenses were placed in 6-well tissue culture plates with 4 mL of yeast suspension (107 CFU/mL), and incubated for 3 h at 22° C. The contact lenses were gently washed with PBS to remove non-adherent yeast cells, and immersed in YMB for 48 h at 22° C. with shaking at 100 rpm.

The black mouse keratitis model was established by employing contact lens biofilm infection (as described in Goldblum D, Frueh B E, Sarra G M, Katsoulis K, Zimmerli S. Topical caspofungin for treatment of keratitis caused by *Candida albicans* in a rabbit model. Antimicrob Agents Chemother 2005; 49:1359-63; Li P, Poon Y F, Li W, Zhu H Y, Yeap S H, Cao Y, et al. A polycationic antimicrobial and biocompatible hydrogel with microbe membrane suctioning ability. Nat Mater 2011; 10:149-56; Prakash G, Sharma N, Goel M, Titiyal J S, Vajpayee R B. Evaluation of intrastromal injection of voriconazole as a therapeutic adjunctive for the management of deep recalcitrant fungal keratitis. Am J Ophthalmol 2008; 146:56-9; and Sun Y, Chandra J, Mukherjee P, Szczotka-Flynn L, Ghannoum M A, Pearlman E. A murine model of contact lens-associated *fusarium* keratitis. Invest Ophthalmol V is Sci 2010; 51:1511-6). The mice were anesthetized by ketamine (150 mg/kg) and xylazine (10 mg/mL) via intraperitoneal injection (I.P.). Additional topical anesthetic in the form of 0.5% tetracaine hydrochloride eye drops (Bausch & Lomb, Tampa, Fla.) was also administered.

A total of 29 mice were used in this study. A 1-mm filter paper disc moistened with 99% 1-heptanol (Sigma-Aldrich, Lausanne, Switzerland) was placed on the center of the cornea for 40 s. The corneal epithelium was traumatically wiped out, and the eyes were rinsed with PBS to remove any remaining traces of 1-heptanol. A 2 mm-diameter punch from the contact lens with *C. albicans* biofilm was then placed on the denuded cornea surface. The contact lenses were kept inside the eyes by closing the eye lids with silk sutures. The *C. albicans* cells were grown on the eyeball 18 h after inoculation; eye ulcer with a leathery, tough, raised surface was observed. A disease grading from 0 (no disease) to 4 (severe disease) was established for evaluating treatment efficacy (Table 7). The mice were immune suppressed by subcutaneous injection of cyclophosphamide (Sigma-Aldrich, 180 g/kg).

TABLE 7

Clinical grading and scoring for in vivo keratitis treatment.

| Disease score | 0 | 1 | 2 | 3 | 4 |
|---|---|---|---|---|---|
| Clinical description | Clear cornea | Slightly cloudy cornea | Cloudy cornea; iris and pupil are visible | Cloudy cornea; opacity not yet uniform | Nearly uniform opacity of cornea |
| % opacity | 0 | 1-25 | 26-50 | 51-75 | 76-95 |
| Degree of disease | No disease | Mild | Moderate | Moderate to severe | Severe |

Evaluation of Keratitis Treatment Efficacy Using the Peptides

The animals were randomly treated with 4 topical eye drop solutions: water solution (control), 3000 mg/L of peptide 1 and peptide 2, as well as 1000 mg/L of amphotericin B. Eye drops (20 μl each) were administered to the mice every 5 min during the first hour and every 30 min during the next 7 h. After a pause of 16 h, eye drops were administered at hourly intervals for another 8 h. All mice were sacrificed 16 h after the administration of the last eye drop. The treated eyeballs were collected immediately. 3 eyeballs from each group were collected for histology, and the remaining 6 eyeballs were homogenized for quantitative fungal recovery study. The fixed eyeballs were embedded in paraffin, sectioned and stained with Grocott's methenamine silver by the standard protocol.

Results

Figure 23:
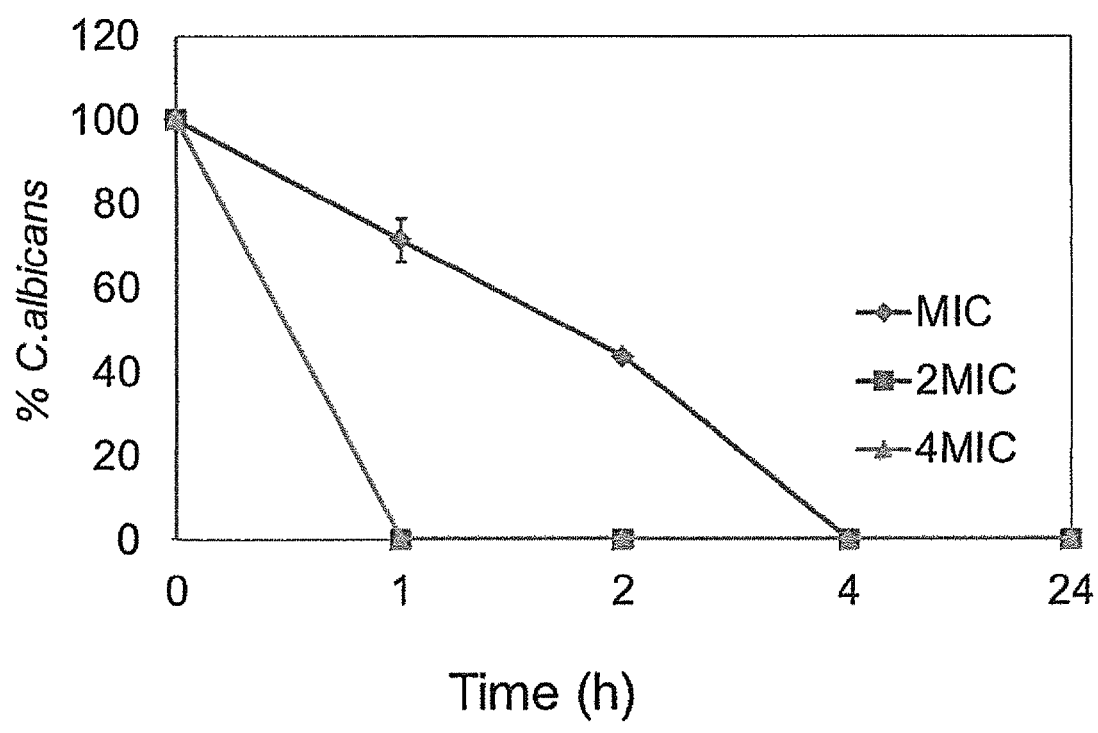
FIG. 23 shows a graph illustrating the killing kinetics of peptide (IKIK)$_2$-NH$_2$ towards *C. albicans*.

The activities of the β-sheet forming peptide (IKIK)$_2$-NH$_2$ (i.e. peptide 1) and peptide (IRIK)$_2$-NH$_2$ (i.e. peptide 2) were investigated in comparison with the non-β-sheet forming peptide (IIRK)$_2$-NH$_2$ (i.e. peptide 3) against keratitis-related fungi including *C. albicans* and *F. solani*. As seen from Table 8, the designed β-sheet forming peptides 1 and 2 demonstrated strong antifungal activities with MIC values ranging from 2-3.9 mg/L against *C. albicans*, and 31.3 mg/L for *F. solani*. In contrast, the non-β-sheet forming peptide 3 exhibited only modest activities against *C. albicans* with a drastically higher MIC of >500 mg/L, and was not found to be effective at all against *F. solani*. This result demonstrated that the formation of β-sheet secondary structures upon interacting with microbial membranes was important to the antifungal effects of the designed peptides. Due to the superior activities against *C. albicans*, killing kinetics studies were conducted with peptide 1. As shown in FIG. 23, the number of *C. albicans* cells decreased significantly after 2 h treatment at MIC level. Most fungi were killed after 4 h at MIC, and after 1 h at 2×MIC and 4×MIC. These results indicated a time and dose-dependent fungicidal mechanism of action; a higher concentration of peptide was effective at eradicating all the fungi within a shorter period of time.

TABLE 8

Minimum inhibitory concentrations (MICs) of antimicrobial peptides

| MIC (mg/L) | C. albicans | F. solani |
|---|---|---|
| (IKIK)$_2$ | 2.0 | 31.3 |
| (IRIK)$_2$ | 3.9 | 31.3 |
| (IIRK)$_2$ | >500 | >500 |

Figure 24:
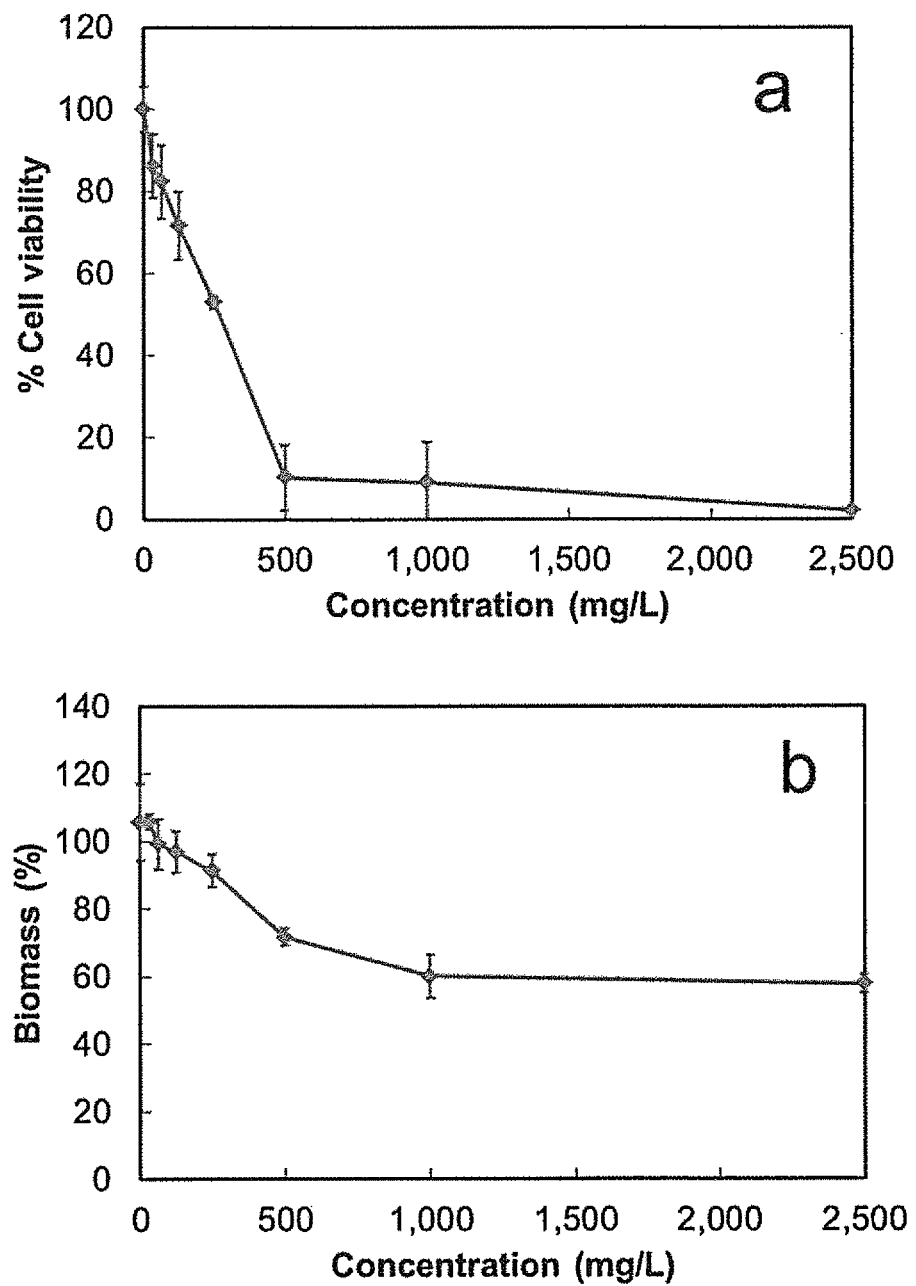
FIG. 24 shows a graph showing the percentage cell viability of *C. albicans* after treatment with peptide (IKIK)$_2$-NH$_2$ for 24 hours.
Figure 25:
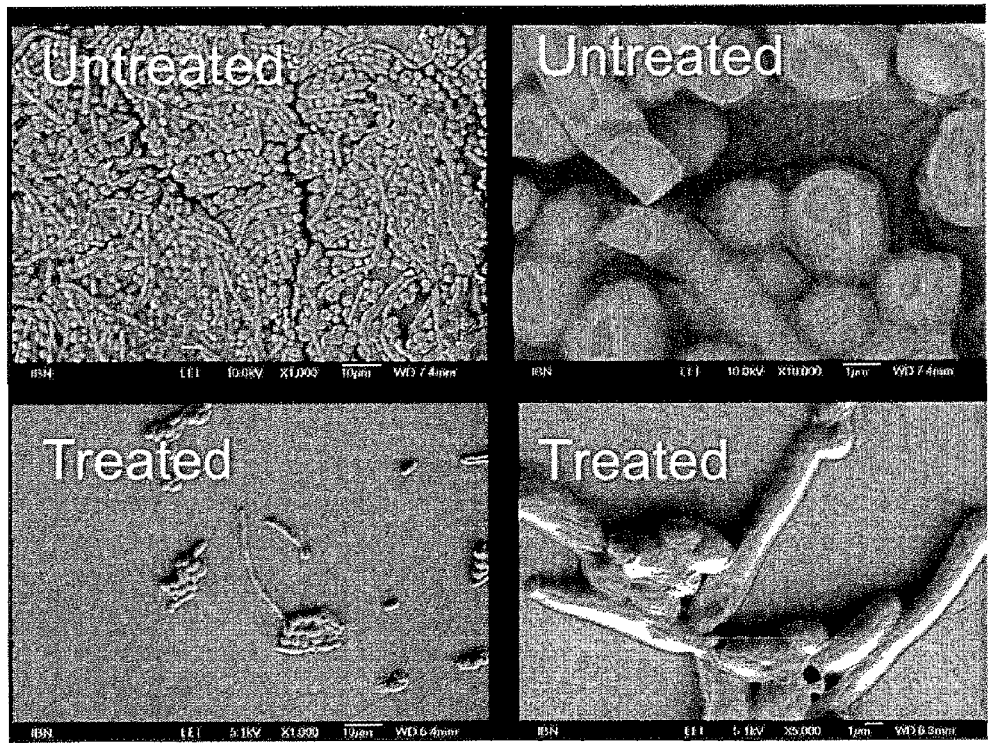
FIG. 25 shows an field emission scanning electron micrograph images of the morphological state of *C. albicans* biofilm before and after treatment with peptide (IKIK)$_2$-NH$_2$. *C. albicans* cell morphology was deformed and biomass was significantly reduced after 24 hours treatment. Thus.

Most antifungal regents are not effective against fungal keratitis because fungal keratitis infection often exists as a biofilm where fungal cells are attached together and enclosed within a self-produced ECM. Peptide 1 was used to treat *C. albicans* biofilm grown in vitro. As shown in FIG. 24A, 90% of cells were killed in 24 h after a single peptide treatment of 500 mg/L. The biomass of *C. albicans* biofilm decreased significantly after the treatment at the same peptide concentration (FIG. 24B). Increasing peptide concentration led to a further decrease in biomass. In addition, SEM studies further demonstrated that the morphology of *C. albicans* cells was deformed, and biomass was significantly decreased after the peptide treatment for 24 h at 1000 mg/L (FIG. 25).

Figure 26:
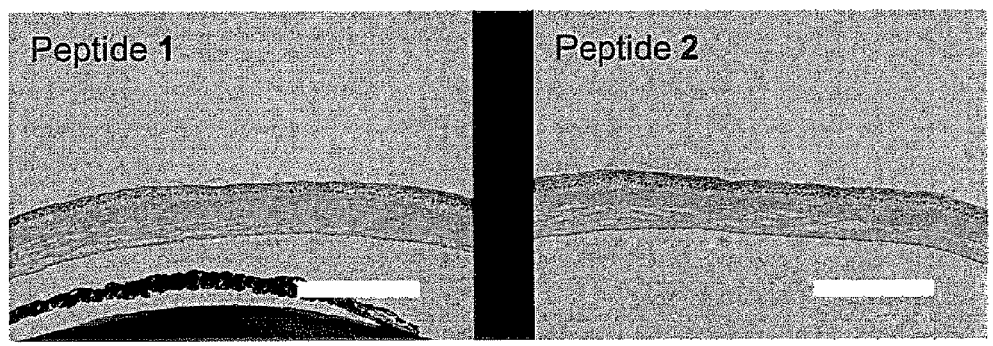
FIG. 26 shows histological images of the cornea after topical administration of peptide (IKIK)$_2$-NH$_2$ (i.e. peptide 1) and peptide (IRIK)$_2$-NH$_2$ (i.e. peptide 2). Histological sections of mouse corneas with hematoxycin and eosin after topical administration of the peptides. Scale bar: 200 μm. Histological images of the corneas after topical administration of 3000 mg/L of peptides 1 and 2 did not show significant signs of corneal epithelial erosion, and the application of the peptides did not lead to obvious pathological changes in the underlying stroma. Thus.

In addition, stability of peptide 1 was tested. Peptide 1 solution was autoclaved and kept at room temperature for 6 weeks without any protection from light. The molecular weight of peptide 1 remained unchanged with no degradation products observed, demonstrating that the peptide can be sterilized by autoclaving, and was stable in water. The toxicitiy of peptides 1 and 2 (3000 mg/L each) was evaluated in mice eyes. Histological images of the cornea after topical administration of the peptides did not show significant signs of corneal epithelial erosion, and the application of the high concentration of peptides did not lead to obvious pathological changes in the underlying stroma (FIG. 26). Taken together, these results demonstrated that peptides 1 and 2 have high potency against both planktonic keratitis-related fungi and their biofilms, as well as excellent stability. In addition, they were non-toxic to the eyes when used as eye drops.

Figure 27:
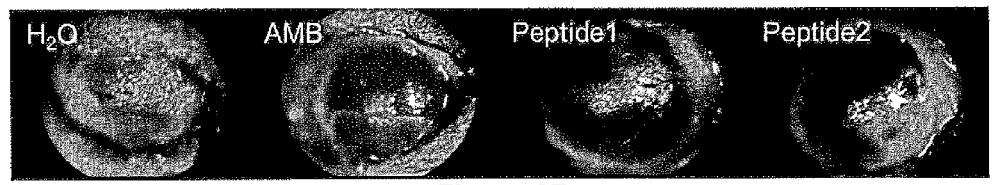
FIG. 27 shows photographical images of mouse eyes with C. albicans keratitis after treatment with $H_2O$ (control), amphotericin B (AMB) (1000 mg/L), peptide $(IKIK)_2$-$NH_2$ (i.e. peptide 1) (3000 mg/L) and peptide $(IRIK)_2$-$NH_2$ (i.e. peptide 2) (3000 mg/L). Significant resolution of the keratitis infection was observed after the treatment, with the corneas becoming more transparent and the iris being visible, as compared with the control group. Thus.
Figure 28:
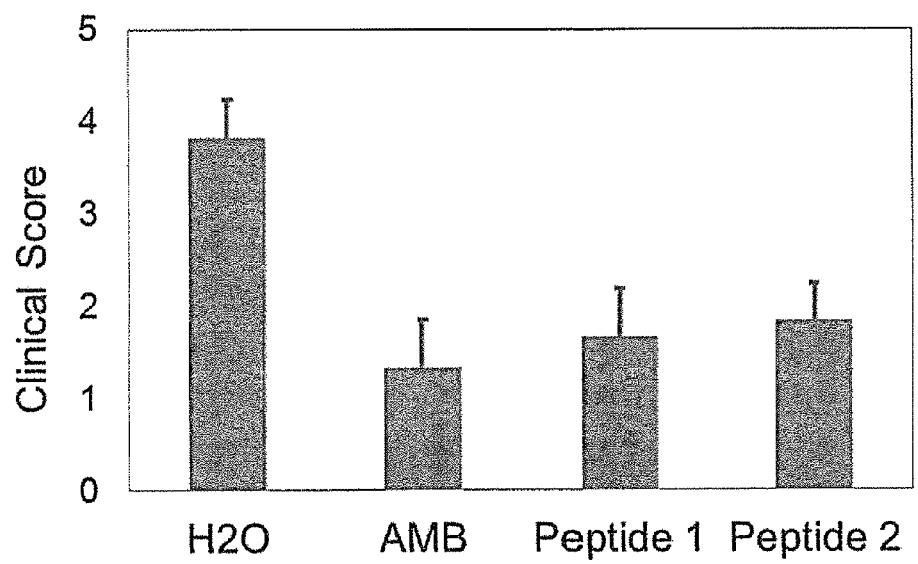
FIG. 28 shows a bar graph depicting clinical slit lamp scores (±standard deviation) for keratitis before and after treatment with four topical eye drop solutions: $H_2O$ (control), amphotericin B (AMB) (1000 mg/L), peptide $(IKIK)_2$-$NH_2$ (i.e. peptide 1) (3000 mg/L) and peptide $(IRIK)_2$-$NH_2$ (i.e. peptide 2) (3000 mg/L). The clinical scores of the amphotericin B-treated and peptide-treated eyes were significantly lower than that of the eyes in the control group (P<0.01). Thus.
Figure 29:
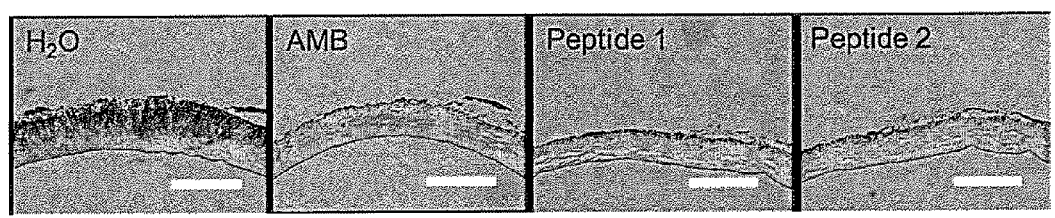
FIG. 29 shows histological images of corneas treated with the specified solutions. The cornea samples were embedded in paraffin and serially sectioned to be stained with PAS; fungi were stained in pink. Scale bar: 200 μm. Fungal hyphae extended into the stroma of cornea in the control group, while the treatments with amphotericin B (AMB), peptide 1 and peptide 2 reduced the maximal depth of hyphal invasion into the corneas. Thus, FIG. 29 verified that the peptides of the present disclosure significantly reduced fungi infiltration into the cornea inflicted with keratitis.

In order to investigate the potential application of the peptides in fungi keratitis treatment, *C. albicans* keratitis model was established in mice. *C. albicans* were first cultured on contact lens for biofilm formation. The contact lens containing a layer of *C. albicans* biofilm was then transferred onto the surface of de-epithelial cornea of mice. After 18 h inoculation, the *C. albicans* biofilm infected the cornea, resulting in the formation of eye ulcers with a leathery, tough, raised surface. Peptide 1 solution (3000 mg/L), peptide 2 solution (3000 mg/L), amphotericin B (1000 mg/L) and water (control) were applied topically as eye drops on the surface of the cornea in 20-µL quantities. After treatment, significant resolution of the keratitis infection was observed, with the corneas becoming more transparent and the iris being visible, as compared with the control group. The treatment efficacy of the peptides was comparable with that of amphotericin B (FIG. 27). Clinical scores of the fungal keratitis before and after treatment were evaluated according to the clinical standard. As shown in FIG. 28, the clinical scores of mice corneas in all treatment groups were significantly lower than that in the control group. In addition, treated eyeballs were fixed and stained with Periodic acid-Schiff (PAS). Fungal hyphae extended into the stroma of cornea in the control group, while the treatments with peptide 1, peptide 2 and amphotericin B reduced the maximal depth of hyphal invasion into the cornea (FIG. 29). The histological studies further verified that the treatments with the peptides and amphotericin B significantly reduced fungi infiltration into the cornea inflicted with keratitis.

Figure 30:
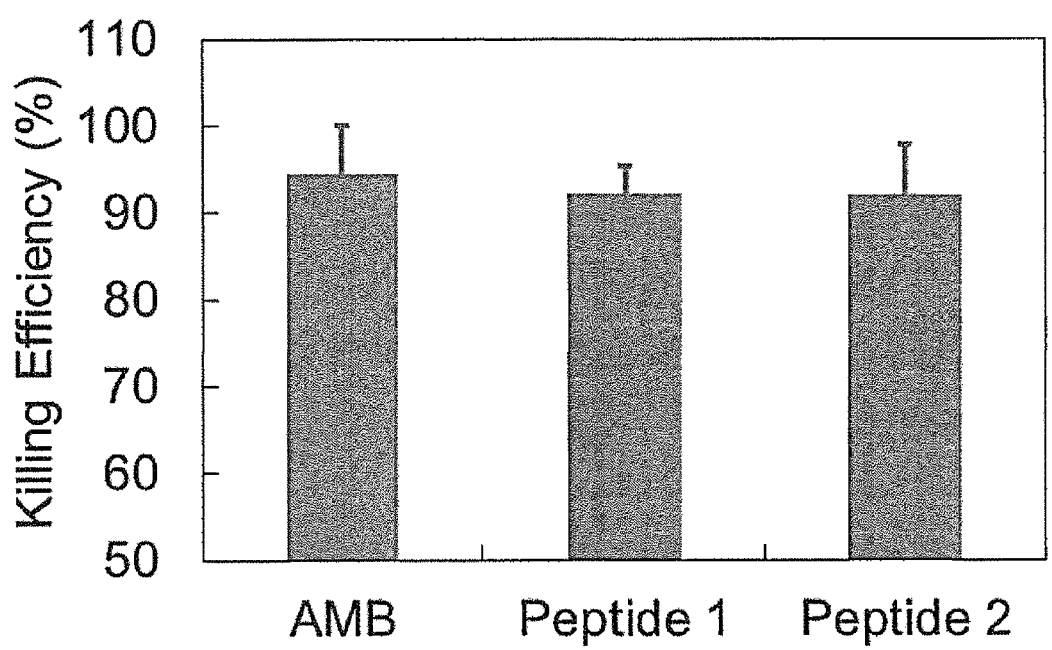
FIG. 30 shows a bar graph depicting microbiology counts of C. albicans in mice cornea after treatment with amphotericin B (AMB), peptide $(IKIK)_2$-$NH_2$ (i.e. peptide 1) and peptide $(IRIK)_2$-$NH_2$ (i.e. peptide 2). Six cornea samples from each group (one eye from each mouse) were collected and analyzed. The peptides were as effective as amphotericin B in reducing the number of C. albicans colonies in the eyeballs, and ~90% fungal cells were eradicated from the biofilms after the treatments, as compared to the untreated control group. Thus.

To quantify fungi counts in the treated eyeballs, the treated eyeballs were homogenized and the number of *C. albicans* cells in each eyeball was determined via agar plating. The peptides were as effective as amphotericin B in reducing the number of *C. albicans* colonies in the eyeballs, and ~90% fungal cells were eradicated from the biofilms after the treatments, as compared to the untreated control group (FIG. 30). Taken together, these synthetic β-sheet forming peptides were effective in eradicating the sessile keratitis-related fungi and their biofilms in mouse eyes.

Thus, in the present disclosure, the inventors of the present disclosure have demonstrated that the β-sheet forming peptides have strong anti-fungi activities, and are capable of removing fungi biofilm formed both in vitro and in a fungal biofilm-induced keratitis mouse model without causing significant toxicity to the eyes. The peptides are water-soluble, and stable in a autoclaving procedure. They are useful anti-fungal agents for treating fungal keratitis.

The invention claimed is:

1. A method of treating a subject suffering from keratitis comprising administration of a pharmaceutically effective amount of an amphiphilic peptide, wherein the peptide comprises: $(X_1Y_1X_2Y_2)_n$ (Formula I), wherein
the C-terminal end of the peptide is amidated;
$X_1$ and $X_2$ is independently of each other a hydrophobic amino acid;
$Y_1$ and $Y_2$ is independently of each other a cationic amino acids; and
n is any number selected from the group consisting of 1.5, 2, 2.5, 3, 3.5, 4, 4.5, and 5; and
wherein when assembled, the peptide has β-sheet structure.

2. The method of claim 1, wherein the keratitis is caused by bacteria selected from the group consisting of *Pseudomonas aeruginosa*, *Streptococcus pneumonia*, *Staphylococcus aureus* and *Staphylococcus epidermidis*.

3. The method of claim 1, wherein the keratitis is caused by virus selected from the group consisting of varicella zoster, adenoviruses and Herpes simplex virus-1 (HSV-1).

4. The method of claim 1, wherein the keratitis is caused by fungus selected from the group consisting of filamentous fungi and/or yeast-like fungi.

5. The method of claim 4, wherein the yeast-like fungi is *Candida albicans*.

6. The method of claim 4, wherein the filamentous fungi is selected from the group consisting of *Aspergillus flavus*, *Aspergillus fumigatus*, *Fusarium* spp., *Alternaria* spp., and *Paecilomyces lilacinus*.

* * * * *

SEQUENCE LISTING

```
<160> NUMBER OF SEQ ID NOS: 27

<210> SEQ ID NO 1
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(4)
<223> OTHER INFORMATION: n = 1
<220> FEATURE:
<221> NAME/KEY: MISC_FEATURE
<222> LOCATION: (1)..(1)
<223> OTHER INFORMATION: hydrophobic amino acid
<220> FEATURE:
<221> NAME/KEY: MISC_FEATURE
<222> LOCATION: (2)..(2)
<223> OTHER INFORMATION: cationic amino acid
<220> FEATURE:
<221> NAME/KEY: MISC_FEATURE
<222> LOCATION: (3)..(3)
<223> OTHER INFORMATION: hydrophobic amino acid
<220> FEATURE:
<221> NAME/KEY: MISC_FEATURE
<222> LOCATION: (4)..(4)
<223> OTHER INFORMATION: cationic amino acid

<400> SEQUENCE: 1

Xaa Xaa Xaa Xaa
1

<210> SEQ ID NO 2
<211> LENGTH: 6
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: MISC_FEATURE
<222> LOCATION: (1)..(6)
<223> OTHER INFORMATION: n =1.5
<220> FEATURE:
<221> NAME/KEY: MISC_FEATURE
<222> LOCATION: (1)..(1)
<223> OTHER INFORMATION: hydrophobic amino acid
<220> FEATURE:
<221> NAME/KEY: MISC_FEATURE
<222> LOCATION: (2)..(2)
<223> OTHER INFORMATION: cationic amino acid
<220> FEATURE:
<221> NAME/KEY: MISC_FEATURE
<222> LOCATION: (3)..(3)
<223> OTHER INFORMATION: hydrophobic amino acid
<220> FEATURE:
<221> NAME/KEY: MISC_FEATURE
<222> LOCATION: (4)..(4)
<223> OTHER INFORMATION: cationic amino acid
<220> FEATURE:
<221> NAME/KEY: MISC_FEATURE
<222> LOCATION: (5)..(5)
<223> OTHER INFORMATION: hydrophobic amino acid
<220> FEATURE:
<221> NAME/KEY: MISC_FEATURE
<222> LOCATION: (6)..(6)
<223> OTHER INFORMATION: cationic amino acid

<400> SEQUENCE: 2

Xaa Xaa Xaa Xaa Xaa Xaa
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: n = 2
<220> FEATURE:
<221> NAME/KEY: MISC_FEATURE
<222> LOCATION: (1)..(1)
<223> OTHER INFORMATION: hydrophobic amino acid
<220> FEATURE:
<221> NAME/KEY: MISC_FEATURE
<222> LOCATION: (2)..(2)
<223> OTHER INFORMATION: cationic amino acid
<220> FEATURE:
<221> NAME/KEY: MISC_FEATURE
<222> LOCATION: (3)..(3)
<223> OTHER INFORMATION: hydrophobic amino acid
<220> FEATURE:
<221> NAME/KEY: MISC_FEATURE
<222> LOCATION: (4)..(4)
<223> OTHER INFORMATION: cationic amino acid
<220> FEATURE:
<221> NAME/KEY: MISC_FEATURE
<222> LOCATION: (5)..(5)
<223> OTHER INFORMATION: hydrophobic amino acid
<220> FEATURE:
<221> NAME/KEY: MISC_FEATURE
<222> LOCATION: (6)..(6)
<223> OTHER INFORMATION: cationic amino acid
<220> FEATURE:
<221> NAME/KEY: MISC_FEATURE
<222> LOCATION: (7)..(7)
<223> OTHER INFORMATION: hydrophobic amino acid
<220> FEATURE:
<221> NAME/KEY: MISC_FEATURE
<222> LOCATION: (8)..(8)
<223> OTHER INFORMATION: cationic amino acid
```

```
<400> SEQUENCE: 3

Xaa Xaa Xaa Xaa Xaa Xaa Xaa Xaa
1               5

<210> SEQ ID NO 4
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(10)
<223> OTHER INFORMATION: n= 2.5
<220> FEATURE:
<221> NAME/KEY: MISC_FEATURE
<222> LOCATION: (1)..(1)
<223> OTHER INFORMATION: hydrophobic amino acid
<220> FEATURE:
<221> NAME/KEY: MISC_FEATURE
<222> LOCATION: (2)..(2)
<223> OTHER INFORMATION: cationic amino acid
<220> FEATURE:
<221> NAME/KEY: MISC_FEATURE
<222> LOCATION: (3)..(3)
<223> OTHER INFORMATION: hydrophobic amino acid
<220> FEATURE:
<221> NAME/KEY: MISC_FEATURE
<222> LOCATION: (4)..(4)
<223> OTHER INFORMATION: cationic amino acid
<220> FEATURE:
<221> NAME/KEY: MISC_FEATURE
<222> LOCATION: (5)..(5)
<223> OTHER INFORMATION: hydrophobic amino acid
<220> FEATURE:
<221> NAME/KEY: MISC_FEATURE
<222> LOCATION: (6)..(6)
<223> OTHER INFORMATION: cationic amino acid
<220> FEATURE:
<221> NAME/KEY: MISC_FEATURE
<222> LOCATION: (7)..(7)
<223> OTHER INFORMATION: hydrophobic amino acid
<220> FEATURE:
<221> NAME/KEY: MISC_FEATURE
<222> LOCATION: (8)..(8)
<223> OTHER INFORMATION: cationic amino acid
<220> FEATURE:
<221> NAME/KEY: MISC_FEATURE
<222> LOCATION: (9)..(9)
<223> OTHER INFORMATION: hydrophobic amino acid
<220> FEATURE:
<221> NAME/KEY: MISC_FEATURE
<222> LOCATION: (10)..(10)
<223> OTHER INFORMATION: cationic amino acid

<400> SEQUENCE: 4

Xaa Xaa Xaa Xaa Xaa Xaa Xaa Xaa Xaa Xaa
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(12)
<223> OTHER INFORMATION: n = 3
<220> FEATURE:
<221> NAME/KEY: MISC_FEATURE
<222> LOCATION: (1)..(1)
<223> OTHER INFORMATION: hydrophobic amino acid
```

```
<220> FEATURE:
<221> NAME/KEY: MISC_FEATURE
<222> LOCATION: (2)..(2)
<223> OTHER INFORMATION: cationic amino acid
<220> FEATURE:
<221> NAME/KEY: MISC_FEATURE
<222> LOCATION: (3)..(3)
<223> OTHER INFORMATION: hydrophobic amino acid
<220> FEATURE:
<221> NAME/KEY: MISC_FEATURE
<222> LOCATION: (4)..(4)
<223> OTHER INFORMATION: cationic amino acid
<220> FEATURE:
<221> NAME/KEY: MISC_FEATURE
<222> LOCATION: (5)..(5)
<223> OTHER INFORMATION: hydrophobic amino acid
<220> FEATURE:
<221> NAME/KEY: MISC_FEATURE
<222> LOCATION: (6)..(6)
<223> OTHER INFORMATION: cationic amino acid
<220> FEATURE:
<221> NAME/KEY: MISC_FEATURE
<222> LOCATION: (7)..(7)
<223> OTHER INFORMATION: hydrophobic amino acid
<220> FEATURE:
<221> NAME/KEY: MISC_FEATURE
<222> LOCATION: (8)..(8)
<223> OTHER INFORMATION: cationic amino acid
<220> FEATURE:
<221> NAME/KEY: MISC_FEATURE
<222> LOCATION: (9)..(9)
<223> OTHER INFORMATION: hydrophobic amino acid
<220> FEATURE:
<221> NAME/KEY: MISC_FEATURE
<222> LOCATION: (10)..(10)
<223> OTHER INFORMATION: cationic amino acid
<220> FEATURE:
<221> NAME/KEY: MISC_FEATURE
<222> LOCATION: (11)..(11)
<223> OTHER INFORMATION: hydrophobic amino acid
<220> FEATURE:
<221> NAME/KEY: MISC_FEATURE
<222> LOCATION: (12)..(12)
<223> OTHER INFORMATION: cationic amino acid

<400> SEQUENCE: 5

Xaa Xaa Xaa Xaa Xaa Xaa Xaa Xaa Xaa Xaa Xaa Xaa
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(14)
<223> OTHER INFORMATION: n = 3.5
<220> FEATURE:
<221> NAME/KEY: MISC_FEATURE
<222> LOCATION: (1)..(1)
<223> OTHER INFORMATION: hydrophobic amino acid
<220> FEATURE:
<221> NAME/KEY: MISC_FEATURE
<222> LOCATION: (2)..(2)
<223> OTHER INFORMATION: cationic amino acid
<220> FEATURE:
<221> NAME/KEY: MISC_FEATURE
<222> LOCATION: (3)..(3)
<223> OTHER INFORMATION: hydrophobic amino acid
<220> FEATURE:
<221> NAME/KEY: MISC_FEATURE
<222> LOCATION: (4)..(4)
<223> OTHER INFORMATION: cationic amino acid
```

```
<220> FEATURE:
<221> NAME/KEY: MISC_FEATURE
<222> LOCATION: (5)..(5)
<223> OTHER INFORMATION: hydrophobic amino acid
<220> FEATURE:
<221> NAME/KEY: MISC_FEATURE
<222> LOCATION: (6)..(6)
<223> OTHER INFORMATION: cationic amino acid
<220> FEATURE:
<221> NAME/KEY: MISC_FEATURE
<222> LOCATION: (7)..(7)
<223> OTHER INFORMATION: hydrophobic amino acid
<220> FEATURE:
<221> NAME/KEY: MISC_FEATURE
<222> LOCATION: (8)..(8)
<223> OTHER INFORMATION: cationic amino acid
<220> FEATURE:
<221> NAME/KEY: MISC_FEATURE
<222> LOCATION: (9)..(9)
<223> OTHER INFORMATION: hydrophobic amino acid
<220> FEATURE:
<221> NAME/KEY: MISC_FEATURE
<222> LOCATION: (10)..(10)
<223> OTHER INFORMATION: cationic amino acid
<220> FEATURE:
<221> NAME/KEY: MISC_FEATURE
<222> LOCATION: (11)..(11)
<223> OTHER INFORMATION: hydrophobic amino acid
<220> FEATURE:
<221> NAME/KEY: MISC_FEATURE
<222> LOCATION: (12)..(12)
<223> OTHER INFORMATION: cationic amino acid
<220> FEATURE:
<221> NAME/KEY: MISC_FEATURE
<222> LOCATION: (13)..(13)
<223> OTHER INFORMATION: hydrophobic amino acid
<220> FEATURE:
<221> NAME/KEY: MISC_FEATURE
<222> LOCATION: (14)..(14)
<223> OTHER INFORMATION: cationic amino acid

<400> SEQUENCE: 6

Xaa Xaa Xaa Xaa Xaa Xaa Xaa Xaa Xaa Xaa Xaa Xaa Xaa Xaa
1               5                   10

<210> SEQ ID NO 7
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(16)
<223> OTHER INFORMATION: n = 4
<220> FEATURE:
<221> NAME/KEY: MISC_FEATURE
<222> LOCATION: (1)..(1)
<223> OTHER INFORMATION: hydrophobic amino acid
<220> FEATURE:
<221> NAME/KEY: MISC_FEATURE
<222> LOCATION: (2)..(2)
<223> OTHER INFORMATION: cationic amino acid
<220> FEATURE:
<221> NAME/KEY: MISC_FEATURE
<222> LOCATION: (3)..(3)
<223> OTHER INFORMATION: hydrophobic amino acid
<220> FEATURE:
<221> NAME/KEY: MISC_FEATURE
<222> LOCATION: (4)..(4)
<223> OTHER INFORMATION: cationic amino acid
<220> FEATURE:
<221> NAME/KEY: MISC_FEATURE
<222> LOCATION: (5)..(5)
<223> OTHER INFORMATION: hydrophobic amino acid
```

```
-continued

<220> FEATURE:
<221> NAME/KEY: MISC_FEATURE
<222> LOCATION: (6)..(6)
<223> OTHER INFORMATION: cationic amino acid
<220> FEATURE:
<221> NAME/KEY: MISC_FEATURE
<222> LOCATION: (7)..(7)
<223> OTHER INFORMATION: hydrophobic amino acid
<220> FEATURE:
<221> NAME/KEY: MISC_FEATURE
<222> LOCATION: (8)..(8)
<223> OTHER INFORMATION: cationic amino acid
<220> FEATURE:
<221> NAME/KEY: MISC_FEATURE
<222> LOCATION: (9)..(9)
<223> OTHER INFORMATION: hydrophobic amino acid
<220> FEATURE:
<221> NAME/KEY: MISC_FEATURE
<222> LOCATION: (10)..(10)
<223> OTHER INFORMATION: cationic amino acid
<220> FEATURE:
<221> NAME/KEY: MISC_FEATURE
<222> LOCATION: (11)..(11)
<223> OTHER INFORMATION: hydrophobic amino acid
<220> FEATURE:
<221> NAME/KEY: MISC_FEATURE
<222> LOCATION: (12)..(12)
<223> OTHER INFORMATION: cationic amino acid
<220> FEATURE:
<221> NAME/KEY: MISC_FEATURE
<222> LOCATION: (13)..(13)
<223> OTHER INFORMATION: hydrophobic amino acid
<220> FEATURE:
<221> NAME/KEY: MISC_FEATURE
<222> LOCATION: (14)..(14)
<223> OTHER INFORMATION: cationic amino acid
<220> FEATURE:
<221> NAME/KEY: MISC_FEATURE
<222> LOCATION: (15)..(15)
<223> OTHER INFORMATION: hydrophobic amino acid
<220> FEATURE:
<221> NAME/KEY: MISC_FEATURE
<222> LOCATION: (16)..(16)
<223> OTHER INFORMATION: cationic amino acid

<400> SEQUENCE: 7

Xaa Xaa Xaa Xaa Xaa Xaa Xaa Xaa Xaa Xaa Xaa Xaa Xaa Xaa Xaa Xaa
1               5                   10                  15

<210> SEQ ID NO 8
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(18)
<223> OTHER INFORMATION: n = 4.5
<220> FEATURE:
<221> NAME/KEY: MISC_FEATURE
<222> LOCATION: (1)..(1)
<223> OTHER INFORMATION: hydrophobic amino acid
<220> FEATURE:
<221> NAME/KEY: MISC_FEATURE
<222> LOCATION: (2)..(2)
<223> OTHER INFORMATION: cationic amino acid
<220> FEATURE:
<221> NAME/KEY: MISC_FEATURE
<222> LOCATION: (3)..(3)
<223> OTHER INFORMATION: hydrophobic amino acid
<220> FEATURE:
<221> NAME/KEY: MISC_FEATURE
<222> LOCATION: (4)..(4)
<223> OTHER INFORMATION: cationic amino acid
```

```
<220> FEATURE:
<221> NAME/KEY: MISC_FEATURE
<222> LOCATION: (5)..(5)
<223> OTHER INFORMATION: hydrophobic amino acid
<220> FEATURE:
<221> NAME/KEY: MISC_FEATURE
<222> LOCATION: (6)..(6)
<223> OTHER INFORMATION: cationic amino acid
<220> FEATURE:
<221> NAME/KEY: MISC_FEATURE
<222> LOCATION: (7)..(7)
<223> OTHER INFORMATION: hydrophobic amino acid
<220> FEATURE:
<221> NAME/KEY: MISC_FEATURE
<222> LOCATION: (8)..(8)
<223> OTHER INFORMATION: cationic amino acid
<220> FEATURE:
<221> NAME/KEY: MISC_FEATURE
<222> LOCATION: (9)..(9)
<223> OTHER INFORMATION: hydrophobic amino acid
<220> FEATURE:
<221> NAME/KEY: MISC_FEATURE
<222> LOCATION: (10)..(10)
<223> OTHER INFORMATION: cationic amino acid
<220> FEATURE:
<221> NAME/KEY: MISC_FEATURE
<222> LOCATION: (11)..(11)
<223> OTHER INFORMATION: hydrophobic amino acid
<220> FEATURE:
<221> NAME/KEY: MISC_FEATURE
<222> LOCATION: (12)..(12)
<223> OTHER INFORMATION: cationic amino acid
<220> FEATURE:
<221> NAME/KEY: MISC_FEATURE
<222> LOCATION: (13)..(13)
<223> OTHER INFORMATION: hydrophobic amino acid
<220> FEATURE:
<221> NAME/KEY: MISC_FEATURE
<222> LOCATION: (14)..(14)
<223> OTHER INFORMATION: cationic amino acid
<220> FEATURE:
<221> NAME/KEY: MISC_FEATURE
<222> LOCATION: (15)..(15)
<223> OTHER INFORMATION: hydrophobic amino acid
<220> FEATURE:
<221> NAME/KEY: MISC_FEATURE
<222> LOCATION: (16)..(16)
<223> OTHER INFORMATION: cationic amino acid
<220> FEATURE:
<221> NAME/KEY: MISC_FEATURE
<222> LOCATION: (17)..(17)
<223> OTHER INFORMATION: hydrophobic amino acid
<220> FEATURE:
<221> NAME/KEY: MISC_FEATURE
<222> LOCATION: (18)..(18)
<223> OTHER INFORMATION: cationic amino acid

<400> SEQUENCE: 8

Xaa Xaa Xaa Xaa Xaa Xaa Xaa Xaa Xaa Xaa Xaa Xaa Xaa Xaa Xaa Xaa
1               5                   10                  15

Xaa Xaa

<210> SEQ ID NO 9
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(20)
<223> OTHER INFORMATION: n = 5
<220> FEATURE:
<221> NAME/KEY: MISC_FEATURE
<222> LOCATION: (1)..(1)
<223> OTHER INFORMATION: hydrophobic amino acid
```

```
-continued

<220> FEATURE:
<221> NAME/KEY: MISC_FEATURE
<222> LOCATION: (2)..(2)
<223> OTHER INFORMATION: cationic amino acid
<220> FEATURE:
<221> NAME/KEY: MISC_FEATURE
<222> LOCATION: (3)..(3)
<223> OTHER INFORMATION: hydrophobic amino acid
<220> FEATURE:
<221> NAME/KEY: MISC_FEATURE
<222> LOCATION: (4)..(4)
<223> OTHER INFORMATION: cationic amino acid
<220> FEATURE:
<221> NAME/KEY: MISC_FEATURE
<222> LOCATION: (5)..(5)
<223> OTHER INFORMATION: hydrophobic amino acid
<220> FEATURE:
<221> NAME/KEY: MISC_FEATURE
<222> LOCATION: (6)..(6)
<223> OTHER INFORMATION: cationic amino acid
<220> FEATURE:
<221> NAME/KEY: MISC_FEATURE
<222> LOCATION: (7)..(7)
<223> OTHER INFORMATION: hydrophobic amino acid
<220> FEATURE:
<221> NAME/KEY: MISC_FEATURE
<222> LOCATION: (8)..(8)
<223> OTHER INFORMATION: cationic amino acid
<220> FEATURE:
<221> NAME/KEY: MISC_FEATURE
<222> LOCATION: (9)..(9)
<223> OTHER INFORMATION: hydrophobic amino acid
<220> FEATURE:
<221> NAME/KEY: MISC_FEATURE
<222> LOCATION: (10)..(10)
<223> OTHER INFORMATION: cationic amino acid
<220> FEATURE:
<221> NAME/KEY: MISC_FEATURE
<222> LOCATION: (11)..(11)
<223> OTHER INFORMATION: hydrophobic amino acid
<220> FEATURE:
<221> NAME/KEY: MISC_FEATURE
<222> LOCATION: (12)..(12)
<223> OTHER INFORMATION: cationic amino acid
<220> FEATURE:
<221> NAME/KEY: MISC_FEATURE
<222> LOCATION: (13)..(13)
<223> OTHER INFORMATION: hydrophobic amino acid
<220> FEATURE:
<221> NAME/KEY: MISC_FEATURE
<222> LOCATION: (14)..(14)
<223> OTHER INFORMATION: cationic amino acid
<220> FEATURE:
<221> NAME/KEY: MISC_FEATURE
<222> LOCATION: (15)..(15)
<223> OTHER INFORMATION: hydrophobic amino acid
<220> FEATURE:
<221> NAME/KEY: MISC_FEATURE
<222> LOCATION: (16)..(16)
<223> OTHER INFORMATION: cationic amino acid
<220> FEATURE:
<221> NAME/KEY: MISC_FEATURE
<222> LOCATION: (17)..(17)
<223> OTHER INFORMATION: hydrophobic amino acid
<220> FEATURE:
<221> NAME/KEY: MISC_FEATURE
<222> LOCATION: (18)..(18)
<223> OTHER INFORMATION: cationic amino acid
<220> FEATURE:
<221> NAME/KEY: MISC_FEATURE
<222> LOCATION: (19)..(19)
<223> OTHER INFORMATION: hydrophobic amino acid
<220> FEATURE:
<221> NAME/KEY: MISC_FEATURE
<222> LOCATION: (20)..(20)
<223> OTHER INFORMATION: cationic amino acid
```

```
<400> SEQUENCE: 9

Xaa Xaa Xaa Xaa Xaa Xaa Xaa Xaa Xaa Xaa Xaa Xaa Xaa Xaa Xaa
1               5                   10                  15

Xaa Xaa Xaa Xaa
            20

<210> SEQ ID NO 10
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: n = 1.5
<220> FEATURE:
<221> NAME/KEY: MISC_FEATURE
<222> LOCATION: (1)..(6)
<223> OTHER INFORMATION: D amino acids
<220> FEATURE:
<221> NAME/KEY: MISC_FEATURE
<222> LOCATION: (6)..(6)
<223> OTHER INFORMATION: C-terminal amidated

<400> SEQUENCE: 10

Ile Arg Ile Lys Ile Arg
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: n = 2
<220> FEATURE:
<221> NAME/KEY: MISC_FEATURE
<222> LOCATION: (8)..(8)
<223> OTHER INFORMATION: C-terminal amidated

<400> SEQUENCE: 11

Val Arg Val Lys Val Arg Val Lys
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: n = 2
<220> FEATURE:
<221> NAME/KEY: MISC_FEATURE
<222> LOCATION: (8)..(8)
<223> OTHER INFORMATION: C-terminal amidated

<400> SEQUENCE: 12

Ile Arg Ile Arg Ile Arg Ile Arg
1               5
```

```
<210> SEQ ID NO 13
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: n = 2
<220> FEATURE:
<221> NAME/KEY: MISC_FEATURE
<222> LOCATION: (8)..(8)
<223> OTHER INFORMATION: C-terminal amidated

<400> SEQUENCE: 13

Ile Lys Ile Lys Ile Lys Ile Lys
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: C-terminal amidated
<220> FEATURE:
<221> NAME/KEY: MISC_FEATURE
<222> LOCATION: (1)..(8)
<223> OTHER INFORMATION: n = 2

<400> SEQUENCE: 14

Ile Arg Val Lys Ile Arg Val Lys
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: n = 2
<220> FEATURE:
<221> NAME/KEY: MISC_FEATURE
<222> LOCATION: (8)..(8)
<223> OTHER INFORMATION: C-terminal amidated

<400> SEQUENCE: 15

Phe Arg Phe Lys Phe Arg Phe Lys
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: n = 2
<220> FEATURE:
<221> NAME/KEY: MISC_FEATURE
<222> LOCATION: (8)..(8)
<223> OTHER INFORMATION: C-terminal amidated
```

```
<400> SEQUENCE: 16

Trp Arg Trp Lys Trp Arg Trp Lys
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: n = 2
<220> FEATURE:
<221> NAME/KEY: MISC_FEATURE
<222> LOCATION: (8)..(8)
<223> OTHER INFORMATION: C-terminal amidated

<400> SEQUENCE: 17

Ile Arg Ile Lys Ile Arg Ile Lys
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: n = 2
<220> FEATURE:
<221> NAME/KEY: MISC_FEATURE
<222> LOCATION: (1)..(8)
<223> OTHER INFORMATION: D amino acids
<220> FEATURE:
<221> NAME/KEY: MISC_FEATURE
<222> LOCATION: (8)..(8)
<223> OTHER INFORMATION: C-terminal amidated

<400> SEQUENCE: 18

Ile Arg Ile Lys Ile Arg Ile Lys
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: n = 2
<220> FEATURE:
<221> NAME/KEY: MISC_FEATURE
<222> LOCATION: (1)..(1)
<223> OTHER INFORMATION: L amino acid
<220> FEATURE:
<221> NAME/KEY: MISC_FEATURE
<222> LOCATION: (2)..(2)
<223> OTHER INFORMATION: L amino acid
<220> FEATURE:
<221> NAME/KEY: MISC_FEATURE
<222> LOCATION: (3)..(3)
<223> OTHER INFORMATION: L amino acid
<220> FEATURE:
<221> NAME/KEY: MISC_FEATURE
<222> LOCATION: (4)..(4)
<223> OTHER INFORMATION: D amino acid
```

```
<220> FEATURE:
<221> NAME/KEY: MISC_FEATURE
<222> LOCATION: (5)..(5)
<223> OTHER INFORMATION: L amino acid
<220> FEATURE:
<221> NAME/KEY: MISC_FEATURE
<222> LOCATION: (6)..(6)
<223> OTHER INFORMATION: D amino acid
<220> FEATURE:
<221> NAME/KEY: MISC_FEATURE
<222> LOCATION: (7)..(7)
<223> OTHER INFORMATION: L amino acid
<220> FEATURE:
<221> NAME/KEY: MISC_FEATURE
<222> LOCATION: (8)..(8)
<223> OTHER INFORMATION: C-terminal amidated
<220> FEATURE:
<221> NAME/KEY: MISC_FEATURE
<222> LOCATION: (8)..(8)
<223> OTHER INFORMATION: L amino acid

<400> SEQUENCE: 19

Ile Arg Ile Lys Ile Arg Ile Lys
1               5

<210> SEQ ID NO 20
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(12)
<223> OTHER INFORMATION: n = 3
<220> FEATURE:
<221> NAME/KEY: MISC_FEATURE
<222> LOCATION: (12)..(12)
<223> OTHER INFORMATION: C-terminal amidated

<400> SEQUENCE: 20

Val Arg Val Lys Val Arg Val Lys Val Arg Val Lys
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(12)
<223> OTHER INFORMATION: n = 3
<220> FEATURE:
<221> NAME/KEY: MISC_FEATURE
<222> LOCATION: (12)..(12)
<223> OTHER INFORMATION: C-terminal amidated

<400> SEQUENCE: 21

Ile Arg Ile Lys Ile Arg Ile Lys Ile Arg Ile Lys
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(12)
<223> OTHER INFORMATION: n = 3
```

```
<220> FEATURE:
<221> NAME/KEY: MISC_FEATURE
<222> LOCATION: (12)..(12)
<223> OTHER INFORMATION: C-terminal amidated

<400> SEQUENCE: 22

Ile Arg Val Lys Ile Arg Val Lys Ile Arg Val Lys
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(12)
<223> OTHER INFORMATION: n = 3
<220> FEATURE:
<221> NAME/KEY: MISC_FEATURE
<222> LOCATION: (1)..(12)
<223> OTHER INFORMATION: D amino acids
<220> FEATURE:
<221> NAME/KEY: MISC_FEATURE
<222> LOCATION: (12)..(12)
<223> OTHER INFORMATION: C-terminal amidated

<400> SEQUENCE: 23

Ile Arg Val Lys Ile Arg Val Lys Ile Arg Val Lys
1               5                   10

<210> SEQ ID NO 24
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: peptide named IK8-4D
<220> FEATURE:
<221> NAME/KEY: MISC_FEATURE
<222> LOCATION: (1)..(8)
<223> OTHER INFORMATION: n = 2
<220> FEATURE:
<221> NAME/KEY: MISC_FEATURE
<222> LOCATION: (1)..(1)
<223> OTHER INFORMATION: L amino acid
<220> FEATURE:
<221> NAME/KEY: MISC_FEATURE
<222> LOCATION: (2)..(2)
<223> OTHER INFORMATION: D amino acid
<220> FEATURE:
<221> NAME/KEY: MISC_FEATURE
<222> LOCATION: (3)..(3)
<223> OTHER INFORMATION: L amino acid
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (5)..(5)
<223> OTHER INFORMATION: L amino acid
<220> FEATURE:
<221> NAME/KEY: MISC_FEATURE
<222> LOCATION: (6)..(6)
<223> OTHER INFORMATION: D amino acid
<220> FEATURE:
<221> NAME/KEY: MISC_FEATURE
<222> LOCATION: (7)..(7)
<223> OTHER INFORMATION: L amino acid
```

```
<220> FEATURE:
<221> NAME/KEY: MISC_FEATURE
<222> LOCATION: (8)..(8)
<223> OTHER INFORMATION: C-terminal amidated
<220> FEATURE:
<221> NAME/KEY: MISC_FEATURE
<222> LOCATION: (8)..(8)
<223> OTHER INFORMATION: D amino acid

<400> SEQUENCE: 24

Ile Arg Ile Lys Ile Arg Ile Lys
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: n = 2
<220> FEATURE:
<221> NAME/KEY: MISC_FEATURE
<222> LOCATION: (1)..(8)
<223> OTHER INFORMATION: L amino acid
<220> FEATURE:
<221> NAME/KEY: MISC_FEATURE
<222> LOCATION: (8)..(8)
<223> OTHER INFORMATION: C-terminal amidated

<400> SEQUENCE: 25

Ile Ile Arg Lys Ile Ile Arg Lys
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: n = 2
<220> FEATURE:
<221> NAME/KEY: MISC_FEATURE
<222> LOCATION: (1)..(8)
<223> OTHER INFORMATION: D amino acid
<220> FEATURE:
<221> NAME/KEY: MISC_FEATURE
<222> LOCATION: (8)..(8)
<223> OTHER INFORMATION: C-terminal amidated

<400> SEQUENCE: 26

Ile Ile Arg Lys Ile Ile Arg Lys
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: Control-4D
<220> FEATURE:
<221> NAME/KEY: MISC_FEATURE
<222> LOCATION: (1)..(8)
<223> OTHER INFORMATION: n = 2
```

```
<220> FEATURE:
<221> NAME/KEY: MISC_FEATURE
<222> LOCATION: (1)..(1)
<223> OTHER INFORMATION: L amino acid
<220> FEATURE:
<221> NAME/KEY: MISC_FEATURE
<222> LOCATION: (2)..(3)
<223> OTHER INFORMATION: D amino acid
<220> FEATURE:
<221> NAME/KEY: MISC_FEATURE
<222> LOCATION: (4)..(5)
<223> OTHER INFORMATION: L amino acid
<220> FEATURE:
<221> NAME/KEY: MISC_FEATURE
<222> LOCATION: (6)..(7)
<223> OTHER INFORMATION: D amino acid
<220> FEATURE:
<221> NAME/KEY: MISC_FEATURE
<222> LOCATION: (8)..(8)
<223> OTHER INFORMATION: C-terminal amidated
<220> FEATURE:
<221> NAME/KEY: MISC_FEATURE
<222> LOCATION: (8)..(8)
<223> OTHER INFORMATION: L amino acid

<400> SEQUENCE: 27

Ile Ile Arg Lys Ile Ile Arg Lys
1               5
```